(12) United States Patent
Felsher

(10) Patent No.: US 7,587,368 B2
(45) Date of Patent: Sep. 8, 2009

(54) INFORMATION RECORD INFRASTRUCTURE, SYSTEM AND METHOD

(76) Inventor: David Paul Felsher, 158 Blackhouse Rd., Trumbull, CT (US) 06611

( * ) Notice: Subject to any disclaimer, the term of this patent is extended or adjusted under 35 U.S.C. 154(b) by 1567 days.

(21) Appl. No.: 09/899,787

(22) Filed: Jul. 5, 2001

(65) Prior Publication Data

US 2002/0010679 A1 Jan. 24, 2002

(51) Int. Cl.
*G06F 21/00* (2006.01)

(52) U.S. Cl. .............. 705/65; 705/51; 705/52; 705/53; 705/54; 705/55; 705/56; 705/57; 705/58; 705/59; 705/50; 123/620; 123/640; 123/643; 380/201

(58) Field of Classification Search ............ 705/50–79; 713/189–194; 380/286; 123/620, 640, 643
See application file for complete search history.

(56) References Cited

U.S. PATENT DOCUMENTS

| | | | |
|---|---|---|---|
| 4,200,770 A | 4/1980 | Hellman |
| 4,218,582 A | 8/1980 | Hellman |
| 4,264,782 A | 4/1981 | Konheim |
| 4,306,111 A | 12/1981 | Lu |
| 4,309,569 A | 1/1982 | Merkle |
| 4,326,098 A | 4/1982 | Bouricius |
| 4,351,982 A | 9/1982 | Miller |
| 4,365,110 A | 12/1982 | Lee |
| 4,386,233 A | 5/1983 | Smid |
| 4,393,269 A | 7/1983 | Konheim |
| 4,399,323 A | 8/1983 | Henry |
| 4,405,829 A | 9/1983 | Rivest |
| 4,438,824 A | 3/1984 | Mueller-Schloer |
| 4,453,074 A | 6/1984 | Weinstein |
| 4,458,109 A | 7/1984 | Mueller-Schloer |
| 4,471,164 A | 9/1984 | Henry |
| 4,514,592 A | 4/1985 | Miyaguchi |
| 4,528,588 A | 7/1985 | Lofberg |
| 4,529,870 A | 7/1985 | Chaum |
| 4,558,176 A | 12/1985 | Arnold |
| 4,564,018 A | 1/1986 | Hutchison |

(Continued)

OTHER PUBLICATIONS

Trust Operations (Monty P. Gregor, CTFA, © 2000 by the American Bankers Association).*

(Continued)

*Primary Examiner*—Calvin Loyd Hewitt, II
*Assistant Examiner*—Cristina Owen Sherr
(74) *Attorney, Agent, or Firm*—Milde & Hoffberg LLP

(57) ABSTRACT

A method of maintaining electronic medical records, comprising the steps of receiving a medical transaction record, encrypted with an encryption key relating to a patient association of the file, accessing the encrypted medical transaction record according to a patient association; and further encrypting the encrypted accessed medical transaction record with an encryption key associated with an intended recipient of the medical record. The system and method according to the present invention presents a new business model for the creation, maintenance, transmission, and use of medical records, allowing financial burdens to be reallocated, for example more optimally or equitably, to decrease overall societal cost, or simply to provide a successful business model for a database proprietor. Secure entrusted medical records are held in trust by an independent third party on behalf of the patient, serving the medical community at large. Separately encrypted record elements may be aggregated as an information polymer.

143 Claims, 4 Drawing Sheets

U.S. PATENT DOCUMENTS

| | | |
|---|---|---|
| 4,567,600 A | 1/1986 | Massey |
| 4,575,621 A | 3/1986 | Dreifus |
| 4,578,531 A | 3/1986 | Everhart |
| 4,590,470 A | 5/1986 | Koenig |
| 4,595,950 A | 6/1986 | Lofberg |
| 4,625,076 A | 11/1986 | Okamoto |
| 4,633,036 A | 12/1986 | Hellman |
| 4,731,841 A | 3/1988 | Rosen |
| 4,734,564 A | 3/1988 | Boston |
| 4,736,203 A | 4/1988 | Sidlauskas |
| 4,752,676 A | 6/1988 | Leonard |
| 4,812,628 A | 3/1989 | Boston |
| 4,819,267 A | 4/1989 | Cargile |
| 4,827,518 A | 5/1989 | Feustel |
| 4,868,676 A | 9/1989 | Matsuura |
| 4,890,323 A | 12/1989 | Beker |
| 4,896,363 A | 1/1990 | Taylor |
| 4,926,325 A | 5/1990 | Benton |
| 4,926,480 A | 5/1990 | Chaum |
| 4,941,173 A | 7/1990 | Boule |
| 4,952,928 A | 8/1990 | Carroll |
| 4,961,142 A | 10/1990 | Elliott |
| 4,972,476 A | 11/1990 | Nathans |
| 4,977,595 A | 12/1990 | Ohta |
| 4,993,068 A | 2/1991 | Piosenka |
| 5,020,105 A | 5/1991 | Rosen |
| 5,036,461 A | 7/1991 | Elliott |
| 5,056,141 A | 10/1991 | Dyke |
| 5,056,147 A | 10/1991 | Turner |
| 5,478,993 A | 12/1995 | Derksen |
| 5,481,613 A | 1/1996 | Ford |
| 5,483,601 A | 1/1996 | Faulkner |
| 5,485,312 A | 1/1996 | Horner |
| 5,485,519 A | 1/1996 | Weiss |
| 5,497,430 A | 3/1996 | Sadovnik |
| 5,499,293 A | 3/1996 | Behram |
| 5,508,912 A | 4/1996 | Schneiderman |
| 5,511,121 A | 4/1996 | Yacobi |
| 5,519,778 A | 5/1996 | Leighton |
| 5,521,722 A | 5/1996 | Colvill |
| 5,523,739 A | 6/1996 | Manneschi |
| 5,526,428 A | 6/1996 | Arnold |
| 5,528,492 A | 6/1996 | Fukushima |
| 5,528,516 A | 6/1996 | Yemini |
| 5,533,123 A | 7/1996 | Force |
| 5,534,855 A | 7/1996 | Shockley |
| 5,535,383 A | 7/1996 | Gower |
| 5,544,255 A | 8/1996 | Smithies |
| 5,546,462 A | 8/1996 | Indeck |
| 5,546,580 A | 8/1996 | Seliger |
| 5,553,145 A * | 9/1996 | Micali ......................... 705/80 |
| 5,553,155 A | 9/1996 | Kuhns |
| 5,557,765 A * | 9/1996 | Lipner et al. ................. 380/286 |
| 5,559,885 A | 9/1996 | Drexler |
| 5,561,718 A | 10/1996 | Trew |
| 5,572,596 A | 11/1996 | Wildes |
| 5,578,808 A | 11/1996 | Taylor |
| 5,579,393 A | 11/1996 | Conner |
| 5,583,933 A | 12/1996 | Mark |
| 5,583,950 A | 12/1996 | Prokoski |
| 5,586,171 A | 12/1996 | McAllister |
| 5,586,262 A | 12/1996 | Komatsu |
| 5,588,059 A | 12/1996 | Chandes |
| 5,592,408 A | 1/1997 | Keskin |
| 5,592,549 A | 1/1997 | Nagel |
| 5,592,945 A | 1/1997 | Fiedler |
| 5,594,806 A | 1/1997 | Colbert |
| 5,604,804 A | 2/1997 | Micali |
| 5,606,609 A | 2/1997 | Houser |
| 5,608,387 A | 3/1997 | Davies |
| 5,613,004 A | 3/1997 | Cooperman |
| 5,613,012 A | 3/1997 | Hoffman |
| 5,615,277 A | 3/1997 | Hoffman |
| 5,616,904 A | 4/1997 | Fernadez |
| 5,619,991 A | 4/1997 | Sloane |
| 5,621,201 A | 4/1997 | Langhans |
| 5,621,889 A | 4/1997 | Lermuzeaux |
| 5,623,547 A | 4/1997 | Jones |
| 5,623,601 A | 4/1997 | Vu |
| 5,629,980 A | 5/1997 | Stefik |
| 5,629,982 A | 5/1997 | Micali |
| 5,631,961 A | 5/1997 | Mills |
| 5,632,011 A | 5/1997 | Landfield |
| 5,633,932 A | 5/1997 | Davis |
| 5,634,012 A | 5/1997 | Stefik |
| 5,636,282 A | 6/1997 | Holmquist |
| 5,636,292 A | 6/1997 | Rhoads |
| 5,638,443 A | 6/1997 | Stefik |
| 5,644,778 A | 7/1997 | Burks |
| 5,646,839 A | 7/1997 | Katz |
| 5,646,997 A | 7/1997 | Barton |
| 5,647,017 A | 7/1997 | Smithies |
| 5,647,364 A | 7/1997 | Schneider |
| 5,659,616 A | 8/1997 | Sudia |
| 5,659,726 A | 8/1997 | Sandford |
| 5,664,018 A | 9/1997 | Leighton |
| 5,664,109 A | 9/1997 | Johnson |
| 5,666,400 A | 9/1997 | McAllister |
| 5,666,414 A | 9/1997 | Micali |
| 5,666,416 A | 9/1997 | Micali |
| 5,666,420 A | 9/1997 | Micali |
| 5,668,878 A | 9/1997 | Brands |
| 5,677,955 A | 10/1997 | Doggett |
| 5,679,940 A | 10/1997 | Templeton |
| 5,680,460 A | 10/1997 | Tomko |
| 5,682,032 A | 10/1997 | Philipp |
| 5,682,142 A | 10/1997 | Loosmore |
| 5,687,236 A | 11/1997 | Moskowitz |
| 5,696,827 A | 12/1997 | Brands |
| 5,696,908 A | 12/1997 | Muehlberger |
| 5,699,427 A | 12/1997 | Chow |
| 5,703,562 A | 12/1997 | Nilsen |
| 5,706,427 A | 1/1998 | Tabuki |
| 5,710,834 A | 1/1998 | Rhoads |
| 5,712,912 A | 1/1998 | Tomko |
| 5,712,914 A | 1/1998 | Aucsmith |
| 5,715,403 A | 2/1998 | Stefik |
| 5,717,757 A | 2/1998 | Micali |
| 5,719,950 A | 2/1998 | Osten |
| 5,727,092 A | 3/1998 | Sandford |
| 5,734,154 A | 3/1998 | Jachimowicz |
| 5,734,752 A | 3/1998 | Knox |
| 5,737,419 A | 4/1998 | Ganesan |
| 5,737,420 A | 4/1998 | Tomko |
| 5,740,244 A | 4/1998 | Indeck |
| 5,742,683 A | 4/1998 | Lee |
| 5,742,685 A | 4/1998 | Berson |
| 5,745,555 A | 4/1998 | Mark |
| 5,745,569 A | 4/1998 | Moskowitz |
| 5,745,573 A * | 4/1998 | Lipner et al. ................. 380/286 |
| 5,745,604 A | 4/1998 | Rhoads |
| 5,748,738 A | 5/1998 | Bisbee |
| 5,748,763 A | 5/1998 | Rhoads |
| 5,748,783 A | 5/1998 | Rhoads |
| 5,748,890 A | 5/1998 | Goldberg |
| 5,751,809 A | 5/1998 | Davis |
| 5,751,836 A | 5/1998 | Wildes |
| 5,751,909 A | 5/1998 | Gower |
| 5,754,939 A | 5/1998 | Herz |
| 5,757,431 A | 5/1998 | Bradley |
| 5,757,916 A | 5/1998 | MacDoran |
| 5,761,288 A | 6/1998 | Pinard |
| 5,761,298 A | 6/1998 | Davis |
| 5,761,686 A | 6/1998 | Bloomberg |

| | | | | | |
|---|---|---|---|---|---|
| 5,763,862 A | 6/1998 | Jachimowicz | 5,857,023 A | 1/1999 | Demers |
| 5,764,789 A | 6/1998 | Pare | 5,862,223 A | 1/1999 | Walker |
| 5,765,152 A | 6/1998 | Erickson | 5,862,246 A | 1/1999 | Colbert |
| 5,767,496 A | 6/1998 | Swartz | 5,862,260 A | 1/1999 | Rhoads |
| 5,768,382 A | 6/1998 | Schneier | 5,867,578 A | 2/1999 | Brickell |
| 5,768,385 A | 6/1998 | Simon | 5,867,795 A | 2/1999 | Novis |
| 5,768,388 A | 6/1998 | Goldwasser | 5,867,802 A | 2/1999 | Borza |
| 5,768,426 A | 6/1998 | Rhoads | 5,867,821 A | 2/1999 | Ballantyne |
| 5,770,849 A | 6/1998 | Novis | 5,869,822 A | 2/1999 | Meadows |
| 5,771,071 A | 6/1998 | Bradley | 5,870,723 A | 2/1999 | Pare |
| 5,772,585 A | 6/1998 | Lavin | 5,870,744 A | 2/1999 | Sprague |
| 5,774,551 A | 6/1998 | Wu | 5,872,834 A | 2/1999 | Teitelbaum |
| 5,778,102 A | 7/1998 | Sandford | 5,872,848 A | 2/1999 | Romney |
| 5,778,882 A | 7/1998 | Raymond | 5,872,849 A | 2/1999 | Sudia |
| 5,779,634 A | 7/1998 | Ema | 5,875,108 A | 2/1999 | Hoffberg |
| 5,781,890 A | 7/1998 | Nematbakhsh | 5,876,926 A | 3/1999 | Beecham |
| 5,784,461 A | 7/1998 | Shaffer | 5,878,137 A | 3/1999 | Ippolito |
| 5,784,463 A | 7/1998 | Chen | 5,878,144 A | 3/1999 | Aucsmith |
| 5,784,566 A | 7/1998 | Viavant | 5,881,225 A | 3/1999 | Worth |
| 5,787,187 A | 7/1998 | Bouchard | 5,881,226 A | 3/1999 | Veneklase |
| 5,789,733 A | 8/1998 | Jachimowicz | 5,884,277 A | 3/1999 | Khosla |
| 5,790,665 A | 8/1998 | Micali | 5,889,474 A | 3/1999 | LaDue |
| 5,790,668 A | 8/1998 | Tomko | 5,889,862 A | 3/1999 | Ohta |
| 5,790,674 A | 8/1998 | Houvener | 5,889,863 A | 3/1999 | Weber |
| 5,790,703 A | 8/1998 | Wang | 5,889,868 A | 3/1999 | Moskowitz |
| 5,793,868 A | 8/1998 | Micali | 5,890,129 A | 3/1999 | Spurgeon |
| 5,796,841 A | 8/1998 | Cordery | 5,890,152 A | 3/1999 | Rapaport |
| 5,797,128 A | 8/1998 | Birnbaum | 5,892,824 A | 4/1999 | Bentson |
| 5,799,083 A | 8/1998 | Brothers | 5,892,838 A | 4/1999 | Brady |
| 5,799,086 A | 8/1998 | Sudia | 5,892,900 A | 4/1999 | Ginter |
| 5,799,087 A | 8/1998 | Rosen | 5,892,902 A | 4/1999 | Clark |
| 5,799,088 A | 8/1998 | Raike | 5,897,616 A | 4/1999 | Kanevsky |
| 5,802,199 A | 9/1998 | Pare | 5,898,154 A | 4/1999 | Rosen |
| 5,805,719 A | 9/1998 | Pare | 5,898,830 A | 4/1999 | Wesinger |
| 5,805,803 A | 9/1998 | Birrell | 5,899,998 A | 5/1999 | McGauley |
| 5,812,398 A | 9/1998 | Nielsen | 5,901,229 A | 5/1999 | Fujisaki |
| 5,812,668 A | 9/1998 | Weber | 5,901,246 A | 5/1999 | Hoffberg |
| 5,812,670 A | 9/1998 | Micali | 5,903,651 A | 5/1999 | Kocher |
| 5,815,252 A | 9/1998 | Price-Francis | 5,903,880 A | 5/1999 | Biffar |
| 5,815,577 A | 9/1998 | Clark | 5,903,889 A | 5/1999 | de la Huerga |
| 5,815,657 A | 9/1998 | Williams | 5,905,505 A | 5/1999 | Lesk |
| 5,819,289 A | 10/1998 | Sanford | 5,905,800 A | 5/1999 | Moskowitz |
| 5,822,432 A | 10/1998 | Moskowitz | 5,907,149 A | 5/1999 | Marckini |
| 5,822,436 A | 10/1998 | Rhoads | 5,909,493 A | 6/1999 | Motoyama |
| 5,825,871 A | 10/1998 | Mark | 5,910,988 A | 6/1999 | Ballard |
| 5,825,880 A | 10/1998 | Sudia | 5,911,132 A | 6/1999 | Sloane |
| 5,826,014 A | 10/1998 | Coley | 5,911,143 A | 6/1999 | Deinhart |
| 5,826,029 A | 10/1998 | Gore | 5,911,687 A | 6/1999 | Sato |
| 5,828,751 A | 10/1998 | Walker | 5,912,818 A | 6/1999 | McGrady |
| 5,828,840 A | 10/1998 | Cowan | 5,912,974 A | 6/1999 | Holloway |
| 5,832,089 A | 11/1998 | Kravitz | 5,913,025 A | 6/1999 | Higley |
| 5,832,119 A | 11/1998 | Rhoads | 5,913,196 A | 6/1999 | Talmor |
| 5,832,450 A | 11/1998 | Myers | 5,915,008 A | 6/1999 | Dulman |
| 5,832,464 A | 11/1998 | Houvener | 5,915,018 A | 6/1999 | Aucsmith |
| 5,832,488 A | 11/1998 | Eberhardt | 5,915,027 A | 6/1999 | Cox |
| 5,835,726 A | 11/1998 | Schwed | 5,915,087 A | 6/1999 | Hammond |
| 5,838,812 A | 11/1998 | Pare | 5,915,093 A | 6/1999 | Berlin |
| 5,839,119 A | 11/1998 | Krsul | 5,915,240 A | 6/1999 | Karpf |
| 5,841,122 A | 11/1998 | Kirchhoff | 5,915,973 A | 6/1999 | Hoehn-Saric |
| 5,841,865 A | 11/1998 | Sudia | 5,918,227 A | 6/1999 | Polnerow |
| 5,841,886 A | 11/1998 | Rhoads | 5,920,058 A | 7/1999 | Weber |
| 5,841,907 A | 11/1998 | Javidi | 5,920,384 A | 7/1999 | Borza |
| 5,841,978 A | 11/1998 | Rhoads | 5,920,477 A | 7/1999 | Hoffberg |
| 5,844,244 A | 12/1998 | Graf | 5,920,628 A | 7/1999 | Indeck |
| 5,845,253 A | 12/1998 | Rensimer | 5,920,629 A | 7/1999 | Rosen |
| 5,845,267 A | 12/1998 | Ronen | 5,920,630 A | 7/1999 | Wertheimer |
| 5,848,155 A | 12/1998 | Cox | 5,923,763 A | 7/1999 | Walker |
| 5,848,231 A | 12/1998 | Teitelbaum | 5,924,074 A | 7/1999 | Evans |
| 5,850,442 A | 12/1998 | Muftic | 5,925,126 A | 7/1999 | Hsieh |
| 5,850,446 A | 12/1998 | Berger | 5,926,548 A | 7/1999 | Okamoto |
| 5,850,451 A | 12/1998 | Sudia | 5,928,333 A | 7/1999 | Landfield |
| 5,850,481 A | 12/1998 | Rhoads | 5,930,369 A | 7/1999 | Cox |
| 5,857,022 A | 1/1999 | Sudia | 5,930,759 A | 7/1999 | Moore |

| | | | | | | |
|---|---|---|---|---|---|---|
| 5,930,777 A | 7/1999 | Barber | | 5,991,877 A | 11/1999 | Luckenbaugh |
| 5,933,498 A | 8/1999 | Schneck | | 5,991,878 A | 11/1999 | McDonough |
| 5,933,515 A | 8/1999 | Pu | | 5,995,625 A | 11/1999 | Sudia |
| 5,933,809 A | 8/1999 | Hunt | | 5,995,630 A | 11/1999 | Borza |
| 5,935,071 A | 8/1999 | Schneider | | 5,995,943 A | 11/1999 | Bull |
| 5,937,066 A * | 8/1999 | Gennaro et al. ............ 380/286 | | 5,996,076 A | 11/1999 | Rowney |
| 5,937,068 A | 8/1999 | Audebert | | 5,999,095 A | 12/1999 | Earl |
| 5,937,394 A | 8/1999 | Wong | | 5,999,629 A | 12/1999 | Heer |
| 5,943,422 A | 8/1999 | Van Wie | | 5,999,637 A | 12/1999 | Toyoda |
| 5,943,423 A | 8/1999 | Muftic | | 5,999,919 A | 12/1999 | Jarecki |
| 5,943,424 A | 8/1999 | Berger | | 5,999,973 A | 12/1999 | Glitho |
| 5,944,823 A | 8/1999 | Jade | | 6,002,756 A | 12/1999 | Lo |
| 5,946,414 A | 8/1999 | Cass | | 6,002,767 A | 12/1999 | Kramer |
| 5,946,669 A | 8/1999 | Polk | | 6,002,770 A | 12/1999 | Tomko |
| 5,948,136 A | 9/1999 | Smyers | | 6,002,772 A | 12/1999 | Saito |
| 5,949,045 A | 9/1999 | Ezawa | | 6,003,084 A | 12/1999 | Green |
| 5,949,046 A | 9/1999 | Kenneth | | 6,003,135 A | 12/1999 | Bialick |
| 5,949,866 A | 9/1999 | Coiera | | 6,003,765 A | 12/1999 | Okamoto |
| 5,949,876 A | 9/1999 | Ginter | | 6,004,276 A | 12/1999 | Wright |
| 5,949,877 A | 9/1999 | Traw | | 6,005,859 A | 12/1999 | Harvell |
| 5,949,879 A | 9/1999 | Berson | | 6,005,939 A | 12/1999 | Fortenberry |
| 5,949,881 A | 9/1999 | Davis | | 6,005,943 A | 12/1999 | Cohen |
| 5,949,882 A | 9/1999 | Angelo | | 6,006,328 A | 12/1999 | Drake |
| 5,949,885 A | 9/1999 | Leighton | | 6,006,332 A | 12/1999 | Rabne |
| 5,950,195 A | 9/1999 | Stockwell | | 6,009,177 A | 12/1999 | Sudia |
| 5,951,055 A | 9/1999 | Mowry | | 6,009,430 A | 12/1999 | Joseph |
| 5,952,638 A | 9/1999 | Demers | | 6,009,475 A | 12/1999 | Shrader |
| 5,952,641 A | 9/1999 | Korshun | | 6,009,526 A | 12/1999 | Choi |
| 5,953,419 A | 9/1999 | Lohstroh | | 6,011,858 A | 1/2000 | Stock |
| 5,954,583 A | 9/1999 | Green | | 6,012,035 A | 1/2000 | Freeman |
| 5,956,400 A | 9/1999 | Chaum | | 6,012,039 A | 1/2000 | Hoffman |
| 5,956,403 A * | 9/1999 | Lipner et al. ............ 380/286 | | 6,012,049 A | 1/2000 | Kawan |
| 5,956,408 A | 9/1999 | Arnold | | 6,012,088 A | 1/2000 | Li |
| 5,958,016 A | 9/1999 | Chang | | 6,014,666 A | 1/2000 | Helland |
| 5,958,050 A | 9/1999 | Griffin | | 6,016,318 A | 1/2000 | Tomoike |
| 5,960,083 A | 9/1999 | Micali | | 6,016,476 A | 1/2000 | Maes |
| 5,960,177 A | 9/1999 | Tanno | | 6,016,484 A | 1/2000 | Williams |
| 5,963,648 A | 10/1999 | Rosen | | 6,018,724 A | 1/2000 | Arent |
| 5,963,657 A | 10/1999 | Bowker | | 6,018,739 A | 1/2000 | McCoy |
| 5,963,908 A | 10/1999 | Chadha | | 6,018,801 A | 1/2000 | Palage |
| 5,963,924 A | 10/1999 | Williams | | 6,021,202 A * | 2/2000 | Anderson et al. ............ 705/54 |
| 5,966,446 A | 10/1999 | Davis | | 6,021,393 A | 2/2000 | Honda |
| 5,968,176 A | 10/1999 | Nessett | | 6,021,399 A | 2/2000 | Demers |
| 5,970,143 A | 10/1999 | Schneier | | 6,021,491 A | 2/2000 | Renaud |
| 5,974,146 A | 10/1999 | Randle | | 6,021,497 A | 2/2000 | Bouthillier |
| 5,974,389 A | 10/1999 | Clark | | 6,023,762 A | 2/2000 | Dean |
| 5,974,548 A | 10/1999 | Adams | | 6,023,765 A | 2/2000 | Kuhn |
| 5,978,475 A | 11/1999 | Schneier | | 6,026,163 A | 2/2000 | Micali |
| 5,978,494 A | 11/1999 | Zhang | | 6,026,166 A | 2/2000 | LeBourgeois |
| 5,978,840 A | 11/1999 | Nguyen | | 6,026,167 A | 2/2000 | Aziz |
| 5,978,918 A | 11/1999 | Scholnick | | 6,026,193 A | 2/2000 | Rhoads |
| 5,979,773 A | 11/1999 | Findley | | 6,026,379 A | 2/2000 | Haller |
| 5,982,520 A | 11/1999 | Weiser | | 6,026,490 A | 2/2000 | Johns-Vano |
| 5,982,891 A * | 11/1999 | Ginter et al. ............ 705/54 | | 6,028,932 A | 2/2000 | Park |
| 5,982,894 A | 11/1999 | McCalley | | 6,028,933 A | 2/2000 | Heer |
| 5,983,208 A | 11/1999 | Haller | | 6,028,936 A | 2/2000 | Hillis |
| 5,983,350 A | 11/1999 | Minear | | 6,028,937 A | 2/2000 | Tatebayashi |
| 5,984,366 A | 11/1999 | Priddy | | 6,028,939 A | 2/2000 | Yin |
| 5,986,746 A | 11/1999 | Metz | | 6,029,067 A | 2/2000 | Pfundstein |
| 5,987,132 A | 11/1999 | Rowney | | 6,029,150 A | 2/2000 | Kravitz |
| 5,987,140 A | 11/1999 | Rowney | | 6,029,151 A | 2/2000 | Nikander |
| 5,987,153 A | 11/1999 | Chan | | 6,029,160 A | 2/2000 | Cabrera |
| 5,987,155 A | 11/1999 | Dunn | | 6,029,195 A | 2/2000 | Herz |
| 5,987,440 A | 11/1999 | O'Neil | | 6,029,245 A | 2/2000 | Scanlan |
| 5,987,459 A | 11/1999 | Swanson | | 6,029,247 A | 2/2000 | Ferguson |
| 5,991,399 A | 11/1999 | Graunke | | 6,031,910 A | 2/2000 | Deindl |
| 5,991,406 A * | 11/1999 | Lipner et al. ............ 380/286 | | 6,031,913 A | 2/2000 | Hassan |
| 5,991,408 A | 11/1999 | Pearson | | 6,031,914 A | 2/2000 | Tewfik |
| 5,991,429 A | 11/1999 | Coffin | | 6,032,118 A | 2/2000 | Tello et al. |
| 5,991,431 A | 11/1999 | Borza | | 6,034,605 A | 3/2000 | March |
| 5,991,519 A | 11/1999 | Benhammou | | 6,034,618 A | 3/2000 | Tatebayashi |
| 5,991,731 A | 11/1999 | Colon | | 6,035,041 A | 3/2000 | Frankel |
| 5,991,758 A | 11/1999 | Ellard | | 6,035,276 A | 3/2000 | Newman |

| Patent | Date | Name | Patent | Date | Name |
|---|---|---|---|---|---|
| 6,035,398 A | 3/2000 | Bjorn | 6,055,512 A | 4/2000 | Dean |
| 6,035,402 A | 3/2000 | Vaeth | 6,055,536 A | 4/2000 | Shimakawa |
| 6,035,406 A | 3/2000 | Moussa | 6,055,575 A | 4/2000 | Paulsen |
| 6,037,870 A | 3/2000 | Alessandro | 6,055,637 A | 4/2000 | Hudson |
| 6,038,315 A | 3/2000 | Strait | 6,055,639 A | 4/2000 | Schanze |
| 6,038,316 A | 3/2000 | Dwork | 6,056,197 A | 5/2000 | Hara |
| 6,038,322 A | 3/2000 | Harkins | 6,056,199 A | 5/2000 | Wiklof |
| 6,038,337 A | 3/2000 | Lawrence | 6,057,872 A | 5/2000 | Candalore |
| 6,038,560 A | 3/2000 | Wical | 6,058,187 A | 5/2000 | Chen |
| 6,038,563 A | 3/2000 | Bapat | 6,058,188 A | 5/2000 | Chandersekaran |
| 6,038,581 A | 3/2000 | Aoki | 6,058,189 A | 5/2000 | McGough |
| 6,038,665 A | 3/2000 | Bolt | 6,058,193 A | 5/2000 | Cordery |
| 6,038,666 A | 3/2000 | Hsu | 6,058,303 A | 5/2000 | Astrom |
| 6,040,783 A | 3/2000 | Houvener | 6,058,381 A | 5/2000 | Nelson |
| 6,041,122 A | 3/2000 | Graunke | 6,058,383 A | 5/2000 | Narasimhalu |
| 6,041,123 A | 3/2000 | Colvin | 6,061,448 A | 5/2000 | Smith |
| 6,041,349 A | 3/2000 | Sugauchi | 6,061,451 A | 5/2000 | Muratani |
| 6,041,355 A | 3/2000 | Toga | 6,061,454 A | 5/2000 | Malik |
| 6,041,357 A | 3/2000 | Kunzelman | 6,061,665 A | 5/2000 | Bahreman |
| 6,041,408 A | 3/2000 | Nishioka | 6,061,692 A | 5/2000 | Thomas |
| 6,041,410 A | 3/2000 | Hsu | 6,061,729 A | 5/2000 | Nightingale |
| 6,041,411 A | 3/2000 | Wyatt | 6,061,789 A | 5/2000 | Hauser |
| 6,041,412 A | 3/2000 | Timson | 6,061,790 A | 5/2000 | Bodnar |
| 6,042,005 A | 3/2000 | Basile | 6,061,791 A | 5/2000 | Moreau |
| 6,044,131 A | 3/2000 | McEvoy | 6,061,792 A | 5/2000 | Simon |
| 6,044,155 A | 3/2000 | Thomlinson | 6,061,794 A | 5/2000 | Angelo |
| 6,044,157 A | 3/2000 | Uesaka | 6,061,796 A | 5/2000 | Chen |
| 6,044,205 A | 3/2000 | Reed | 6,061,797 A | 5/2000 | Jade |
| 6,044,349 A | 3/2000 | Tolopka | 6,061,798 A | 5/2000 | Coley |
| 6,044,350 A | 3/2000 | Weiant | 6,061,799 A | 5/2000 | Eldridge |
| 6,044,388 A | 3/2000 | DeBellis | 6,064,723 A | 5/2000 | Cohn |
| 6,044,401 A | 3/2000 | Harvey | 6,064,737 A | 5/2000 | Rhoads |
| 6,044,462 A | 3/2000 | Zubeldia | 6,064,738 A | 5/2000 | Fridrich |
| 6,044,463 A | 3/2000 | Kanda | 6,064,740 A | 5/2000 | Curiger |
| 6,044,464 A | 3/2000 | Shamir | 6,064,741 A | 5/2000 | Horn |
| 6,044,466 A | 3/2000 | Anand | 6,064,751 A | 5/2000 | Smithies |
| 6,044,468 A | 3/2000 | Osmond | 6,064,764 A | 5/2000 | Bhaskaran |
| 6,045,039 A | 4/2000 | Stinson | 6,064,878 A | 5/2000 | Denker |
| 6,047,051 A | 4/2000 | Ginzboorg | 6,064,968 A | 5/2000 | Schanz |
| 6,047,066 A | 4/2000 | Brown | 6,064,977 A | 5/2000 | Haverstock |
| 6,047,067 A | 4/2000 | Rosen | 6,065,008 A | 5/2000 | Simon |
| 6,047,072 A | 4/2000 | Field | 6,065,119 A | 5/2000 | Sandford |
| 6,047,242 A | 4/2000 | Benson | 6,065,675 A | 5/2000 | Teicher |
| 6,047,268 A | 4/2000 | Bartoli | 6,067,466 A | 5/2000 | Selker |
| 6,047,269 A | 4/2000 | Biffar | 6,067,620 A | 5/2000 | Holden |
| 6,047,322 A | 4/2000 | Vaid | 6,068,184 A | 5/2000 | Barnett |
| 6,047,325 A | 4/2000 | Jain | 6,069,647 A | 5/2000 | Sullivan |
| 6,047,374 A | 4/2000 | Barton | 6,069,914 A | 5/2000 | Cox |
| 6,047,887 A | 4/2000 | Rosen | 6,069,952 A | 5/2000 | Saito |
| 6,049,610 A | 4/2000 | Crandall | 6,069,954 A | 5/2000 | Moreau |
| 6,049,612 A | 4/2000 | Fielder | 6,069,955 A | 5/2000 | Coppersmith |
| 6,049,613 A | 4/2000 | Jakobsson | 6,069,969 A | 5/2000 | Keagy |
| 6,049,627 A | 4/2000 | Becker | 6,069,970 A | 5/2000 | Salatino |
| 6,049,671 A | 4/2000 | Slivka | 6,070,141 A | 5/2000 | Houvener |
| 6,049,785 A | 4/2000 | Gifford | 6,070,239 A | 5/2000 | McManis |
| 6,049,786 A | 4/2000 | Smorodinsky | 6,072,870 A | 6/2000 | Nguyen |
| 6,049,787 A | 4/2000 | Takahashi | 6,072,874 A | 6/2000 | Shin |
| 6,049,838 A | 4/2000 | Miller | 6,072,876 A | 6/2000 | Obata |
| 6,049,872 A | 4/2000 | Reiter | 6,072,894 A | 6/2000 | Payne |
| 6,049,874 A | 4/2000 | McClain | 6,073,106 A | 6/2000 | Rozen |
| 6,049,875 A | 4/2000 | Suzuki | 6,073,125 A | 6/2000 | Cordery |
| 6,052,466 A | 4/2000 | Wright | 6,073,160 A | 6/2000 | Grantham |
| 6,052,467 A | 4/2000 | Brands | 6,073,172 A | 6/2000 | Frailong |
| 6,052,468 A | 4/2000 | Hillhouse | 6,073,234 A | 6/2000 | Kigo |
| 6,052,469 A | 4/2000 | Johnson | 6,073,236 A | 6/2000 | Kusakabe |
| 6,052,688 A | 4/2000 | Thorsen | 6,073,237 A | 6/2000 | Ellison |
| 6,052,780 A | 4/2000 | Glover | 6,073,238 A | 6/2000 | Drupsteen |
| 6,052,788 A | 4/2000 | Wesinger | 6,073,240 A | 6/2000 | Kurtzberg |
| 6,055,314 A | 4/2000 | Spies | 6,073,242 A | 6/2000 | Hardy |
| 6,055,321 A | 4/2000 | Numao | 6,075,455 A | 6/2000 | DiMaria |
| 6,055,494 A | 4/2000 | Friedman | 6,075,852 A | 6/2000 | Ashworth |
| 6,055,506 A | 4/2000 | Frasca | 6,075,854 A | 6/2000 | Copley |
| 6,055,508 A | 4/2000 | Naor | 6,075,860 A | 6/2000 | Ketcham |

| | | | |
|---|---|---|---|
| 6,075,861 A | 6/2000 | Miller | |
| 6,075,864 A | 6/2000 | Batten | |
| 6,075,865 A | 6/2000 | Scheidt | |
| 6,076,066 A | 6/2000 | DiRienzo | |
| 6,076,077 A | 6/2000 | Saito | |
| 6,076,078 A | 6/2000 | Camp | |
| 6,076,162 A | 6/2000 | Deindl | |
| 6,076,163 A | 6/2000 | Hoffstein | |
| 6,076,164 A | 6/2000 | Tanaka | |
| 6,076,166 A | 6/2000 | Moshfeghi | |
| 6,076,167 A | 6/2000 | Borza | |
| 6,078,265 A | 6/2000 | Bonder | |
| 6,078,586 A | 6/2000 | Dugan | |
| 6,078,663 A | 6/2000 | Yamamoto | |
| 6,078,665 A | 6/2000 | Anderson | |
| 6,078,667 A | 6/2000 | Johnson | |
| 6,078,909 A | 6/2000 | Knutson | |
| 6,078,946 A | 6/2000 | Johnson | |
| 6,079,018 A | 6/2000 | Hardy | |
| 6,079,020 A | 6/2000 | Liu | |
| 6,079,021 A | 6/2000 | Abadi | |
| 6,079,047 A | 6/2000 | Cotugno | |
| 6,079,621 A | 6/2000 | Vardanyan | |
| 6,081,199 A | 6/2000 | Hogl | |
| 6,081,533 A | 6/2000 | Laubach | |
| 6,081,597 A | 6/2000 | Hoffstein | |
| 6,081,598 A | 6/2000 | Dai | |
| 6,081,610 A | 6/2000 | Dwork | |
| 6,081,750 A | 6/2000 | Hoffberg | |
| 6,081,790 A | 6/2000 | Rosen | |
| 6,081,793 A | 6/2000 | Challener | |
| 6,081,893 A | 6/2000 | Frawrock | |
| 6,081,900 A | 6/2000 | Subramanian | |
| 6,082,776 A | 7/2000 | Feinberg | |
| 6,092,724 A | 7/2000 | Bouthillier | |
| 6,098,056 A * | 8/2000 | Rusnak et al. | 705/75 |
| 6,108,644 A | 8/2000 | Goldschlag | |
| 6,108,787 A | 8/2000 | Anderson | |
| 6,112,181 A | 8/2000 | Shear | |
| 6,118,874 A | 9/2000 | Okamoto | |
| 6,119,229 A | 9/2000 | Martinez | |
| 6,125,186 A | 9/2000 | Saito | |
| 6,131,090 A | 10/2000 | Basso | |
| 6,134,326 A | 10/2000 | Micali | |
| 6,134,328 A * | 10/2000 | Cordery et al. | 380/55 |
| 6,137,884 A | 10/2000 | Micali | |
| 6,138,119 A | 10/2000 | Hall | |
| 6,141,750 A | 10/2000 | Micali | |
| 6,141,755 A | 10/2000 | Dowd | |
| 6,141,758 A | 10/2000 | Benantar | |
| 6,145,079 A | 11/2000 | Mitty | |
| 6,148,338 A | 11/2000 | Lachelt | |
| 6,148,342 A | 11/2000 | Ho | |
| 6,149,440 A | 11/2000 | Clark | |
| 6,151,395 A | 11/2000 | Harkins | |
| 6,157,721 A | 12/2000 | Shear | |
| 6,157,914 A | 12/2000 | Seto | |
| 6,158,010 A | 12/2000 | Moriconi | |
| 6,161,139 A | 12/2000 | Win | |
| 6,161,181 A | 12/2000 | Haynes | |
| 6,175,626 B1 | 1/2001 | Aucsmith | |
| 6,192,472 B1 | 2/2001 | Garay | |
| 6,192,473 B1 | 2/2001 | Ryan | |
| 6,192,476 B1 | 2/2001 | Gong | |
| 6,236,727 B1 | 5/2001 | Ciacelli | |
| 6,363,154 B1 | 3/2002 | Peyravian | |
| 6,529,885 B1 | 3/2003 | Johnson | |
| 6,567,850 B1 | 5/2003 | Freishtat | |
| 6,640,304 B2 * | 10/2003 | Ginter et al. | 713/193 |

OTHER PUBLICATIONS

S. Buckovich, H. Rippen, and M. Rozen, "Driving Toward Guiding Principles: A Goal for Privacy, Confidentiality, and Security of Health Information", J. Am. Med. Inform. Assoc. 6: 122-133 (1999).
Common Markup for web Micropayment Systems, http://www.3.org/TR/1999/WD-Micropayment-Markup-19990609 (Jun. 9, 1999).
Common Markup for micropayment per fee links, http://www.w3.org/TR/1999/WD-Micropayment-Markup-19990825 (Aug. 25, 1999).
R. Cushman, "Serious Technology Assessment for Health Care Information Technology", J. Am. Med. Inform. Assoc. 4: 259-265 (1997).
Digital Millenium Copyright Act, 17 U.S.C. §§1201 et seq.
J. Halamka, P. Szolovits, D. Rind, and C. Safran, "A WWW Implementation of National Recommendations for Protecting Electronic Health Information", J. Am. Med. Inform. Assoc. 4: 458-464 (1997).
Health Insurance Portability and Accountability Act of 1996, Pub. L. 104-191, 110 Stat. 1936 et seq. (Aug. 21, 1996).
C. McDonald, "The Barriers to Electronic Medical Record Systems and How to Overcome Them", J. Am. Med. Inform. Assoc. 4: 213-221 (1997).
M. Olivia, Distributing Intellectual Property: a Model of Microtransactions Based Upon Metadata and Digital Signatures, http://oliva.modlang.denison.edu/olivia/RFC/09/.
R. Rivest and A. Shamir, "PayWorld and MicroMint: Two Simple Micropayment Schemes" (May 7, 1996); Micro Payment transfer Protocol (MPTP) Version 0.1 (Nov. 22, 1995) et seq., http://www.w3.org/pub/WWW/TR/WD-mptp.
P. Tang, "An AMIA Perspective on Proposed Regulation of Privacy of Health Information", J. Am. Med. Inform. Assoc. 7: 205-207 (2000).
United States Department of Health and Human Services, Standards for the Privacy of Individually Identifiable Health Information, Final Rule, 45 CFR Parts 160 and 164, reprinted at http://aspe.hhs.gov/adminsimp/final/PvcTx01.htm, also available at 65 Federal Register 82462 et seq. (Dec. 28, 2000).
United States Department of Health and Human Services, Standards for the Privacy of Individually Identifiable Health Information, Proposed Rule, 45 CFR Parts 160 and 164, 64 Federal Register 59918 et seq., (Nov. 3, 1999).
J. Wight and J. Robillard (Philsar Semiconductor), "Adding Security to Portable Designs", Portable Design, (Mar. 16-20, 2000).
S. Dawson, Trusted Interoperation of Healthcare Information (TIHI) reprinted at http://www-db.stanford.edu/pub/gio/TIHI/TIHI.html.
D. Liu, K. Law, and G. Wiederhold, CHAOS: An Active Security Mediation System.
G. Wiederhold, Bioinformatics: Converting Data to Knowledge reprinted at http://www-db.stanford.edu/pub/gio/2000/NCR2001.htm.
G. Wiederhold and M. Bilello, A Security Mediator for Health Care Information.
G. Wiederhold and M. Bilello, Protecting Inappropriate Release of Data from Realistic Databases reprinted at http://www-db.stanford.edu/pub/gio/TIHI/DEXAgio.html.
US 6,009,171, 12/1999, Ciacelli (withdrawn)

* cited by examiner

INFORMATION RECORD INFRASTRUCTURE, SYSTEM AND METHOD

FIELD OF THE INVENTION

The present invention relates to the field of information records, repositories, systems and methods for the creation, use, processing, maintenance, transmission, querying and protection thereof.

BACKGROUND OF THE INVENTION

Computerized records and database are employed in many industries. Often, the information is made available subject to usage rights limitations. For example, copyright information is generally controlled by the copyright owner, such that copying is controlled or prohibited after publication. In a digital environment, each transmission of the content results in a form of copying, such that a copyright owner cannot impose a strict prohibition on all forms of copying while promoting digital use of the content. Thus, the publisher or content owner seeks to apply rules that provide appropriate compensation.

In other instances, the issue is not content, but rather security and privacy. In these cases, the rules limit access based on an authorization, which may be express or implied. Medical and legal records are examples of this form of content limitation.

Conceptually, implementation of an economic permission and security permission based access control systems are similar. In fact, security based access control systems often include logs and audit trails, which are similar to the accounting databases associated with economic permission systems. Thus, many issues raised by these systems are similar.

Medical Records

The art of medical record keeping has developed over centuries of medical practice to provide an accurate account of a patient's medical history. Record keeping in medical practice was developed to help physicians, and other healthcare providers, track and link individual "occurrences" between a patient and a healthcare provider. Each physician/patient encounter may result in a record including notes on the purpose of the visit, the results of physician's examination of the patient, and a record of any drugs prescribed by the physician. If, for example, the patient were referred to another clinic for additional testing, such as a blood analysis, this would form a separate medical encounter, which would also generate information for the medical record.

The accuracy of the medical record is of the utmost importance. The medical record describes the patient's medical history, which may be of critical importance in providing future healthcare to the patient. Further, the medical record may also be used as a legal document, as a research tool and to provide information to insurance companies or third party reimbursors.

Over the years, paper medical records have evolved from individual practitioners' informal journals to the current multi-author, medical/legal documents. These paper records serve as the information system on which modern medical practice is based. While the paper-based medical record system has functioned well over many decades of use, it has several shortcomings. First, while a paper-based record system can adequately support individual patient-physician encounters, it fails to serve as a source of pooled data for large-scale analysis. While the medical data in the paper-based records is substantial, the ability to adequately index, store and retrieve information from the paper-based mechanisms prevents efficient analysis of the data. Thus, paper medical records could be a rich source of information for generating new knowledge about patient care, if only their data could be accessed on a large scale. Second, each portion of the paper-based record is generated and kept at the site of the medical service. Hence, the total record may be fragmented among many sites. Consequently, access by off-site physicians is less than optimal. The inability to access a complete medical record in a short period of time presents problems both for individual care and group care of patients. Because of the shortcomings of the paper-based record, the electronic medical record (or "EMR") has been investigated for a number of years. An electronic medical record may be stored and retrieved electronically through a computer.

Clinical information as expressed by health care personnel is typically provided in natural language, e.g., in English. While phrases in natural language are convenient in interpersonal communication, the same typically does not apply to computerized applications such as automated quality assurance, clinical decision support, patient management, outcome studies, administration, research and literature searching. Even where clinical data is available in electronic or computer-readable form, the data may remain inaccessible to computerized systems because of its form as narrative text. Thus, while medical records may be maintained in electronic form, significant efforts are necessary in order to make the information available for automated analysis.

For computerized applications, methods and systems have been developed for producing standardized, encoded representations of clinical information from natural-language sources such as findings from examinations, medical history, progress notes, and discharge summaries. Special-purpose techniques have been used in different domains, e.g., general and specialized pathology, radiology, and surgery discharge reports.

Medical information poses significant challenges to knowledge management systems. Medical information presently includes multimedia file types, including numeric data, text, scanned text images, scanned graphic images, sound (e.g., phonocardiography and dictation), high resolution images (radiology) and video (ultrasonic imaging and fluoroscopy). The medical records for an individual may, over time, grow to multiple megabytes or even gigabytes of data, and advanced medical techniques promise to increase the available data. These records come from a number of different medical service providers, and may be stored in geographically disparate locations. Often, a new medical service provider will seek to review all appropriate previous medical records for a patient. Further, in third party reimbursement situations, the third party indemnitor will seek to review records in connection with billed services.

On the other hand, medical records include data that is intensely personal, including personal data such as sexual habits, drug abuse, psychological disorders, family histories, genetics, terminal diseases, or other injuries, and the like. Thus, while there are legitimate reasons for transmitting medical information files, such transmission must be limited to appropriate circumstances and to authorized recipients.

In today's practice environment, the inability of healthcare providers, administrators, insurers, researchers and governmental agencies to rapidly access and/or extract information from paper-based medical records represents a serious limitation with significant scientific and economic ramifications. Electronic medical record systems are expected to improve healthcare delivery by enhancing case management capabilities, and by leading to clinical practice research databases that provide valuable information on patient outcomes and clinical effectiveness.

While there have been attempts to develop computer database architectures capable of storing and retrieving medical record information which reconcile physicians' desires for maintaining a format of unstructured medical information with database requirements for highly structured data storage, these systems fail to provide an infrastructure for the efficient transmission, use and security protection of the data.

Some approaches have been based on the development of categorical data structures and descriptive vocabularies that require translation of medical information into highly structured abstractions. This approach is problematic due to the enormous size of the overall translation task, the inability to accurately code all of the information contained within the free-text portion of the record, and the fact that normalizing data introduces additional abstraction, which may devalue its clinical worth.

Other approaches provide a full text database with a metadata header abstracting portions of the data record. However, searching this metadata may be difficult, and the existence of this metadata outside of the record itself may impair patient privacy. On the other hand, failure to index the data makes searching for a record difficult.

There has been a longstanding trend to computerize various forms of information, in order to make this information more accessible, to facilitate transmission, and to facilitate storage thereof. However, in the case of medical information, this has resulted in significant concerns for the privacy and security of the information. Indeed, while the information technically cannot be disclosed without the consent of the patient, since at least the time of Hippocrates, the medical institutions that hold this information guard it jealously. Thus, it may be difficult to obtain collaboration between medical institutions in the ongoing treatment of a patient. While there are important legitimate uses for medical data, there is also a substantial possibility for abuse of the data and the associated trust relationship between patient and medical care provider represented therein. In fact, recent federal legislative and regulatory initiatives (U.S. Department of Human Health Services) seek to regulate the creation, use, transmission and maintenance of medical information databases, and indeed may impose criminal sanctions.

The regulatory activities define mandates without defining implementing technologies nor providing funding for the burden imposed on federal, state, local and private entities.

Typically, in a hospital medical information system, information relating to patients in a database is generated and used by users having a variety of roles, including doctors of various specialties, nurses, therapists of various types, paraprofessionals, clinical laboratories, and bedside devices (which may automatically generate or receive patient information). In addition, medical information is used, but typically not generated by, pharmacies, administrators, lawyers, insurers or payors, and other parties.

Medical databases present a particular problem that has been difficult to address. On one hand, database architects seek to provide indexing of key fields of the database, allowing efficient retrieval. On the other hand, such indexes necessarily include information derived from the record. Thus, the existence of an index poses a security and privacy breach risk. One way to address this issue, as proposed in U.S. Pat. No. 5,832,450, is to avoid indexing, but rather to provide information contained only in the database record. While this preserves privacy, it makes locating a database record other than by patient identifier, or its accession identifier, very difficult.

Another method used to address this problem is the maintenance of anonymous medical records in addition to patient-specific records. Thus, a search for a record other than by patient identifier may be performed, but typically not for the treatment of the patient. Such techniques are useful in academic exercises. Often, the anonymization process is imperfect, or very costly.

One scheme for increasing the portability of medical records is to provide personal data storage devices, for example in credit card format optical storage medium. These devices, however, present a security risk, since it cannot be presumed that the patient will be able to provide consent to the use of the information when required; thus, access controls must necessarily be compromised. Further, the information carrier can be lost or destroyed.

Because of the many types of caregivers, the idea of role-based access has arisen; basically, medical professionals of different types will require access to various subsets of the medical record. For example, typically the primary care physician and certain consults will require full access.

Traditionally, medical records maintenance and upkeep have imposed a significant cost and burden. While enterprises have evolved for outsourcing of certain functions, these enterprises have not particularly represented the interests of the patient, and rather serve as agents for the medical record custodian.

One method for ensuring data security is encryption. Cryptographic systems employ secret keys to protect information. Key management systems for cryptographic keys are well known. One such system, by Entrust Technologies Limited is currently commercially available.

Media Content

One particular area of digital rights management involves the use and distribution of digital media, e.g., consumer entertainment in the form of audio, video, multimedia, and/or text. Computer software may be considered another form of media. In these systems, one significant purpose for digital distribution is to reduce the costs and increase convenience involved in communicating the information to the user. This, in turn, tends to reduce the actual or perceived cost of "consumption" of the media to the user. However, in a digital network, the content is readily replicated, and thus the owner risks loss of control and compensation. In order to retain control, the media is typically distributed in encrypted form. Alternatively, the media itself is unencrypted, but the available hardware for using the digital media requires permission for operation, in effect blocking the decoding to a usable form.

The existing systems seek to create an obligation by the recipient on behalf of the owner, to abide by the restrictions imposed. This obligation can be voluntarily or mandatory.

While on-line systems for browsing media may maintain privacy and confidentiality, on-line commercial transactions often waive privacy and confidentiality, by requiring disclosure of identity, electronic billing information, bill address, shipping address, and the association with the item being purchased. Further, databases are maintained which may then impair future privacy by associating the user's IP address or providing a browser cookie, which identify the user or associate with a prior detailed database record.

Thus, electronic commerce has the ability to eliminate the anonymity of cash. This is especially troublesome with respect to media content preferences and consumption, since these preferences and consumption were heretofore considered private.

Existing systems do not create a trust infrastructure, wherein an independent third party represents and serves as agent for the content owner, implementing a set of restrictive rules for use of the content, and interacting and servicing customers. In fact, these systems adopt a more traditional retail model, with independent resellers, or employ related entities.

In fact, the use of an intermediary, such as an Internet proxy server or payment service can protect user privacy. However, the Internet proxy cannot anonymize a direct electronic purchase transaction. Thus, existing intermediaries do not act in a representative capacity for the content owner, and do not integrate content management functions.

Personal Demographic Information

As stated above, many different electronic commerce systems have access to, and indeed maintain profiles and other information on customers. Even non-electronic retailers have adopted techniques to provide the same types of information, for example, supermarkets that provide "club cards", and otherwise may track credit/debit card purchases.

Retailers seek to gain valuable insight into their business and consumer habits and responsiveness to promotions by profiling consumers, and forming personal profiles and/or aggregate profiles from this information. Since the information often includes purchase information, the profiles are personally identifiable. Further, user profiling must be associated with the same user on an ongoing basis.

Intermediaries

In fact, the use of an intermediary, such as an Internet proxy server or payment service, can protect user privacy. However, the Internet proxy cannot anonymize a direct electronic purchase transaction, and use of an intermediary service results in a loss of rights with respect to credit card transactions.

Thus, existing intermediaries do not act in a representative capacity for the content owner, and do not integrate content management functions.

Computer Security

Computer security is currently an important issue. With the proliferation of computers and computer networks into all aspects of business and daily life—financial, medical, education, government, and communications—the concern over secure file access is growing. Using passwords is a common method of providing security. Password protection and/or personal identification numbers are employed for computer network security, automatic teller machines, telephone banking, calling cards, telephone answering services, houses, and safes. These systems generally require the knowledge of an entry code that has been selected by a user or has been preset. Preset codes are sometimes forgotten, as users have no reliable method of remembering them. Writing down the codes and storing them in close proximity to an access control device (i.e. the combination lock) results in a secure access control system with a very insecure code. Alternatively, the nuisance of trying several code variations renders the access control system more of a problem than a solution.

Password systems are known to suffer from other disadvantages. Usually, a user specifies passwords. Most users, being unsophisticated users of security systems, choose passwords that are relatively insecure, for example words that are found in a dictionary or within a personal wallet. As such, many systems protected by passwords are easily accessed through a simple (possibly automated) trial and error process.

Biometric authentication schemes, for example fingerprint, voice, iris, retina, hand, face, or other personal characteristics, may be used to identify a user. These either do not require a password or access code, or are used in conjunction with such passwords or codes, and may provide substantial system security. A biometric identification system accepts unique biometric information from a user and identifies the user by matching the information against information belonging to registered users of the system.

Though biometric authentication is a secure means of identifying a user, it is difficult to derive encryption keys from the information. In the first place, the information is different each time it is presented to a biometric information input device. Secondly, the biometric information is retrievable through, for example, extraction of latent fingerprints, and is therefore subject to "spoofing". When an encryption key is derived directly from biometric information, the extraction of latent biometric information or the interception of biometric information may allow others to derive the encryption key. Thirdly, since some biometric information is substantially unchanging, it is not well suited to encryption because once an encryption key or biometric authentication system is broken (i.e., knowledge exists to circumvent the security provided by the scheme), and its use should be discontinued; however, changing the biometric information on demand is a difficult procedure. In order to overcome this problem, key management systems exist wherein a plurality of keys are stored in a secure key database. A user authentication, such as a biometric authentication, is used to access the secure key database. Often the database is encrypted with a key that is accessible through user authentication.

Key management systems are well known. One such system, by Entrust Technologies Limited is currently commercially available. Unfortunately, current key management systems are designed for installation on a single computer and for portability between computers having a same configuration. As such, implementation of enhanced security through installation of biometric input devices is costly and greatly limits portability of key databases. Alternatively, password based protection of key databases is undesirable because of the inherent insecure nature of most user selected passwords. For example, when using Entrust® software to protect a key database, the database is portable on a smart card or on a floppy disk. The portable key database is a duplicate of the existing key database. User authentication for the portable key database is identical to that of the original key database. The implications of this are insignificant when password user authentication is employed; however, when biometric user authentication such as retinal scanning or fingerprint identification are used, the appropriate biometric identification system is required at each location wherein the portable key database is used. Unfortunately, this is often not the case. In order to avoid this problem, organizations employ password access throughout and thereby reduce overall security to facilitate portability. Alternatively, members of an organization are not permitted to travel with portable key databases and thereby have reduced mobility and are capable of performing fewer tasks while outside the office. This effectively counters many of the benefits available in the information age. Key databases, once created, should not decrypted, except during emergencies. This prevents keys from becoming vulnerable by existing in their decrypted state.

Prior Art

A number of fields of endeavor are relevant to the present invention, and exemplary prior art, incorporated herein by reference, are disclosed below. The references disclosed provide a skilled artisan with embodiments of elements of the present invention, and the teachings therein may be combined and subcombined in various manners in accordance with the present teachings. The topical headings are advisory only, and are not intended to limit the applicability of any reference.

Medical Record Systems

John D. Halamka, Peter Szolovits, David Rind, and Charles Safran, "A WWW Implementation of National Recommendations for Protecting Electronic Health Information", J. Am. Med. Inform. Assoc. 1997 4: 458-464 (expressly incorporated herein by reference).

Reid Cushman, "Serious Technology Assessment for Health Care Information Technology", J. Am. Med. Inform. Assoc. 1997 4: 259-265 (expressly incorporated herein by reference).

Suzy A. Buckovich, Helga E. Rippen, and Michael J. Rozen, "Driving Toward Guiding Principles: A Goal for Privacy, Confidentiality, and Security of Health Information", J. Am. Med. Inform. Assoc. 1999 6: 122-133 (expressly incorporated herein by reference).

Paul C. Tang, "An AMIA Perspective on Proposed Regulation of Privacy of Health Information", J. Am. Med. Inform. Assoc. 2000 7: 205-207 (expressly incorporated herein by reference).

Clement J. McDonald, "The Barriers to Electronic Medical Record Systems and How to Overcome Them", J. Am. Med. Inform. Assoc. 1997 4: 213-221 (expressly incorporated herein by reference).

U.S. Pat. No. 5,361,202 (Doue, Nov. 1, 1994, Computer display system and method for facilitating access to patient data records in a medical information system), expressly incorporated herein by reference, relates to a system and method to improve access to patient information in medical information system for a health care facility. A computer display system, and a method for such a display system, includes a displayed representation of the duration of the stay of an identified patient in the health care facility. In such a medical information system patient data is stored in data files in a database, wherein each data file in the database is comprised of a plurality of data records. A user positions a cursor on the displayed representation using an input unit and signals the computer of a desired date and time. The computer, in response to the signal determines the desired date and time from the position of the cursor and accesses a data record or records from the data file based on the desired date and time. The accessed data record or records may then be displayed. The data records may be time-stamped. In that case, the duration of the patient's stay is the time period between the earliest and latest time stamps.

U.S. Pat. No. 5,644,778 (Burks, et al., Jul. 1, 1997, Medical transaction system), expressly incorporated herein by reference, relates to a medical transaction system, which is capable of permitting a plurality of healthcare providers to communicate with a plurality of payors and financial institutions. The healthcare providers, payors, and financial institutions do not have to communicate in the same data message formats nor in the same communication protocols. Such a system facilitates not only the processing of medical claims submitted by the healthcare providers to the payors, but also permits the transfer of medical data records between healthcare providers. The system supports the processing of medical claims without requiring a centralized database or imposing a uniform claim format on the healthcare providers and payors. The preferred embodiment further includes a financial transactor that uses remittance information from the payors to generate the electronics funds transfer messages to credit and debit accounts. Additionally, the system supports a medical line of credit at financial institutions that may be used to pay portions of medical claims not covered by payors.

U.S. Pat. No. 5,832,450 (Myers, et al. Nov. 3, 1998), expressly incorporated herein by reference, provides an electronic medical record system that stores data about individual patient encounters arising from a content generator in free-form text. A header for each encounter-based record also uses text to store context information for that record. Each header comprises a plurality of attributes embodied as a field descriptor and a value, bound together as a text object. By binding the field descriptors to the values, each encounter record is complete in itself, without reference to database keys, thereby providing a self-validating record storage system. In this system, the security of the medical data is maintained, because the attribute values and the attribute descriptors are bound together as a text object, and because the values are not location dependent, the data is self-validating. Thus, templates, keys, or other lookup means employed by relational database are not required to find or interpret the data. Additional attributes may be added without a restructuring process, reducing a source of errors into the system. Access of the content and context information in the EMR system by external systems is possible without secondary tables or keys.

U.S. Pat. No. 5,546,580 (Seliger, et al., Aug. 13, 1996), expressly incorporated herein by reference, relates to a method and apparatus for coordinating concurrent updates to a medical information database, from different workstations and medical instruments. A first data value for a record is entered at a first workstation and a second data value for the record is entered at a second workstation without locking either workstation during data entry. The new data values are stored in the medical database after completion of data entry at each workstation, and a correction history is recorded. The correction history contains information as to the update of the record with the first data value and the second data value. The record is updated with the first and second data values without aborting user activities or notifying a user that an update conflict has occurred. After the new data values are stored in the medical database, all workstations containing a copy of the record are updated to reflect the current state of the record.

U.S. Pat. No. 5,832,488 (Eberhardt, Nov. 3, 1998), expressly incorporated herein by reference, relates to a computer system and method for storing medical histories using a smartcard to store data. A computer system and method is provided for programming it for storage of individual medical histories on a storage device, preferably about the size of a credit card, for adding new medical data about the individual to the device and for communicating with other computers to retrieve large data records about the individual; and for enabling a second computer to collate and sort data relating to selected medical fields from the data of such individual and from the data about other individuals transferred to the second computer.

U.S. Pat. No. 5,867,821 (Ballantyne, et al., Feb. 2, 1999), expressly incorporated herein by reference, relates to a method and apparatus for electronically accessing and distributing personal health care information and services in hospitals and homes, for the distribution and administration of medical services, entertainment services, electronic medical records, educational information, etc. to a patient's individual electronic patient care station (PCS) interconnected to a master library (ML) which stores data in digital compressed format, through a local medical information network. The patient/medical personnel interact with this medical information network through the unique PCS and receive the requested service or data from the master library. The data is then displayed either on the associated television set or video monitor or through wireless/IR communications to a peripheral personal data assistant (pen based computer technology)

The data for text, audio, and video information is all compressed digitally to facilitate distribution and only decompressed at the final stage before viewing/interaction.

U.S. Pat. No. 5,899,998 (McGauley, et al., May 4, 1999), expressly incorporated herein by reference, relates to a method and system for maintaining and updating computerized medical records. A distributed database architecture stores medical information in a self-updating system that employs point-of-service stations disposed at convenient medical service locations. Each patient carries a portable data carrier such as a smart card that contains the patient's complete medical history. Interaction between the portable data carriers and the point-of-service stations effects a virtual communication link that ties the distributed databases together without the need for online or live data connections. The point-of-service stations are also interconnected over a communications network through a switching station that likewise does not rely on online, live communication. The database system uses an object-oriented update object to distribute data that has been generated when a portable data carrier is not physically present and to automatically distribute data without the necessity of accessing a masterfile.

U.S. Pat. No. 5,903,889 (de la Huerga, et al., May 11, 1999), expressly incorporated herein by reference, relates to a system and method for translating, collecting and archiving patient records. The system retrieves, modifies, and collects data records having a plurality of formats and distributed on a plurality of databases on a computer network. The system includes means for detecting various types, relationships, and classifications of data records and modifying them accordingly to support interactive, hypertext-linked display of, and organized access to, the data records. The system further includes means to store a related set of data records on a mass storage device such as a CD-ROM to provide non-network access to the data records. Adapted for use in a hospital environment, the system facilitates access by care providers, administrators, and insurance company agents to a patient's cumulative, and possibly extensive, record.

U.S. Pat. No. 5,911,132 (Sloane, Jun. 8, 1999, Method using central epidemiological database), expressly incorporated herein by reference, relates to a system in which patient disease is diagnosed and/or treated using electronic data communications between not only the physician and his/her patient, but via the use of electronic data communications between the physician and one or more entities which can contribute to the patient's diagnosis and/or treatment, such electronic data communications including information that was previously received electronically from the patient and/or was developed as a consequence of an electronic messaging interaction that occurred between the patient and the physician. Such other entities illustratively include a medical diagnostic center and an epidemiological database computer facility that collects epidemiological transaction records from physicians, hospitals and other institutions that have medical facilities, such as schools and large businesses. The epidemiological transaction record illustratively includes various medical, personal and epidemiological data relevant to the patient and his/her present symptoms, including test results, as well as the diagnosis, if one has already been arrived at by the e-doc. The epidemiological database computer facility can correlate this information with the other epidemiological transaction records that it receives over time in order to help physicians make and/or confirm diagnoses as well as to identify and track epidemiological events and/or trends.

U.S. Pat. No. 5,911,687 (Sato, et al., Jun. 15, 1999, Wide area medical information system and method using thereof), expressly incorporated herein by reference, relates to a wide area medical information system and a method using thereof comprising a wide area network, a plurality of doctor terminals and patient terminals connected to the wide area network, and a management server including at least an electronic case record file storing clinic information for patient's and a doctor database storing data of a plurality of doctors, wherein the system searches the doctor database on the basis of patient information including the condition of the disease of a certain patient input from the patient terminal, selects the corresponding doctor, requests that the selected doctor take charge of examination and treatment for the aforementioned certain patient, registers the correspondence between the approved doctor and the aforementioned certain patient in the electronic case record file, gives the right to access the clinic information of the patient to the approved doctor, and executes the online examination and treatment via the doctor terminal and patient terminal, so that a patient existing in a wide area can receive remote examination and treatment services of high satisfaction and medical treatment related services other than examination and treatment without depending on the location.

U.S. Pat. No. 5,915,240 (Karpf, Jun. 22, 1999), expressly incorporated herein by reference, relates to a computer system and method for accessing medical information over a network. The system partitions the functioning of the system between a client and server program optimized in a manner to assure synchronization of the master medical information databases on the servers with the local medical information database on the client, minimize the use of network resources, and allow new types of medical information to be easily included in the system. A server site on the network maintains a description of its medical information, as well as the most current and up-to-date medical reference information. The client program maintains a local database that is automatically synchronized over the network with revisions and new medical information, and provides a user with an interface to fully review the information in the database. The system also uses a context-sensitive call facility so that users of the Medical Lookup Reference program can easily get further expert assistance about the medical topic. The call feature uses the network connection to establish a conversation between the user and a person at a help site specified by the type of medical information they are currently referencing. Once a connection is established, the system allows the user to engage in a conversation with the person at the help site, and a record of the conversation can be saved in a database for auditing purposes.

U.S. Pat. No. 5,924,074 (Evans, Jul. 13, 1999), expressly incorporated herein by reference, relates to an electronic medical records system. The system captures patient data, such as patient complaints, lab orders, medications, diagnoses, and procedures, at its source at the time of entry using a graphical user interface having touch screens. Using pen-based portable computers with wireless connections to a computer network, authorized healthcare providers can access, analyze, update and electronically annotate patient data even while other providers are using the same patient record. The system likewise permits instant, sophisticated analysis of patient data to identify relationships among the data considered. Moreover, the system includes the capability to access reference databases for consultation regarding allergies, medication interactions and practice guidelines. The system also includes the capability to incorporate legacy data, such as paper files and mainframe data, for a patient.

U.S. Pat. No. 5,933,809 (Hunt, et al., Aug. 3, 1999), expressly incorporated herein by reference, relates to computer software for processing medical billing record information. Hospital or individual doctor Medicare billing records are processed using computer software. The software contains at least one set of instructions for receiving, converting, sorting and storing input information from the pre-existing medical billing records into a form suitable for processing. The software contains at least one set of instructions for processing the input medical billing record information, preferably to identify potential Medicare "72 hour billing rule" violations. This processing is preferably performed by comparing each input medical billing record containing dates of medical inpatient admission and discharge to each input medical billing record containing a date of medical outpatient service. The inpatient and outpatient billing records are first compared to determine if they contain matching patient identification codes to identify all the records originating from the same patient. If matching patient identification codes are found the inpatient and outpatient billing records are further compared to determine if the date of outpatient service fell within a preselected time period, preferably 72 hours, prior to the date of inpatient admission. If so, the matching inpatient and outpatient billing records are distinguished and stored separately for further processing. If not, the matching inpatient and outpatient billing records are compared to determine if the date of outpatient service fell between the inpatient admission and discharge dates. If this is the case, the matching inpatient and outpatient billing records are again distinguished and stored separately for further processing. If not, the program proceeds to the next set of billing records to repeat the sequence.

U.S. Pat. No. 5,974,389 (Clark, et al., Oct. 26, 1999, Medical record management system and process with improved workflow features) relates to a patient medical record system includes a number of caregiver computers, and a patient record database with patient data coupled to the caregiver computers selectively providing access to the patient data from one of the caregiver computers responsive to a predetermined set of access rules. The predetermined set of rules includes a rule that access to a predetermined portion of the patient data by a first caregiver must be terminated before access to the same predetermined portion by a second caregiver is allowed.

U.S. Pat. No. 5,991,758 (Ellard, Nov. 23, 1999), expressly incorporated herein by reference, relates to a system and method for indexing information about entities from different information sources. A system and method for indexing a data record from an information source into a database, the database containing a plurality of data records, is provided comprising receiving a data record from an information source, the received data record having a predetermined number of fields containing information about a particular entity, standardizing and validating the data in the received data record. A system and method is also provided for retrieving records that refer to an entity characterized by a specific set of data values by comparing a predetermined number of fields within the received data record with a predetermined number of fields within the data records already in the database, selecting data records already in the database as candidates having data within some of the predetermined fields that is identical to the data in the fields of the received data record, and scoring the candidates to determine data records having information about the same entity.

U.S. Pat. No. 5,995,943 (Bull, et al., Nov. 30, 1999), expressly incorporated herein by reference, relates to an information aggregation and synthesis system. An information aggregation and synthesis system and process, which provides aggregation and packaging of structured or unstructured information from disparate sources such as those available on a network such as the Internet. A user operates a network compatible/addressable interface device. The network interface device communicates with local datastores or network accessible datastores via an addressing scheme such as Uniform Resource Locator addresses (URLs) utilized by the Internet. Data passing between the network interface device and the datastores is accessed, polled, and retrieved through an intermediary gateway system. Such aggregated information is then synthesized, customized, personalized and localized to meet the information resource requests specified by the user via the network interface device.

U.S. Pat. No. 6,012,035 (Freeman, Jr., et al., Jan. 4, 2000), expressly incorporated herein by reference, relates to a system and method for supporting delivery of health care. Effectuation of a health care provision agency cooperative function is established through a communication network linking all the various entities of the cooperative. The entities include the third party payor members, the health providing individuals, clinics, or the like, along with secondary providers including pharmacies and laboratories, health care facilities such as hospitals, and the several entities associated with management of the cooperative and appropriate funds transfer functions. A coordinating interface system maintains data storage of the necessary information, and manages the entity inter-communications in accordance with the basic structure of the active and eligible elements of the agency cooperative.

U.S. Pat. No. 6,035,276 (Newman, et al., Mar. 7, 2000), expressly incorporated herein by reference, relates to a system and method for selectively generating provider application forms required to be submitted to health care provider organizations by physicians and related health care professionals. Physician credentialing profiles containing physician credentialing information are stored into a system database together with a plurality of different provider application formats associated with particular application forms which are completed and selected data extracted from the common information contained in the stored physician credentialing profiles. The method automatically inputs a subset of physician credentialing information required by a particular selected provider application format into the provider application form associated with that format and generates the particular provider application form.

U.S. Pat. No. 6,055,494 (Friedman, Apr. 25, 2000), expressly incorporated herein by reference, relates to a system and method for medical language extraction and encoding. In computerized processing of natural-language medical/clinical data including phrase parsing and regularizing, parameters are referred to whose value can be specified by the user. Thus, a computerized system can be provided with versatility, for the processing of data originating in diverse domains, for example. Further to a parser and a regularizer, the system includes a preprocessor, output filters, and an encoding mechanism.

U.S. Pat. No. 6,055,506 (Frasca, Jr., Apr. 25, 2000) expressly incorporated herein by reference, relates to an outpatient care data system dedicated to the transmission, storage and retrieval of outpatient data relating to care of outpatients is provided with a regional data system located at a regional location, a plurality of metropolitan area data systems operatively connected to the regional data system, each of the metropolitan area data systems being located at a different metropolitan location. Each metropolitan area data system may be provided with an electronic nursing station located within a hospital and first and second types of outpatient systems operatively coupled to the electronic nursing station on a real-time basis. The first type of outpatient system is situated at a first non-hospital location remote from the hospital and includes a medical device associated with an outpatient present at the first non-hospital location, and the second type of outpatient system is situated at a second non-hospital location remote from the hospital and includes a medical device associated with an outpatient present at the second non-hospital location.

U.S. Pat. No. 6,076,066 (DiRienzo, et al., Jun. 13, 2000), expressly incorporated herein by reference, relates to an attachment integrated claims (AIC) system formed by a combination of first, second and third storage media. The first storage medium stores computer readable instructions for permitting a first computer system to receive textual data as field data, where each of the field data is displayed on a predetermined portion of a first screen of the first computer system, to assemble the field data and a corresponding digitized image into a first file having an integrated file format and to transmit the first file to a second computer system via a communications channel. The second storage medium stores computer readable instructions permitting the second computer system to receive the first file via the communications channel, to display the corresponding digitized attachment on a second screen of the second computer system, and to transfer the field data to a third computer operatively connected to the second computer. In addition, the third storage medium stores computer readable instructions permitting the third computer system to receive the field data from the second computer, to display the field data on a third screen and to generate a second file including portions of the field data extracted from the first file. In other words, the AIC system permits transmission of a customizable claim form and integrated attachment to an insurance carrier via a non-clearinghouse communications channel. An AIC system including several computers connected via a communications channel, an electronic file, and an operating method therefore are also described. In an exemplary case, the first file follows a predetermined graphic image interchange file format and the field data is incorporated into comment blocks associated with the predetermined graphic image interchange file format.

U.S. Pat. No. 6,076,166 (Moshfeghi, et al., Jun. 13, 2000), expressly incorporated herein by reference, relates to a system and method for personalizing hospital intranet web sites. The server includes a layer for dynamically generating web pages and other data objects using scripts, such as graphic, audio and video files, in dependence on stored information indicating the user's needs and preferences, including those presumed from stored information as to the user's function, job, or purpose for being at the hospital, and logged usage profiles, the level of the user's access privileges to confidential patient information, and the computer and physical environments of the user. Notably, the content is generated in dependence on the display resolution and lowest bandwidth link between the server and browser to limit the waiting time for downloads as well as the server load.

See also, U.S. Pat. No. 5,319,543 (Wilhelm, Jun. 7, 1994, Workflow server for medical records imaging and tracking system); U.S. Pat. No. 5,465,082 (Chaco, Nov. 7, 1995, Apparatus for automating routine communication in a facility); U.S. Pat. No. 5,508,912 (Schneiderman, Apr. 16, 1996, Clinical database of classified out-patients for tracking primary care outcome); U.S. Pat. No. 5,546,580 (Seliger, et al., Aug. 13, 1996, Method and apparatus for coordinating concurrent updates to a medical information database); U.S. Pat. No. 5,592,945 (Fiedler, Jan. 14, 1997, Real-time event charting in an electronic flowsheet); U.S. Pat. No. 5,619,991 (Sloane, Apr. 15, 1997, Delivery of medical services using electronic data communications); U.S. Pat. No. 5,664,109 (Johnson, et al., Sep. 2, 1997, Method for extracting pre-defined data items from medical service records generated by health care providers); U.S. Pat. No. 5,772,585 (Lavin, et al., Jun. 30, 1998, System and method for managing patient medical records); U.S. Pat. No. 5,778,882 (Raymond, et al., Jul. 14, 1998, Health monitoring system); U.S. Pat. No. 5,845,253 (Rensimer, et al., Dec. 1, 1998, System and method for recording patient-history data about on-going physician care procedures), each of which is expressly incorporated herein by reference.

Memory Cards

U.S. Pat. No. 6,021,393 (Honda, et al., Feb. 1, 2000), expressly incorporated herein by reference, relates to a medical information management system. As a portable memory card carried by a patient to store the patient's personal medical information, a hybrid-type memory card is used which includes an optical information recording area, an integrated circuit memory area and a magnetic information recording area. A read/write drive for the memory card includes an optical head, a carrier mechanism for loading the memory card on a carrier table and moving the loaded memory card relative to the optical head, and a coupler section for coupling electronic information to be read and written from and to the integrated circuit memory area of the memory card, so that reading and writing of optical information from and to the optical information recording area can be conducted simultaneously with reading and writing of the electronic information from and to the integrated circuit memory area.

U.S. Pat. No. 6,031,910 (Deindl, et al., Feb. 29, 2000), expressly incorporated herein by reference, relates to a method and system for the secure transmission and storage of protectable information, such as patient information, by means of a patient card. The data stored on the patient card are protected by cryptographic methods. The data is decrypted only with the same patient card if a doctor is authorized and the patient has given his agreement. All information that the patient card needs in order to decide whether the doctor is authorized, and the key for protecting the control data and the random key are held on the chip. The patient data can be freely transmitted to any storage medium. The chip controls both the access to the data and the encryption and decryption functions. Random keys, which are themselves stored encrypted together with the data, ensure that every data record remains separate from every other data record, and that only authorized persons can access it. Every patient card has its own record key. The system and method are not directed exclusively to patient data but can be applied to any protectable data to which right of access is to be restricted.

U.S. Pat. No. 6,034,605 (March, Mar. 7, 2000), expressly incorporated herein by reference, relates to a system and method for secure storage of personal information and for broadcast of the personal information at a time of emergency. A sealed package contains a medium storing personal information associated with an individual. The sealed package is stored at a facility until an emergency occurs. At a time of emergency, a missing person report concerning the individual generated by a law enforcement agency is processed. The personal information in the individual's sealed package is accessed in response to the missing person report and then broadcast on an electronic bulletin board accessible via the Internet.

U.S. Pat. No. 6,042,005 (Basile, et al., Mar. 28, 2000), expressly incorporated herein by reference, relates to a personal identification system for children, that includes two forms of identification. An identification card carried by the user contains the user's personal and medical information in an electronic medium. The identification card includes photographs of the user and their parent or legal guardian, a unique identification number for the user, and a list of corporate sponsors. The second identification device is to be worn by the user and includes the user's unique identification number and an access telephone number. A user interface enables the users to update their stored personal and medical information.

Rights-Based Access to Database Records

U.S. Pat. No. 5,325,294 (Keene, Jun. 28, 1994), expressly incorporated herein by reference, relates to a medical privacy system. A method and apparatus for authorized access to medical information concerning an individual while preserving the confidentiality of, and preventing unauthorized access to, such information, is provided. A computer database receives and stores the individual's medical information, after the individual is tested to establish this information and the date on which such information was most recently obtained. The computer database does not contain the individual's name, address or any other similar information by which the individual can be identified. The individual is given an identification card containing a photograph or holographic image of the individual and containing a confidential first identification number that is unique for the individual, where both the image and the first identification number are visually perceptible and cannot be altered on the card without detection of such alteration. The individual is also given a confidential second identification number that is not contained on the card and need not be unique for that individual. The computer database can be accessed telephonically, and the individual's medical information, or a portion thereof, can be read only by an inquirer, if the inquirer or the individual first provides the individual's first and second identification numbers. The inquirer can use the image and first identification number on the individual's card to confirm the identity of that individual but need not be told the individual's second identification number. After inquirer establishes the identity of the individual, the inquirer, with the assistance of the individual, can obtain a telephonic readout of the individual's medical information.

U.S. Pat. No. 5,499,293 (Behram, et al., Mar. 12, 1996), expressly incorporated herein by reference, relates to a privacy protected information medium using a data compression method, which uses an efficient data compression/decompression scheme using a passive data storage media such as a card-based approach for storage of medical data information. The system operates on existing personal computer hardware in a medical center or doctors' offices, doing away with expensive investments in specialized technologies of central processing hardware. With the advent of inexpensive desktop computing, a number of inventions have been offered to improve medical information storage and retrieval. They include the development of portable medical card technologies such as SmartCards and optical cards, which are capable of storing medical information, and can be carried by the patient. This card-based system provides a methodology for storage and retrieval of medical information from a passive credit-card sized instrument. The card is manufactured with minimal expense using existing well-known optical scanning or magnetic tape reading or a data interrogation means in a SmartCard based system.

U.S. Pat. No. 5,987,440 (O'Neil, et al., Nov. 16, 1999), expressly incorporated herein by reference, relates to a personal information security and exchange tool. Utilization of the E-Metro Community and Personal Information Agents assure an effective and comprehensive agent-rule based command and control of informational assets in a networked computer environment. The concerns of informational privacy and informational self-determination are addressed squarely by affording persons and entities a trusted means to author, secure, search, process, and exchange personal and/or confidential information in a networked computer environment. The formation of trusted electronic communities wherein members command and control their digital persona, exchanging or brokering for value the trusted utility of their informational assets is made possible. The system provides for the trusted utilization of personal data in electronic markets, providing both communities and individuals aggregate and individual rule-based control of the processing of their personal data.

U.S. Pat. No. 6,029,160 (Cabrera, et al., Feb. 22, 2000), expressly incorporated herein by reference, relates to a system and method for linking a database system with a system for filing data. Extensions to a database system provide linkage between data in the database system and files in a system for filing data that is external to the database system ("the filing system"). The linkage includes an external file reference (EFR) data type, which is defined in the database system for reference to files that are stored in the filing system. When entries are made in the database system that include EFR data-type references to files in the filing system, control information is provided by the database system to the filing system. The control information causes the filing system to control processing of referenced files according to referential constraints established in the database system.

U.S. Pat. No. 6,038,563 (Bapat, et al., Mar. 14, 2000), expressly incorporated herein by reference, relates to a system and method for restricting database access to managed object information using a permissions table that specifies access rights corresponding to user access rights to the managed objects. An access control database has access control objects that collectively store information that specifies access rights by users to specified sets of the managed objects. The specified access rights include access rights to obtain management information from the network. An access control server provides users access to the managed objects in accordance with the access rights specified by the access control database. An information transfer mechanism sends management information from the network to a database management system (DBMS) for storage in a set of database tables. Each database table stores management information for a corresponding class of managed objects. An access control procedure limits access to the management information stored in the database tables using at least one permissions table. A permissions table defines a subset of rows in the database tables that are accessible to at least one of the users. The set of database table rows that are accessible corresponds to the managed object access rights specified by the access control database. A user access request to access management information in the database is intercepted, and the access control procedure is invoked when the user access request is a select statement. The database access engine accesses information in the set of database tables using the permissions tables such that each user is allowed access only to management information in the set of database tables that the user would be allowed by the access control database to access.

U.S. Pat. No. 6,041,411 (Wyatt, Mar. 21, 2000), expressly incorporated herein by reference, relates to a method for defining and verifying user access rights to computer information. A method is provided for minimizing the potential for unauthorized use of digital information, particularly software programs, digital content and other computer information, by verifying user access rights to electronically transmitted digital information. A second computer system transmits requested digital information to a requesting first computing system in wrapped form, which includes digital instructions that must be successfully executed, or unwrapped, before access to the digital information is allowed. Successful unwrapping requires that certain conditions must be verified in accordance with the digital instructions, thereby allowing access to the digital information. In one embodiment, verification includes locking the digital information to the requesting computer system by comparing a generated digital fingerprint associated with the digital information to a digital fingerprint previously generated which is unique to the requesting computer system.

U.S. Pat. No. 6,044,401 (Harvey, Mar. 28, 2000), expressly incorporated herein by reference, relates to a network sniffer for monitoring and reporting network information that is not privileged beyond a user's privilege level. Nodes in the network include a network sniffer and an access sniffer. The access sniffer includes an access element and an access interface. The access element preferably includes a memory and a database. The access element accesses the network sniffer and filters out unavailable information by using information such as address and port numbers gathered by the network sniffer. Unavailable information includes information which is non-public or beyond the privilege level of the particular user. The access element evaluates data streams that are public information to determine if the data streams meet a predetermined criterion. If the data streams meet the predetermined criteria, then the data is saved in the database. The access element transfers only the information available to the particular user to the access interface. The access element can time itself for a limited amount of time for execution. Once the predetermined time period has expired, the access element is complete and it can save and transfer the appropriate information to the access interface.

U.S. Pat. No. 6,052,688 (Thorsen, Apr. 18, 2000), expressly incorporated herein by reference, relates to a computer-implemented control of access to atomic data items. The method comprises the steps of initiating and maintaining data access nodes in a variable access structure. Each access node is provided with references to other access nodes and/or to data items representing an object, each data item carrying only the amount of information that is relevant for its purpose. The data items or the references are provided with a time parameter thus enabling version control and the possibility to handle static or slowly changing data and frequently changed and updated data in a corresponding manner. The access nodes comprise access control parameters for access control from a safety point of view as well as for enabling different views of the access structure and underlying data and objects.

U.S. Pat. No. 6,073,106 (Rozen, et al., Jun. 6, 2000), expressly incorporated herein by reference, relates to a method of managing and controlling access to personal information. A participant is prompted to provide a constant identifier and a selected password via Internet communications or via phone/fax/mail. Emergency and confidential categories of medical information are identified, and the participant is prompted to provide personal information in each of the categories and a different personal identification number (E-PIN, C-PIN) for each category. The participant is also prompted to provide an instruction to disclose or to not disclose the personal information in the emergency category in the event a requester of the information is an emergency medical facility and is unable to provide the participant's E-PIN. Alteration of any of the participant's medical information is enabled upon presentation of the participant's identifier and password by the requester. The emergency information or the confidential information is disclosed upon presentation of the participant's identifier and E-PIN or C-PIN. In addition, the emergency information is disclosed to an emergency medical facility verified as such by a service provider in the event the participant has provided an instruction to disclose the emergency information. Storage and access to health related documents such as healthcare power of attorney, consent for treatment, and eyeglass prescription is also provided.

U.S. Pat. No. 6,073,234 (Kigo, et al., Jun. 6, 2000), expressly incorporated herein by reference, relates to a device and method for authenticating user's access rights to resources. Both of a user side and a protect side such as a programmer of an application programmer need not handle a large number of inherent information such as authentication keys. An access ticket generation device generates an access ticket from user unique identifying information and access rights authentication feature information. As unique security characteristic information, there is used a secret key of an elliptic curve encryption or an ElGamal encryption. A proof data generation device receives the access ticket, converts authentication data received from a proof data verification device into proof data by use of the access ticket and the user unique identifying information, and returns the resultant proof data to the proof data verification device. The proof data generation device or the proof data verification device decrypts the above-mentioned encryption. The proof data verification device verifies the access rights as correct only when a combination of an access ticket and user unique identifying information used in the proof data generation device is correct.

Role-Based Access

U.S. Pat. No. 6,023,765 (Kuhn, Feb. 8, 2000; Implementation of role-based access control in multi-level secure systems), expressly incorporated herein by reference, relates to a system and method for implementation of role-based access control in multi-level secure systems. Role-based access control (RBAC) is implemented on a multi-level secure (MLS) system by establishing a relationship between privileges within the RBAC system and pairs of levels and compartments within the MLS system. The advantages provided by RBAC, that is, reducing the overall number of connections that must be maintained, and, for example, greatly simplifying the process required in response to a change of job status of individuals within an organization, are then realized without loss of the security provided by MLS. A trusted interface function is developed to ensure that the RBAC rules permitting individual's access to objects are followed rigorously, and provides a proper mapping of the roles to corresponding pairs of levels and compartments. No other modifications are necessary. Access requests from subjects are mapped by the interface function to pairs of levels and compartments, after which access is controlled entirely by the rules of the MLS system.

See also, U.S. Pat. No. 6,073,242 (Electronic authority server); U.S. Pat. No. 6,073,240 (Method and apparatus for realizing computer security); U.S. Pat. No. 6,064,977 (Web server with integrated scheduling and calendaring); U.S. Pat. No. 6,055,637 (System and method for accessing enterprise-wide resources by presenting to the resource a temporary credential); U.S. Pat. No. 6,044,466 (Flexible and dynamic derivation of permissions); U.S. Pat. No. 6,041,349 (System management/network correspondence display method and system therefore); U.S. Pat. No. 6,014,666 (Declarative and programmatic access control of component-based server applications using roles); U.S. Pat. No. 5,991,877 (Object-oriented trusted application framework); U.S. Pat. No. 5,978,475 (Event auditing system); U.S. Pat. No. 5,949,866 (Communications system for establishing a communication channel on the basis of a functional role or task); U.S. Pat. No. 5,925,126 (Method for security shield implementation in computer system's software); U.S. Pat. No. 5,911,143 (Method and system for advanced role-based access control in distributed and centralized computer systems); U.S. Pat. No. 5,797,128 (System and method for implementing a hierarchical policy for computer system administration); U.S. Pat. No. 5,761,288 (Service context sensitive features and applications); U.S. Pat. No. 5,751,909 (Database system with methods for controlling object interaction by establishing database contracts between objects); U.S. Pat. No. 5,748,890 (Method and system for authenticating and auditing access by a user to non-natively secured applications); U.S. Pat. No. 5,621,889 (Facility for detecting intruders and suspect callers in a computer installation and a security system including such a facility); U.S. Pat. No. 5,535,383 (Database system with methods for controlling object interaction by establishing database contracts between objects); U.S. Pat. No. 5,528,516 (Apparatus and method for event correlation and problem reporting); U.S. Pat. No. 5,481,613 (Computer network cryptographic key distribution system); U.S. Pat. No. 5,347,578 (Computer system security); U.S. Pat. No. 5,265,221 (Access restriction facility method and apparatus), each of which is expressly incorporated herein by reference.

Secure Networks

U.S. Pat. No. 5,579,393 (Conner, et al., Nov. 26, 1996), expressly incorporated herein by reference, relates to a system and method for secure medical and dental record interchange, comprising a provider system and a payer system. The provider system includes a digital imager, a processing unit, a data transmission/reception device, and a memory having a provider management unit and a security unit. For each image acquired from the digital imager, the provider management unit generates a unique image ID, and creates an image relation structure having a source indicator, a status indicator, and a copy-from indicator. The provider management unit organizes images into a message for transmission to a payer system. The security unit performs message encryption, image signature generation, and message signature generation. The payer system includes a processing unit, a data transmission/reception device, and a memory having a payer management unit and a security unit. The payer system's security unit validates message signatures and image signatures received. The payer management unit generates a message rejection notification or a message acceptance notification. A method for provider-side secure medical and dental record interchange comprises the steps of: acquiring an image; generating a unique image ID and an image relation structure; maintaining a status indicator, a source indicator, and a copy-from indicator; generating an image signature; creating a message that includes the image; and generating a message signature. A method for payer-side secure medical and dental record interchange comprises the steps of: validating a message signature; validating an image signature; and selectively generating a message acceptance notification or a message rejection notification.

U.S. Pat. No. 5,890,129 (Spurgeon, Mar. 30, 1999), expressly incorporated herein by reference, relates to a system for exchanging health care insurance information. An information-exchange system is provided for controlling the exchange of business and clinical information between an insurer and multiple health care providers. The system includes an information-exchange computer that is connected over a local area network to an insurer computer using a proprietary database and over the Internet to health-care provider computers using open database-compliant databases. The information-exchange computer receives subscriber insurance data from the insurance computer database, translates the insurance data into an exchange database, and pushes the subscriber insurance data out over the Internet to the computer operated by the health-care provider assigned to each subscriber. The information-exchange system stores the data in the provider database. The information-exchange systems also provide for the preparation, submission, processing, and payment of claims over the local area network and with push technology over the Internet. In addition, prior authorization requests may be initiated in the provider computers and exchanged over the information-exchange system for review by the insurer computer. Processed reviews are transmitted back to the provider computer and to a specialist computer, if required, using push technology over the Internet.

U.S. Pat. No. 5,930,759 (Moore, et al., Jul. 27, 1999), expressly incorporated herein by reference, relates to a method and system for processing health care electronic data transactions. A system or network for assembling, filing and processing health care data transactions and insurance claims made by patients pursuant to health care policies issued to the patients by insurance companies or other carriers for service provided to the patients at health care facilities is provided. The network comprises a multitude of participating patients, a multitude of health care facilities, and a plurality of insurance companies or other carriers. Each of the patients has a personal data file including a set of patient related data encoded in a machine readable format, and each of the health care facilities has a telecommunications unit and a file reader to read the data on the personal data files and to transmit the patient related data to the telecommunications unit at the facility. The network further includes a central claims processing unit connected to the telecommunications units of the health care facilities to receive the electronic claim forms from those facilities and to adjudicate those claims.

U.S. Pat. No. 5,933,498 (Schneck, et al., Aug. 3, 1999), expressly incorporated herein by reference, relates to a system for controlling access and distribution of digital property represented as data. Portions of the data are protected and rules concerning access rights to the data are determined. Access to the protected portions of the data is prevented, other than in a non-useable form; and users are provided access to the data only in accordance with the rules as enforced by a mechanism protected by tamper detection. A method is also provided for distributing data for subsequent controlled use of those data. The method includes protecting portions of the data; preventing access to the protected portions of the data other than in a non-useable form; determining rules concerning access rights to the data; protecting the rules; and providing a package including: the protected portions of the data and the protected rules. A user is provided controlled access to the distributed data only in accordance with the rules as enforced by a mechanism protected by tamper protection. A device is provided for controlling access to data having protected data portions and rules concerning access rights to the data. The device includes means for storing the rules; and means for accessing the protected data portions only in accordance with the rules, whereby user access to the protected data portions is permitted only if the rules indicate that the user is allowed to access the portions of the data.

U.S. Pat. No. 5,978,918 (Scholnick, et al., Nov. 2, 1999), expressly incorporated herein by reference, relates to a practical method and system for supplementing or replacing current security protocols used on public networks involving the distribution of a proprietary system for use on a public network access provider's network. The proprietary system includes processing hardware and proprietary software. The proprietary system transmits private data, outside the Internet, over proprietary lines to a back-end process. When a "sender" sends private data it is sent over the proprietary system to a back-end process. The back-end process returns a time sensitive token that the "sender" sends to the "receiver". The "receiver" takes the time sensitive token and uses it to either retrieve the private data, over a proprietary system, or initiate a transaction with a financial institution. Encryption is used to allow authentication of the participants. This method can be used in conjunction with Secure Socket Layer (SSL) encryption and/or the Secure Electronic Transaction (SET) protocol.

U.S. Pat. No. 6,005,943 (Cohen, et al., Dec. 21, 1999), expressly incorporated herein by reference, relates to electronic identifiers for network terminal devices. The generation of electronic identifiers for network interface units connected to a data network for use in detecting unauthorized decryption of encrypted data transmitted over the data network. A random number is generated for use as a private key decryption code and is stored in memory in each network interface unit. A public key is calculated from the stored private key using a non-invertible mathematical formula. If the calculated public key is unique, then a portion of the public key (e.g. a subset of its bits) is stored in a data provider database as an electronic identifier for use in detecting unauthorized decryption of data by the interface unit.

U.S. Pat. No. 6,009,526 (Choi, Dec. 28, 1999), expressly incorporated herein by reference, relates to an information security system for tracing information outflow from a remotely accessible computer or computer network. The system includes an internal communication system that has at least one internal computer for transmitting security information by tracing data through communication equipment, outputting the data to an external output means, and connecting the internal computer to an external network. A communication monitoring device stores information regarding the data that is to be transmitted by applying a security policy according to a security grade assigned to the destination to which the data is to be transmitted. The communication-monitoring device is configured for extracting the identification of the destination from the transmitted data. It also includes a communication-monitoring server for storing and displaying predetermined information about the data to be transmitted and for determining whether the tracing information is stored according to the security grade for the identified destination. A method of operating the disclosed system is also described.

U.S. Pat. No. 6,021,202 (Anderson, et al., Feb. 1, 2000), expressly incorporated herein by reference, relates to a method and system for processing electronic documents, which includes a markup language according to the SGML standard in which document type definitions are created under which electronic documents are divided into blocks that are associated with logical fields that are specific to the type of block. Each of many different types of electronic documents can have a record mapping to a particular environment, such as a legacy environment of a banking network, a hospital's computer environment for electronic record keeping, a lending institution's computer environment for processing loan applications, or a court or arbitrator's computer system. Semantic document type definitions for various electronic document types (including, for example, electronic checks, mortgage applications, medical records, prescriptions, contracts, and the like) can be formed using mapping techniques between the logical content of the document and the block that is defined to include such content. Also, the various document types are preferably defined to satisfy existing customs, protocols and legal rules.

U.S. Pat. No. 6,021,491 (Renaud, Feb. 1, 2000), expressly incorporated herein by reference, relates to digital signatures for data streams and data archives. Methods, apparatuses and products are provided for verifying the authenticity of data within one or more data files Each data file is provided with an identifier, such as a one-way hash function or cyclic redundancy checksum. A signature file, that includes the identifiers for one or more data files, is provided with a digital signature created with a signature algorithm. The data file(s) and signature file are then transferred, or otherwise provided to a user. The user verifies the digital signature in the signature file using a signature-verifying algorithm. Once verified as being authentic, the signature file can be used to verify each of the data files. Verification of the data files can be accomplished by comparing the identifier for each data file with the corresponding identifier in the signature file. If the identifiers in the data and signature files match, then the data file can be marked as authentic. If the identifiers do not match then the data file can be rejected or otherwise dealt with accordingly.

U.S. Pat. No. 6,021,497 (Bouthillier, et al., Feb. 1, 2000), expressly incorporated herein by reference, relates to a secured network system which will allow only authorized users of the seed network system to access classified data provided by a secured network server. The secured network system includes a readykey controller, which has connected thereto a plurality of card readers. A user of the secured network system inserts a microchip embedded card into one of the card readers which then provides an authorization signal to the readykey controller indicating that the user is authorized to use one of a plurality of computers within the secured network system to receive and process classified data. The readykey controller sends an enable signal to a data relay switch enabling a data line associated with the card reader and the computer selected by the user allowing classified data to be transmitted from the secured network server through the data relay switch to the selected computer. Each of the three computers also has a power relay switch connected thereto which is activated by the readykey controller whenever authorization to activate the computer is provided to the readykey controller from another of the plurality of card readers.

U.S. Pat. No. 6,023,762 (Dean, et al., Feb. 8, 2000), expressly incorporated herein by reference, relates to a data access and retrieval system which comprises a plurality of user data sources each storing electronic data signals describing data specific to a user, or enabling services selected by a user; an agent device which is configurable to select individual ones of the user data sources and present selections of user data and service data to a set of callers who may interrogate the agent device remotely over a communications network; a plurality of service terminals capable of communicating with the agent device over a communications network the service terminals operable by callers; and a plurality of key devices, storing caller information and security code information for enabling remote access of selections of user data and/or services to be transmitted over a communications network to a caller located at a service terminal.

U.S. Pat. No. 6,029,245 (Scanlan, Feb. 22, 2000), expressly incorporated herein by reference, relates to a method and system for dynamically assigning security parameters to hypertext markup language (HTML) pages of an information provider on the worldwide web, whereby only one set of HTML pages need be stored and maintained for retrieval by client computers using differing security protocols. A security injection profile is provided for storing security parameters for each respective security protocol. When a browser enabled with a particular security protocol requests one of the HTML pages in the secure set, the page is accessed from web server storage, security parameters of the particular protocol are accessed and injected into the accessed page, and the page is sent to the requesting browser.

U.S. Pat. No. 6,049,875 (Suzuki, et al., Apr. 11, 2000), expressly incorporated herein by reference, relates to a security apparatus and method. A service is supplied to a user while maintaining the security of the service. A person discrimination section discriminates the user to be supplied the service. A user situation decision section decides whether the user is authorized to use the service. An infringement situation decision section detects whether a non-user intrudes into a use area of the service in order to decide whether the security of the service is infringed. A service control section supplies the service to the user in case the person discrimination section discriminates the user, and controls a supply of the service if the use situation decision section decides the user is not under the situation to use the service or the infringement situation decision section decides that the security of the service is infringed.

U.S. Pat. No. 6,055,508 (Naor, et al., Apr. 25, 2000), expressly incorporated herein by reference, relates to a method for secure accounting and auditing on a communications network. A method for secure accounting and auditing of a communications network operates in an environment in which many servers serve an even larger number of clients (e.g. the web), and are required to meter the interaction between servers and clients (e.g. counting the number of clients that were served by a server). The method (metering process) is very efficient and does not require extensive usage of any new communication channels. The metering is secure against fraud attempts by servers that inflate the number of their clients and against clients that attempt to disrupt the metering process. Several secure and efficient constructions of this method are based on efficient cryptographic techniques, are also very accurate, and preserve the privacy of the clients.

U.S. Pat. No. 6,065,119 (Sandford, II, et al., May 16, 2000), expressly incorporated herein by reference, relates to a method of authenticating digital data such as measurements made for medical, environmental purposes, or forensic purpose, and destined for archival storage or transmission through communications channels in which corruption or modification in part is possible. Authenticated digital data contain data-metric quantities that can be constructed from the digital data by authorized persons having a digital key. To verify retrieved or received digital data, the data-metrics constructed from the retrieved or received data are compared with similar data-metrics calculated for the retrieved or received digital data. The comparison determines the location and measures the amount of modification or corruption in the retrieved or received digital data.

U.S. Pat. No. 6,073,240 (Kurtzberg, et al., Jun. 6, 2000), expressly incorporated herein by reference, relates to a method and apparatus for realizing computer security. The method includes the steps of establishing an authorization window for enabling computer system actions consistent with an authorization rule; and, monitoring the actions as an indicia of conformance to the authorization rule. The method preferably provides a pattern of system actions as an indicia of compliance with an authorization rule, and provides notification of predetermined patterns.

U.S. Pat. No. 6,075,860 (Ketcham, Jun. 13, 2000), expressly incorporated herein by reference, relates to an apparatus and method for authentication and encryption of a remote terminal over a wireless link. A method and system is provided for authenticating an authorized user of a remote terminal attempting to interconnect with a computer network over a wireless modem is provided. An encrypted wireless communication channel is established between a remote terminal and a network server for facilitating the authentication process. An authorized user presents an authentication card containing credentials including a user identifier and an authentication encryption key to a remote terminal. The remote terminal establishes a wireless communication channel with a network server that provides a firewall between unauthenticated users and a computer network. The network server and the remote terminal then exchange encrypted information thus verifying the authenticity of each party. The remote terminal and the network server each independently generate a data encryption key for use in establishing a secure encrypted wireless communication channel therebetween.

U.S. Pat. No. 6,075,861 (Miller, II, Jun. 13, 2000), expressly incorporated herein by reference, relates to a security access system, having an entry access system that includes a locking mechanism enabling authorized entry at a secured entry point to a closed access area or computing device. Entry is approved in response to an interaction between an intended entrant and the entry access system that involves an interchange of multidigit numbers and use of ID and PINs for generation of a multidigit check number to establish authenticity of a request for entry.

Cryptographic Technology

U.S. Pat. No. 5,956,408 (Arnold, Sep. 21, 1999), expressly incorporated herein by reference, relates to an apparatus and method for secure distribution of data. Data, including program and software updates, is encrypted by a public key encryption system using the private key of the data sender. The sender also digitally signs the data. The receiver decrypts the encrypted data, using the public key of the sender, and verifies the digital signature on the transmitted data. The program interacts with basic information stored within the confines of the receiver. As result of the interaction, the software updates are installed within the confines of the user, and the basic information stored within the confines of the user is changed.

U.S. Pat. No. 5,982,891 (Ginter, et al., Nov. 9, 1999); U.S. Pat. No. 5,949,876 (Ginter, et al., Sep. 7, 1999); and U.S. Pat. No. 5,892,900 (Ginter, et al., Apr. 6, 1999), expressly incorporated herein by reference, relate to systems and methods for secure transaction management and electronic rights protection. Electronic appliances, such as computers, help to ensure that information is accessed and used only in authorized ways, and maintain the integrity, availability, and/or confidentiality of the information. Such electronic appliances provide a distributed virtual distribution environment (VDE) that may enforce a secure chain of handling and control, for example, to control and/or meter or otherwise monitor use of electronically stored or disseminated information. Such a virtual distribution environment may be used to protect rights of various participants in electronic commerce and other electronic or electronic-facilitated transactions. Distributed and other operating systems, environments and architectures, such as, for example, those using tamper-resistant hardware-based processors, may establish security at each node. These techniques may be used to support an all-electronic information distribution, for example, utilizing the "electronic highway."

U.S. Pat. No. 6,009,177 (Sudia, Dec. 28, 1999), expressly incorporated herein by reference, relates to a cryptographic system and method with a key escrow feature that uses a method for verifiably splitting users' private encryption keys into components and for sending those components to trusted agents chosen by the particular users, and provides a system that uses modern public key certificate management, enforced by a chip device that also self-certifies. The methods for key escrow and receiving an escrow certificate are also applied herein to a more generalized case of registering a trusted device with a trusted third party and receiving authorization from that party enabling the device to communicate with other trusted devices. Further preferred embodiments provide for rekeying and upgrading of device firmware using a certificate system, and encryption of stream-oriented data.

U.S. Pat. No. 6,052,467 (Brands, Apr. 18, 2000), expressly incorporated herein by reference, relates to a system for ensuring that the blinding of secret-key certificates is restricted, even if the issuing protocol is performed in parallel mode. A cryptographic method is disclosed that enables the issuer in a secret-key certificate issuing protocol to issue triples consisting of a secret key, a corresponding public key, and a secret-key certificate of the issuer on the public key, in such a way that receiving parties can blind the public key and the certificate, but cannot blind a predetermined non-trivial predicate of the secret key even when executions of the issuing protocol are performed in parallel.

U.S. Pat. No. 6,052,780 (Glover, Apr. 18, 2000), expressly incorporated herein by reference, relates to a computer system and process for accessing an encrypted and self-decrypting digital information product while restricting access to decrypted digital information. Some of these problems with digital information protection systems may be overcome by providing a mechanism that allows a content provider to encrypt digital information without requiring either a hardware or platform manufacturer or a content consumer to provide support for the specific form of corresponding decryption. This mechanism can be provided in a manner that allows the digital information to be copied easily for back-up purposes and to be transferred easily for distribution, but which should not permit copying of the digital information in decrypted form. In particular, the encrypted digital information is stored as an executable computer program that includes a decryption program that decrypts the encrypted information to provide the desired digital information, upon successful completion of an authorization procedure by the user. In combination with other mechanisms that track distribution, enforce royalty payments and control access to decryption keys, an improved method is provided for identifying and detecting sources of unauthorized copies. Suitable authorization procedures also enable the digital information to be distributed for a limited number of uses and/or users, thus enabling per-use fees to be charged for the digital information.

See also, U.S. Pat. No. 4,200,770 (Cryptographic apparatus and method); 4,218,582 (Public key cryptographic apparatus and method); U.S. Pat. No. 4,264,782 (Method and apparatus for transaction and identity verification); U.S. Pat. No. 4,306,111 (Simple and effective public-key cryptosystem); U.S. Pat. No. 4,309,569 (Method of providing digital signatures); U.S. Pat. No. 4,326,098 (High security system for electronic signature verification); U.S. Pat. No. 4,351,982 (RSA Public-key data encryption system having large random prime number generating microprocessor or the like); U.S. Pat. No. 4,365,110 (Multiple-destinational cryptosystem for broadcast networks); U.S. Pat. No. 4,386,233 (Cryptographic key notarization methods and apparatus); U.S. Pat. No. 4,393,269 (Method and apparatus incorporating a one-way sequence for transaction and identity verification); U.S. Pat. No. 4,399,323 (Fast real-time public key cryptography); U.S. Pat. No. 4,405,829 (Cryptographic communications system and method); U.S. Pat. No. 4,438,824 (Apparatus and method for cryptographic identity verification); U.S. Pat. No. 4,453,074 (Protection system for intelligent cards); U.S. Pat. No. 4,458,109 (Method and apparatus providing registered mail features in an electronic communication system); U.S. Pat. No. 4,471,164 (Stream cipher operation using public key cryptosystem); U.S. Pat. No. 4,514,592 (Cryptosystem); U.S. Pat. No. 4,528,588 (Method and apparatus for marking the information content of an information carrying signal); U.S. Pat. No. 4,529,870 (Cryptographic identification, financial transaction, and credential device); U.S. Pat. No. 4,558,176 (Computer systems to inhibit unauthorized copying, unauthorized usage, and automated cracking of protected software); U.S. Pat. No. 4,567,600 (Method and apparatus for maintaining the privacy of digital messages conveyed by public transmission); U.S. Pat. No. 4,575,621 (Portable electronic transaction device and system therefor); U.S. Pat. No. 4,578,531 (Encryption system key distribution method and apparatus); U.S. Pat. No. 4,590,470 (User authentication system employing encryption functions); U.S. Pat. No. 4,595,950 (Method and apparatus for marking the information content of an information carrying signal); U.S. Pat. No. 4,625,076 (Signed document transmission system); U.S. Pat. No. 4,633,036 (Method and apparatus for use in public-key data encryption system); U.S. Pat. No. 6,026,379 (System, method and article of manufacture for managing transactions in a high availability system); U.S. Pat. No. 6,026,490 (Configurable cryptographic processing engine and method); U.S. Pat. No. 6,028,932 (Copy prevention method and apparatus for digital video system); U.S. Pat. No. 6,028,933 (Encrypting method and apparatus enabling multiple access for multiple services and multiple transmission modes over a broadband communication network); U.S. Pat. No. 6,028,936 (Method and apparatus for authenticating recorded media); U.S. Pat. No. 6,028,937 (Communication device which performs two-way encryption authentication in challenge response format); U.S. Pat. No. 6,028,939 (Data security system and method); U.S. Pat. No. 6,029,150 (Payment and transactions in electronic commerce system); U.S. Pat. No. 6,029,195 (System for customized electronic identification of desirable objects); U.S. Pat. No. 6,029,247 (Method and apparatus for transmitting secured data); U.S. Pat. No. 6,031,913 (Apparatus and method for secure communication based on channel characteristics); U.S. Pat. No. 6,031,914 (Method and apparatus for embedding data, including watermarks, in human perceptible images); U.S. Pat. No. 6,034,618 (Device authentication system which allows the authentication function to be changed); U.S. Pat. No. 6,035,041 (Optimal-resilience, proactive, public-key cryptographic system and method); U.S. Pat. No. 6,035,398 (Cryptographic key generation using biometric data); U.S. Pat. No. 6,035,402 (Virtual certificate authority); U.S. Pat. No. 6,038,315 (Method and system for normalizing biometric variations to authenticate users from a public database and that ensures individual biometric data privacy); U.S. Pat. No. 6,038,316 (Method and system for protection of digital information); U.S. Pat. No. 6,038,322 (Group key distribution); U.S. Pat. No. 6,038,581 (Scheme for arithmetic operations in finite field and group operations over elliptic curves realizing improved computational speed); U.S. Pat. No. 6,038,665 (System and method for backing up computer files over a wide area computer network); U.S. Pat. No. 6,038,666 (Remote identity verification technique using a personal identification device); U.S. Pat. No. 6,041,122 (Method and apparatus for hiding cryptographic keys utilizing autocorrelation timing encoding and computation); U.S. Pat. No. 6,041,123 (Centralized secure communications system); U.S. Pat. No. 6,041,357 (Common session token system and protocol); U.S. Pat. No. 6,041,408 (Key distribution method and system in secure broadcast communication); U.S. Pat. No. 6,041,410 (Personal identification fob); U.S. Pat. No. 6,044,131 (Secure digital x-ray image authentication method); U.S. Pat. No. 6,044,155 (Method and system for securely archiving core data secrets); U.S. Pat. No. 6,044,157 (Microprocessor suitable for reproducing AV data while protecting the AV data from illegal copy and image information processing system using the microprocessor); U.S. Pat. No. 6,044,205 (Communications system for transferring information between memories according to processes transferred with the information); U.S. Pat. No. 6,044,349 (Secure and convenient information storage and retrieval method and apparatus); U.S. Pat. No. 6,044,350 (Certificate meter with selectable indemnification provisions); U.S. Pat. No. 6,044,388 (Pseudorandom number generator); U.S. Pat. No. 6,044,462 (Method and apparatus for managing key revocation); U.S. Pat. No. 6,044,463 (Method and system for message delivery utilizing zero knowledge interactive proof protocol); U.S. Pat. No. 6,044,464 (Method of protecting broadcast data by fingerprinting a common decryption function); U.S. Pat. No. 6,044,466 (Flexible and dynamic derivation of permissions); U.S. Pat. No. 6,044,468 (Secure transmission using an ordinarily insecure network communication protocol such as SNMP); U.S. Pat. No. 6,047,051 (Implementation of charging in a telecommunications system); U.S. Pat. No. 6,047,066 (Communication method and device); U.S. Pat. No. 6,047,067 (Electronic-monetary system); U.S. Pat. No. 6,047,072 (Method for secure key distribution over a nonsecure communications network); U.S. Pat. No. 6,047,242 (Computer system for protecting software and a method for protecting software); U.S. Pat. No. 6,047,268 (Method and apparatus for billing for transactions conducted over the internet); U.S. Pat. No. 6,047,269 (Self-contained payment system with circulating digital vouchers); U.S. Pat. No. 6,047,374 (Method and apparatus for embedding authentication information within digital data); U.S. Pat. No. 6,047,887 (System and method for connecting money modules); U.S. Pat. No. 6,049,610 (Method and apparatus for digital signature authentication); U.S. Pat. No. 6,049,612 (File encryption method and system); U.S. Pat. No. 6,049,613 (Method and apparatus for encrypting, decrypting, and providing privacy for data values); U.S. Pat. No. 6,049,671 (Method for identifying and obtaining computer software from a network computer); U.S. Pat. No. 6,049,785 (Open network payment system for providing for authentication of payment orders based on a confirmation electronic mail message); U.S. Pat. No. 6,049,786 (Electronic bill presentment and payment system which deters cheating by employing hashes and digital signatures); U.S. Pat. No. 6,049,787 (Electronic business transaction system with notarization database and means for conducting a notarization procedure); U.S. Pat. No. 6,049,838 (Persistent distributed capabilities); U.S. Pat. No. 6,049,872 (Method for authenticating a channel in large-scale distributed systems); U.S. Pat. No. 6,049,874 (System and method for backing up computer files over a wide area computer network); U.S. Pat. No. 6,052,466 (Encryption of data packets using a sequence of private keys generated from a public key exchange); U.S. Pat. No. 6,052,467 (System for ensuring that the blinding of secret-key certificates is restricted, even if the issuing protocol is performed in parallel mode); U.S. Pat. No. 6,052,469 (Interoperable cryptographic key recovery system with verification by comparison); U.S. Pat. No. 6,055,314 (System and method for secure purchase and delivery of video content programs); U.S. Pat. No. 6,055,321 (System and method for hiding and extracting message data in multimedia data); U.S. Pat. No. 6,055,508 (Method for secure accounting and auditing on a communications network); U.S. Pat. No. 6,055,512 (Networked personal customized information and facility services); U.S. Pat. No. 6,055,636 (Method and apparatus for centralizing processing of key and certificate life cycle management); U.S. Pat. No. 6,055,639 (Synchronous message control system in a Kerberos domain); U.S. Pat. No. 6,056,199 (Method and apparatus for storing and reading data); U.S. Pat. No. 6,057,872 (Digital coupons for pay televisions); U.S. Pat. No. 6,058,187 (Secure telecommunications data transmission); U.S. Pat. No. 6,058,188 (Method and apparatus for interoperable validation of key recovery information in a cryptographic system); U.S. Pat. No. 6,058,189 (Method and system for performing secure electronic monetary transactions); U.S. Pat. No. 6,058,193 (System and method of verifying cryptographic postage evidencing using a fixed key set); U.S. Pat. No. 6,058,381 (Many-to-many payments system for network content materials); U.S. Pat. No. 6,058,383 (Computationally efficient method for trusted and dynamic digital objects dissemination); U.S. Pat. No. 6,061,448 (Method and system for dynamic server document encryption); U.S. Pat. No. 6,061,454 (System, method, and computer program for communicating a key recovery block to enable third party monitoring without modification to the intended receiver); U.S. Pat. No. 6,061,692 (System and method for administering a meta database as an integral component of an information server); U.S. Pat. No. 6,061,789 (Secure anonymous information exchange in a network); U.S. Pat. No. 6,061,790 (Network computer system with remote user data encipher methodology); U.S. Pat. No. 6,061,791 (Initial secret key establishment including facilities for verification of identity); U.S. Pat. No. 6,061,792 (System and method for fair exchange of time-independent information goods over a network); U.S. Pat. No. 6,061,794 (System and method for performing secure device communications in a peer-to-peer bus architecture); U.S. Pat. No. 6,061,796 (Multi-access virtual private network); U.S. Pat. No. 6,061,799 (Removable media for password based authentication in a distributed system); U.S. Pat. No. 6,064,723 (Network-based multimedia communications and directory system and method of operation); U.S. Pat. No. 6,064,738 (Method for encrypting and decrypting data using chaotic maps); U.S. Pat. No. 6,064,740 (Method and apparatus for masking modulo exponentiation calculations in an integrated circuit); U.S. Pat. No. 6,064,741 (Method for the computer-aided exchange of cryptographic keys between a user computer unit U and a network computer unit N); U.S. Pat. No. 6,064,764 (Fragile watermarks for detecting tampering in images); U.S. Pat. No. 6,064,878 (Method for separately permissioned communication); U.S. Pat. No. 6,065,008 (System and method for secure font subset distribution); U.S. Pat. No. 6,067,620 (Stand alone security device for computer networks); U.S. Pat. No. 6,069,647 (Conditional access and content security method); U.S. Pat. No. 6,069,952 (Data copyright management system); U.S. Pat. No. 6,069,954 (Cryptographic data integrity with serial bit processing and pseudo-random generators); U.S. Pat. No. 6,069,955 (System for protection of goods against counterfeiting); U.S. Pat. No. 6,069,969 (Apparatus and method for electronically acquiring fingerprint images); U.S. Pat. No. 6,069,970 (Fingerprint sensor and token reader and associated methods); U.S. Pat. No. 6,070,239 (System and method for executing verifiable programs with facility for using non-verifiable programs from trusted sources); U.S. Pat. No. 6,072,870 (System, method and article of manufacture for a gateway payment architecture utilizing a multichannel, extensible, flexible architecture); U.S. Pat. No. 6,072,874 (Signing method and apparatus using the same); U.S. Pat. No. 6,072,876 (Method and system for depositing private key used in RSA cryptosystem); U.S. Pat. No. 6,073,125 (Token key distribution system controlled acceptance mail payment and evidencing system); U.S. Pat. No. 6,073,160 (Document communications controller); U.S. Pat. No. 6,073,172 (Initializing and reconfiguring a secure network interface); U.S. Pat. No. 6,073,234 (Device for authenticating user's access rights to resources and method); U.S. Pat. No. 6,073,236 (Authentication method, communication method, and information processing apparatus); U.S. Pat. No. 6,073,237 (Tamper resistant method and apparatus); U.S. Pat. No. 6,073,238 (Method of securely loading commands in a smart card); U.S. Pat. No. 6,073,242 (Electronic authority server); U.S. Pat. No. 6,075,864 (Method of establishing secure, digitally signed communications using an encryption key based on a blocking set cryptosystem); U.S. Pat. No. 6,075,865 (Cryptographic communication process and apparatus); U.S. Pat. No. 6,076,078 (Anonymous certified delivery); U.S. Pat. No. 6,076,162 (Certification of cryptographic keys for chipcards); U.S. Pat. No. 6,076,163 (Secure user identification based on constrained polynomials); U.S. Pat. No. 6,076,164 (Authentication method and system using IC card); U.S. Pat. No. 6,076,167 (Method and system for improving security in network applications); U.S. Pat. No. 6,078,663 (Communication apparatus and a communication system); U.S. Pat. No. 6,078,665 (Electronic encryption device and method); U.S. Pat. No. 6,078,667 (Generating unique and unpredictable values); U.S. Pat. No. 6,078,909 (Method and apparatus for licensing computer programs using a DSA signature); U.S. Pat. No. 6,079,018 (System and method for generating unique secure values for digitally signing documents); U.S. Pat. No. 6,079,047 (Unwrapping system and method for multiple files of a container); U.S. Pat. No. 6,081,597 (Public key cryptosystem method and apparatus); U.S. Pat. No. 6,081,598 (Cryptographic system and method with fast decryption); U.S. Pat. No. 6,081,610 (System and method for verifying signatures on documents); U.S. Pat. No. 6,081,790 (System and method for secure presentment and payment over open networks); U.S. Pat. No. 6,081,893 (System for supporting secured log-in of multiple users into a plurality of computers using combined presentation of memorized password and transportable passport record), each of which is expressly incorporated herein by reference.

Watermarking

U.S. Pat. No. 5,699,427 (Chow, et al., Dec. 16, 1997), expressly incorporated herein by reference, relates to a method to deter document and intellectual property piracy through individualization, and a system for identifying the authorized receiver of any particular copy of a document. More specifically, each particular copy of a document is fingerprinted by applying a set of variations to a document, where each variation is a change in data contents, but does not change the meaning or perusal experience of the document. A database associating a set of variants to a receiver is maintained. Thus any variant or copy of that variant can be traced to an authorized receiver.

See also, U.S. Pat. No. 4,734,564 (Transaction system with off-line risk assessment); U.S. Pat. No. 4,812,628 (Transaction system with off-line risk assessment); U.S. Pat. No. 4,926,325 (Apparatus for carrying out financial transactions via a facsimile machine); U.S. Pat. No. 5,235,166 (Data verification method and magnetic media therefor); U.S. Pat. No. 5,254,843 (Securing magnetically encoded data using timing variations in encoded data); U.S. Pat. No. 5,341,429 (Transformation of ephemeral material); U.S. Pat. No. 5,428,683 (Method and apparatus for fingerprinting and authenticating magnetic media); U.S. Pat. No. 5,430,279 (Data verification method and magnetic media therefor); U.S. Pat. No. 5,521,722 (Image handling facilitating computer aided design and manufacture of documents); U.S. Pat. No. 5,546,462 (Method and apparatus for fingerprinting and authenticating various magnetic media); U.S. Pat. No. 5,606,609 (Electronic document verification system and method); U.S. Pat. No. 5,613,004 (Steganographic method and device); U.S. Pat. No. 5,616,904 (Data verification method and magnetic media therefor); U.S. Pat. No. 5,636,292 (Steganography methods employing embedded calibration data); U.S. Pat. No. 5,646,997 (Method and apparatus for embedding authentication information within digital data); U.S. Pat. No. 5,659,726 (Data embedding); U.S. Pat. No. 5,664,018 (Watermarking process resilient to collusion attacks); U.S. Pat. No. 5,687,236 (Steganographic method and device); U.S. Pat. No. 5,710,834 (Method and apparatus responsive to a code signal conveyed through a graphic image); U.S. Pat. No. 5,727,092 (Compression embedding); U.S. Pat. No. 5,734,752 (Digital watermarking using stochastic screen patterns); U.S. Pat. No. 5,740,244 (Method and apparatus for improved fingerprinting and authenticating various magnetic media); U.S. Pat. No. 5,745,569 (Method for stega-cipher protection of computer code); U.S. Pat. No. 5,745,604 (Identification/authentication system using robust, distributed coding); U.S. Pat. No. 5,748,763 (Image steganography system featuring perceptually adaptive and globally scalable signal embedding); U.S. Pat. No. 5,748,783 (Method and apparatus for robust information coding); U.S. Pat. No. 5,761,686 (Embedding encoded information in an iconic version of a text image); U.S. Pat. No. 5,765,152 (System and method for managing copyrighted electronic media); U.S. Pat. No. 5,768,426 (Graphics processing system employing embedded code signals); U.S. Pat. No. 5,778,102 (Compression embedding); U.S. Pat. No. 5,790,703 (Digital watermarking using conjugate halftone screens); U.S. Pat. No. 5,819,289 (Data embedding employing degenerate clusters of data having differences less than noise value); U.S. Pat. No. 5,822,432 (Method for human-assisted random key generation and application for digital watermark system); U.S. Pat. No. 5,822,436 (Photographic products and methods employing embedded information); U.S. Pat. No. 5,832,119 (Methods for controlling systems using control signals embedded in empirical data); U.S. Pat. No. 5,841,886 (Security system for photographic identification); U.S. Pat. No. 5,841,978 (Network linking method using steganographically embedded data objects); U.S. Pat. No. 5,848,155 (Spread spectrum watermark for embedded signalling); U.S. Pat. No. 5,850,481 (Steganographic system); U.S. Pat. No. 5,862,260 (Methods for surveying dissemination of proprietary empirical data); U.S. Pat. No. 5,878,137 (Method for obtaining authenticity identification devices for using services in general, and device obtained thereby); U.S. Pat. No. 5,889,868 (Optimization methods for the insertion, protection, and detection of digital watermarks in digitized data); U.S. Pat. No. 5,892,900 (Systems and methods for secure transaction management and electronic rights protection); U.S. Pat. No. 5,905,505 (Method and system for copy protection of on-screen display of text); U.S. Pat. No. 5,905,800 (Method and system for digital watermarking); U.S. Pat. No. 5,915,027 (Digital watermarking); U.S. Pat. No. 5,920,628 (Method and apparatus for fingerprinting and authenticating various magnetic media); U.S. Pat. No. 5,930,369 (Secure spread spectrum watermarking for multimedia data); U.S. Pat. No. 5,933,498 (System for controlling access and distribution of digital property); U.S. Pat. No. 5,943,422 (Steganographic techniques for securely delivering electronic digital rights management control information over insecure communication channels); U.S. Pat. No. 5,946,414 (Encoding data in color images using patterned color modulated image regions); U.S. Pat. No. 5,949,885 (Method for protecting content using watermarking); U.S. Pat. No. 5,974,548 (Media-independent document security method and apparatus); U.S. Pat. No. 5,995,625 (Electronic cryptographic packing); U.S. Pat. No. 6,002,772 (Data management system); U.S. Pat. No. 6,004,276 (Open architecture cardiology information system); U.S. Pat. No. 6,006,328 (Computer software authentication, protection, and security system); U.S. Pat. No. 6,006,332 (Rights management system for digital media); U.S. Pat. No. 6,018,801 (Method for authenticating electronic documents on a computer network); U.S. Pat. No. 6,026,193 (Video steganography); U.S. Pat. No. 6,044,464 (Method of protecting broadcast data by fingerprinting a common decryption function); U.S. Pat. No. 6,047,374 (Method and apparatus for embedding authentication information within digital data); U.S. Pat. No. 6,049,627 (Covert digital identifying indicia for digital image); U.S. Pat. No. 6,061,451 (Apparatus and method for receiving and decrypting encrypted data and protecting decrypted data from illegal use); U.S. Pat. No. 6,064,737 (Anti-piracy system for wireless telephony); U.S. Pat. No. 6,064,764 (Fragile watermarks for detecting tampering in images); U.S. Pat. No. 6,069,914 (Watermarking of image data using MPEG/JPEG coefficients); U.S. Pat. No. 6,076,077 (Data management system); U.S. Pat. No. 6,081,793 (Method and system for secure computer moderated voting), each of which is expressly incorporated herein by reference.

Role-Based Access

U.S. Pat. No. 6,023,765 (Kuhn, Feb. 8, 2000; Implementation of role-based access control in multi-level secure systems), expressly incorporated herein by reference, relates to a system and method for implementation of role-based access control in multi-level secure systems. Role-based access control (RBAC) is implemented on a multi-level secure (MLS) system by establishing a relationship between privileges within the RBAC system and pairs of levels and compartments within the MLS system. The advantages provided by RBAC, that is, reducing the overall number of connections that must be maintained, and, for example, greatly simplifying the process required in response to a change of job status of individuals within an organization, are then realized without loss of the security provided by MLS. A trusted interface function is developed to ensure that the RBAC rules permitting individual's access to objects are followed rigorously, and provides a proper mapping of the roles to corresponding pairs of levels and compartments. No other modifications are necessary. Access requests from subjects are mapped by the interface function to pairs of levels and compartments, after which access is controlled entirely by the rules of the MLS system.

See also, U.S. Pat. Nos. 6,073,242 (Electronic authority server); U.S. Pat. No. 6,073,240 (Method and apparatus for realizing computer security); U.S. Pat. No. 6,064,977 (Web server with integrated scheduling and calendaring); U.S. Pat. No. 6,055,637 (System and method for accessing enterprise-wide resources by presenting to the resource a temporary credential); U.S. Pat. No. 6,044,466 (Flexible and dynamic derivation of permissions); U.S. Pat. No. 6,041,349 (System management/network correspondence display method and system therefore); U.S. Pat. No. 6,014,666 (Declarative and programmatic access control of component-based server applications using roles); U.S. Pat. No. 5,991,877 (Object-oriented trusted application framework); U.S. Pat. No. 5,978,475 (Event auditing system); U.S. Pat. No. 5,949,866 (Communications system for establishing a communication channel on the basis of a functional role or task); U.S. Pat. No. 5,925,126 (Method for security shield implementation in computer system's software); U.S. Pat. No. 5,911,143 (Method and system for advanced role-based access control in distributed and centralized computer systems); U.S. Pat. No. 5,797,128 (System and method for implementing a hierarchical policy for computer system administration); U.S. Pat. No. 5,761,288 (Service context sensitive features and applications); U.S. Pat. No. 5,751,909 (Database system with methods for controlling object interaction by establishing database contracts between objects); U.S. Pat. No. 5,748,890 (Method and system for authenticating and auditing access by a user to non-natively secured applications); U.S. Pat. No. 5,621,889 (Facility for detecting intruders and suspect callers in a computer installation and a security system including such a facility); U.S. Pat. No. 5,535,383 (Database system with methods for controlling object interaction by establishing database contracts between objects); U.S. Pat. No. 5,528,516 (Apparatus and method for event correlation and problem reporting); U.S. Pat. No. 5,481,613 (Computer network cryptographic key distribution system); U.S. Pat. No. 5,347,578 (Computer system security); U.S. Pat. No. 5,265,221 (Access restriction facility method and apparatus), each of which is expressly incorporated herein by reference.

Computer System Security

U.S. Pat. No. 5,881,225 (Worth, Mar. 9, 1999), expressly incorporated herein by reference, relates to a security monitor for controlling functional access to a computer system. A security monitor controls security functions for a computer system. A user desiring access to the system inputs a user identification and password combination, and a role the user to assume is selected from among one or more roles defined in the system. Upon being validated as an authorized user performing a particular role, the user is then authorized to perform certain functions and tasks specifically and to see information associated with that role (and optimally the work group the user is assigned). For some users, no role or a "null" roll is chosen, and authorization for certain functions and tasks is accomplished due to that particular user having been predefined by an administrator as being allowed to perform those functions and tasks, usually due to the predefined privileges associated with the work group(s) to which the user belongs.

U.S. Pat. No. 5,937,068 (Audebert, Aug. 10, 1999), expressly incorporated herein by reference, relates to a system and method for user authentication employing dynamic encryption variables. The system includes a first card-like unit adapted to communicate with a second unit giving only conditionally access to a function. Both units are capable of running software for generating a password by means of encryption of a plurality of dynamic variables produced separately but in concert (so as to have a predetermined relationship, such as identity, with one another) in the units. The encryption is carried out in each unit by a public algorithm using a dynamically varying encryption key. Each time an access request is issued by a card user, the key is modified as a function of the number of access requests previously formulated by the card user. Access to the function is granted when the passwords generated in the units have a predetermined relationship (such as identity) with each other. In a "virtual token" implementation, the first unit can be a smart card, which stores the dynamic key and the variable representing the number of formulated authentication requests and executes an encryption algorithm, a smart card reader and a computer such as a personal computer. Either the smart card reader or the personal computer can generate the time dependent variable. In a "software token" implementation, the functions of the first unit are performed by a personal computer, thus eliminating the need for a smart card or a smart card reader.

U.S. Pat. No. 5,949,882 (Angelo, Sep. 7, 1999), expressly incorporated herein by reference, relates to a method and apparatus for allowing access to secured computer resources by utilizing a password and an external encryption algorithm. A method for permitting access to secured computer resources based upon a two-piece user verification process is provided. In one embodiment, the user verification process is carried out during a secure power-up procedure. At some point during the secure power-up procedure, the computer user is required to provide an external token or smart card that is coupled to the computer through specialized hardware. The token or smart card is used to store an encryption algorithm furnished with an encryption key that is unique or of limited production. The computer user is then required to enter a plain text user password. Once entered, the user password is encrypted using the encryption algorithm contained in the external token to create a peripheral password. The peripheral password is compared to a value stored in either secure system memory or in memory contained within a secured resource itself. If the two values match, access to the secured resource is permitted. In an alternate embodiment, the two-piece authentication process is conducted during normal computer operation outside of the secure power-on sequence. In this embodiment, the user password is entered by means of a secure keyboard communications channel. In either embodiment, the two-piece nature of the authorization process requires the presence of both the user password and the external token in order to generate the peripheral password.

U.S. Pat. No. 5,953,419 (Lohstroh, et al., Sep. 14, 1999), expressly incorporated herein by reference, relates to a cryptographic file labeling system for supporting secured access by multiple users. A system is disclosed for automatically distributing secured versions of a file decryption key to a plurality of file users by way of the file's security label. The label is defined to contain a plurality of Access-Control-Entries Records (ACER's) where each ACER includes a respective secured version of the file decryption key. Each such secured version is decipherable by a respective ACER private key. Each ACER may include respective other data such as: (a) ACER-unique identifying data for uniquely identifying the ACER or an associated user; (b) decryption algorithm identifying data for identifying the decryption process to be used to decrypt the encrypted data portion of the file; and (c) special handling code for specifying special handling for the code-containing ACER. The label is preferably covered by a digital signature but includes an extension buffer that is not covered by the digital signature. Users who wish to have an ACER of their own added to the label may submit add-on requests by writing to the extension buffer.

U.S. Pat. No. 5,956,400 (Chaum, et al., Sep. 21, 1999), expressly incorporated herein by reference, relates to partitioned information storage systems with controlled retrieval. An information storage system includes one or more information update terminals, a mapper, one or more partial-databases, and one or more query terminals, exchanging messages over a set of communication channels. An identifier-mapping mechanism provides (to an update terminal) a method for delegating control over retrieval of the data stored at the partial-databases to one or more mappers, typically operated by one or more trusted third parties. Update terminals supply information, which is stored in fragmented form by the partial-databases. Data-fragment identifiers and pseudonyms are introduced, preventing unauthorized de-fragmentation of information—thus providing compliance to privacy legislation—while at the same time allowing query terminals to retrieve (part of) the stored data or learn properties of the stored data. The mapper is necessarily involved in both operations, allowing data access policies to be enforced and potential abuse of stored information to be reduced. Introduction of multiple mappers acts to distribute information retrieval control among multiple trusted third parties. Introducing so-called "groupers" increases the efficiency of data retrieval for a common set of queries and further reduces potential abuse of information.

U.S. Pat. No. 5,958,050 (Griffin, et al., Sep. 28, 1999), expressly incorporated herein by reference, relates to a trusted delegation system. A trust manager examines each new class before it is allowed to execute by examining a policy file which includes data structures defining security policies of the user system, a certificate repository for storing a plurality of certificates, a certificate being a data record which is digitally signed and which certifies claims relevant to a security evaluation, a code examiner adapted to analyze the portion of code to determine potential resource use of the portion of code and a trust evaluator adapted to evaluate certificate requirements of the portion of code based on policy rules extracted from the policy file and the potential resource use specified by the code examiner. The trust evaluator also determines, from certificates from the certificate repository and a code identifier identifying the portion of code, whether execution of the portion of code is allowed by the policy rules given the potential resource use, the code supplier and applicable certificates. Certificates and policies can be specified in hierarchical form, so that some levels of security can be delegated to trusted entities.

U.S. Pat. No. 5,978,475 (Schneier, et al., Nov. 2, 1999), expressly incorporated herein by reference, relates to an event auditing system. In many computer applications, sensitive information must be kept on an untrusted machine. Such information must be protected against attackers, as well as against partially trusted entities to be given partial, but not total, access to the stored information. A method, apparatus and computer-readable data structure are provided for inhibiting an attacker from accessing or corrupting information stored by an untrusted machine. More specifically, in a log file generated during a process in which the untrusted machine is in limited communication with a trusted machine, entries generated prior to the attack remain secure (they cannot be modified without detection), even though subsequent entries can not be trusted. One embodiment also allows a partially trusted verifier to read and verify entries in the log file, but not to change them without detection. In another embodiment, operating with or without the trusted machine, the untrusted machine's log file can also incorporate log files of other processes.

U.S. Pat. No. 5,991,878 (McDonough, et al., Nov. 23, 1999), expressly incorporated herein by reference, relates to a system and method for controlling access to information in a distributed computing system. A request for the information is received and is accompanied by encrypted session state data. Based on the encrypted session state data, it is determined whether to pass the request on to a source of the information. In a memory buffer, old data is replaced by overwriting with a unique identifier. After the memory buffer has received new data and a procedure has been executed for copying the contents of the memory buffer to a destination, it is determined whether the unique identifier may be found at the destination.

U.S. Pat. No. 6,070,239 (McManis, May 30, 2000), expressly incorporated herein by reference, relates to a system and method for executing verifiable programs with facility for using non-verifiable programs from trusted sources. A computer system includes a program executer that executes verifiable architecture neutral programs and a class loader that prohibits the loading and execution of non-verifiable programs unless (A) the non-verifiable program resides in a trusted repository of such programs, or (B) the non-verifiable program is indirectly verifiable by way of a digital signature on the non-verifiable program that proves the program was produced by a trusted source. In the preferred embodiment, verifiable architecture neutral programs are Java bytecode programs whose integrity is verified using a Java bytecode program verifier. The non-verifiable programs are generally architecture specific compiled programs generated with the assistance of a compiler. Each architecture specific program typically includes two signatures, including one by the compiling party and one by the compiler. Each digital signature includes a signing party identifier and an encrypted message. The encrypted message includes a message generated by a predefined procedure, and is encrypted using a private encryption key associated with the signing party. A digital signature verifier used by the class loader includes logic for processing each digital signature by obtaining a public key associated with the signing party, decrypting the encrypted message of the digital signature with that public key so as generate a decrypted message, generating a test message by executing the predefined procedure on the architecture specific program associated with the digital signature, comparing the test message with the decrypted message, and issuing a failure signal if the decrypted message digest and test message digest do not match.

U.S. Pat. No. 6,079,021 (Abadi, et al., Jun. 20, 2000), expressly incorporated herein by reference, relates to a method and apparatus for strengthening passwords for protection of computer systems. A computer-implemented method provides access to processes and data using strengthened password. During an initialization phase, an access code is stored in a memory of a computer system. The access code is an application of a one-way hash function to a concatenation of a password and a password supplement. The size of the password supplement is a fixed number of bits. During operation of the system, a user enters a password, and the one-way hash function is applied to concatenations of the password and possible values having the size of the password supplement to yield trial access codes. Access is granted when one of the trial access codes is identical to the stored access code.

Computer Security Devices

U.S. Pat. No. 5,982,520 (Weiser, et al., Nov. 9, 1999), expressly incorporated herein by reference, relates to a personal storage device for receipt, storage, and transfer of digital information to other electronic devices has a pocket sized crush resistant casing with a volume of less than about ten cubic centimeters. A processor is positioned within the casing cavity and attached to the crush resistant casing, while a memory module also positioned within the casing cavity is configured to store received executable applications and data. An infrared transceiver is mounted on the crush resistant casing and in electronic communication with the processor and memory module to provide for receipt and storage of executable applications, and receipt, storage, and transfer of digital information to other electronic devices. The digital information stored by the personal storage device can be intermittently synchronized with other electronic devices.

U.S. Pat. No. 5,991,519 (Benhammou, et al., Nov. 23, 1999), expressly incorporated herein by reference, relates to a secure memory having multiple security levels. A secured memory comprises a first level security zone having an access code controlling access to the secured memory prior to an issuer fuse being blown, a security code attempts counter preventing access to the secured memory when a predetermined number of attempts at matching the access code have been made prior to resetting the security code attempts counter, a plurality of application zones, each of the plurality of application zones comprising: a storage memory zone, an application security zone having an application zone access code controlling access to the storage memory zone after an issuer fuse has been blown, an application zone security code attempts counter preventing access to the application zone when a predetermined number of attempts at matching the application zone access code have been made prior to resetting the application zone security code attempts counter, an erase key partition having an erase key code controlling erase access to the storage memory zone after an issuer fuse has been blown, and an erase key attempts counter preventing erase access to the application zone when a predetermined number of attempts at matching the erase key code have been made prior to resetting the erase key attempts counter.

U.S. Pat. No. 5,999,629 (Heer, et al., Dec. 7, 1999), expressly incorporated herein by reference, relates to a data encryption security module. Encryption keys used to encrypt such messages need to be managed in a highly secure manner. A unique device encryption key is generated, a cryptographic key formed from a unique identification key and an associated public key, and at least one program encryption key, in which the public key is generated as a function of the unique identification key. The module then encrypts the unique identification key and program encryption key using said device encryption key and stores the encrypted result in memory internal to security module, thereby securing the keys against misappropriation. In addition, the module provides a mechanism for using the program encryption key to encrypt information that it receives from an external source and store the encrypted information in memory external to the security module, and responsive to receiving from a requester a request for the program encryption key, encrypting the program encryption key, using a symmetrical encryption key generated as a function of a public key generated by a security module associated with the requester. The former security module then supplies the encrypted program encryption key to the requester.

U.S. Pat. No. 6,034,618 (Tatebayashi, et al., Mar. 7, 2000), expressly incorporated herein by reference, relates to a device authentication system that allows the authentication function to be changed. A decoder apparatus generates a random number for authenticating the optical disc drive apparatus and sends it to the optical disc drive apparatus as the challenge data. The optical disc drive apparatus selects one out of sixteen claimant functions stored in the claimant function unit and calculates the function value, which it sends to the decoder apparatus as the response data. The decoder apparatus compares the response data with sixteen function values to that are obtained using the sixteen verification functions stored in the verification function unit, and authenticates the optical disc drive apparatus when at least one of the function values matches the response data.

U.S. Pat. No. 6,041,412 (Timson, et al., Mar. 21, 2000), expressly incorporated herein by reference, relates to an apparatus and a method for providing access to a secured data or area, includes at least two secure data modules which contain security data and other information and which belong to a particular security scheme and a dual module reader for reading data and permissions instructions contained on the secure data modules. The two secure data modules include an enabling module and an interrogatable module. The interrogatable module and the enabling module communicate with each other via a dual module reader. Communication between the two modules is allowed as long as the two modules are members of the same security scheme. A scheme is defined by suitable proprietary encryption keys for enabling communication and data transfer between the two modules belonging to a common scheme and for preventing communication and data transfer between two modules belonging to different schemes. The communication between the two modules provides an improved data security and access control system that eliminates the need for multiple passwords for various operations and also prevents problems associated with conventional access cards that are used in conjunction with passwords.

U.S. Pat. No. 6,061,451 (Muratani, et al., May 9, 2000), expressly incorporated herein by reference, relates to an apparatus and method for receiving and decrypting encrypted data and protecting decrypted data from illegal use. A data receiving apparatus is formed of a set top unit connected to a network and a security module. Digital video data, supplied from the network and scrambled according to a first system, is scrambled according to a second system in a scramble circuit in the set top unit, and is supplied to the security module. The data is descrambled according to the first system in a descramble circuit in the security module, and is transferred back to the set top unit. The data is descrambled according to the second system in a descramble circuit in the set top unit, and is outputted to an image display terminal via an MPEG decoder.

U.S. Pat. No. 6,069,647 (Sullivan, et al., May 30, 2000), expressly incorporated herein by reference, relates to a conditional access and content security method. An interface unit, connected to a programmable unit, is capable of containing a time-sensitive key. The programmable unit is allowed to receive digital content from the interface unit upon establishing that the time-sensitive key is also contained therein.

Computer Network Firewall

U.S. Pat. No. 5,944,823 (Jade, et al., Aug. 31, 1999), expressly incorporated herein by reference, relates to a system and method for providing outside access to computer resources through a firewall. A firewall isolates computer and network resources inside the firewall from networks, computers and computer applications outside the firewall. Typically, the inside resources could be privately owned databases and local area networks (LAN's), and outside objects could include individuals and computer applications operating through public communication networks such as the Internet. Usually, a firewall allows for an inside user or object to originate connection to an outside object or network, but does not allow for connections to be generated in the reverse direction; i.e. from outside in. The system provides a special "tunneling" mechanism, operating on both sides of a firewall, for establishing such "outside in" connections when they are requested by certain "trusted" individuals or objects or applications outside the firewall. The intent here is to minimize the resources required for establishing "tunneled" connections (connections through the firewall that are effectively requested from outside), while also minimizing the security risk involved in permitting such connections to be made at all. The mechanism includes special tunneling applications, running on interface servers inside and outside the firewall, and a special table of "trusted sockets" created and maintained by the inside tunneling application. Entries in the trusted sockets table define objects inside the firewall consisting of special inside ports, a telecommunication protocol to be used at each port, and a host object associated with each port. Each entry is "trusted" in the sense that it is supposedly known only by individuals authorized to have "tunneling" access through the firewall from outside. These applications use the table to effect connections through the firewall in response to outside requests identifying valid table entries.

U.S. Pat. No. 5,968,176 (Nessett, et al., Oct. 19, 1999), expressly incorporated herein by reference, relates to a multilayer firewall system. A system provides for establishing security in a network that includes nodes having security functions operating in multiple protocol layers. Multiple network devices, such as remote access equipment, routers, switches, repeaters and network cards having security functions are configured to contribute to implementation of distributed firewall functions in the network. By distributing firewall functionality throughout many layers of the network in a variety of network devices, a pervasive firewall is implemented. The pervasive, multilayer firewall includes a policy definition component that accepts policy data that defines how the firewall should behave. The policy definition component can be a centralized component, or a component that is distributed over the network. The multilayer firewall also includes a collection of network devices that are used to enforce the defined policy. The security functions operating in this collection of network devices across multiple protocol layers are coordinated by the policy definition component so that particular devices enforce that part of the policy pertinent to their part of the network.

U.S. Pat. No. 5,983,350 (Minear, et al., Nov. 9, 1999), expressly incorporated herein by reference, relates to a secure firewall supporting different levels of authentication based on address or encryption status. A system and method is provided for regulating the flow of messages through a firewall having a network protocol stack, wherein the network protocol stack includes an Internet Protocol (IP) layer, the method comprising establishing a security policy, determining, at the IP layer, if a message is encrypted, if the message is not encrypted, passing the unencrypted message up the network protocol stack to an application level proxy, and if the message is encrypted, decrypting the message and passing the decrypted message up the network protocol stack to the application level proxy, wherein decrypting the message includes executing a process at the IP layer to decrypt the message.

U.S. Pat. No. 6,009,475 (Shrader, Dec. 28, 1999), expressly incorporated herein by reference, relates to a system and method for filter rule validation and administration for firewalls. Filter rules on a firewall between a secure computer network and a nonsecure computer network are validated from a user interface. A user interface is presented in which a test packet can be defined. The user interface includes controls for defining values for attributes of the test packet, wherein the attributes of the test packet are selected from a set of attributes of normal packets normally sent between the secure and nonsecure computer networks. A defined test packet is validated against a set of filter rules in the firewall or matched against the filter rules to determine those filter rules with matching attributes to the defined packet. When validating, responsive to the failure of the test packet in the validating step, the filter rule in the set of filter rules that denied the test packet is displayed.

U.S. Pat. No. 6,052,788 (Wesinger, Jr., et al., Apr. 18, 2000), expressly incorporated herein by reference, relates to a firewall, providing enhanced network security and user transparency, for improved network security and maximum user convenience. The firewall employs "envoys" that exhibit the security robustness of prior-art proxies and the transparency and ease-of-use of prior-art packet filters, combining the best of both worlds. No traffic can pass through the firewall unless the firewall has established an envoy for that traffic. Both connection-oriented (e.g., TCP) and connectionless (e.g., UDP-based) services may be handled using envoys. Establishment of an envoy may be subjected to a myriad of tests to "qualify" the user, the requested communication, or both. Therefore, a high level of security may be achieved. The usual added burden of prior-art proxy systems is avoided in such a way as to achieve full transparency—the user can use standard applications and need not even know of the existence of the firewall. To achieve full transparency, the firewall is configured as two or more sets of virtual hosts. The firewall is, therefore, "multi-homed," each home being independently configurable. One set of hosts responds to addresses on a first network interface of the firewall. Another set of hosts responds to addresses on a second network interface of the firewall. In one aspect, programmable transparency is achieved by establishing DNS mappings between remote hosts to be accessed through one of the network interfaces and respective virtual hosts on that interface. In another aspect, automatic transparency may be achieved using code for dynamically mapping remote hosts to virtual hosts in accordance with a technique referred to herein as dynamic DNS, or DDNS.

U.S. Pat. No. 6,061,797 (Jade, et al., May 9, 2000), expressly incorporated herein by reference, relates to a system and method for providing outside access to computer resources through a firewall. A firewall isolates computer and network resources inside the firewall from networks, computers and computer applications outside the firewall. Typically, the inside resources could be privately owned databases and local area networks (LAN's), and outside objects could include individuals and computer applications operating through public communication networks such as the Internet. Usually, a firewall allows for an inside user or object to originate connection to an outside object or network, but does not allow for connections to be generated in the reverse direction; i.e. from outside in. The system provides a special "tunneling" mechanism, operating on both sides of a firewall, for establishing such "outside in" connections when they are requested by certain "trusted" individuals or objects or applications outside the firewall. The intent here is to minimize the resources required for establishing "tunneled" connections (connections through the firewall that are effectively requested from outside), while also minimizing the security risk involved in permitting such connections to be made at all. The mechanism includes special tunneling applications, running on interface servers inside and outside the firewall, and a special table of "trusted sockets" created and maintained by the inside tunneling application. Entries in the trusted sockets table define objects inside the firewall consisting of special inside ports, a telecommunication protocol to be used at each port, and a host object associated with each port. Each entry is "trusted" in the sense that it is supposedly known only by individuals authorized to have "tunneling" access through the firewall from outside.

U.S. Pat. No. 6,061,798 (Coley, et al., May 9, 2000), expressly incorporated herein by reference, relates to a firewall system for protecting network elements connected to a public network. The firewall operates on a stand-alone computer connected between the public network and the network elements to be protected such that all access to the protected network elements must go through the firewall. The firewall application running on the stand-alone computer is preferably the only application running on that machine. The application includes a variety of proxy agents that are specifically assigned to an incoming request in accordance with the service protocol (i.e., port number) indicated in the incoming access request. An assigned proxy agent verifies the authority of an incoming request to access a network element indicated in the request. Once verified, the proxy agent completes the connection to the protected network element on behalf of the source of the incoming request.

See also, U.S. Pat. No. 6,075,860 (Apparatus and method for authentication and encryption of a remote terminal over a wireless link); U.S. Pat. No. 6,061,798 (Firewall system for protecting network elements connected to a public network); U.S. Pat. No. 6,061,797 (Outside access to computer resources through a firewall); U.S. Pat. No. 6,052,788 (Firewall providing enhanced network security and user transparency); U.S. Pat. No. 6,047,322 (Method and apparatus for quality of service management); U.S. Pat. No. 6,041,355 (Method for transferring data between a network of computers dynamically based on tag information); U.S. Pat. No. 6,012,088 (Automatic configuration for internet access device); U.S. Pat. No. 6,003,084 (Secure network proxy for connecting entities); U.S. Pat. No. 5,999,973 (Use of web technology for subscriber management activities); U.S. Pat. No. 5,991,731 (Method and system for interactive prescription and distribution of prescriptions in conducting clinical studies); U.S. Pat. No. 5,983,350 (Secure firewall supporting different levels of authentication based on address or encryption status); U.S. Pat. No. 5,968,176 (Multilayer firewall system); U.S. Pat. No. 5,960,177 (System for performing remote operation between firewall-equipped networks or devices); U.S. Pat. No. 5,958,016 (Internet-web link for access to intelligent network service control); U.S. Pat. No. 5,950,195 (Generalized security policy management system and method); U.S. Pat. No. 5,944,823 (Outside access to computer resources through a firewall); U.S. Pat. No. 5,928,333 (Electronic mail management system for operation on a host computer system); U.S. Pat. No. 5,918,227 (On-line directory service with a plurality of databases and processors); U.S. Pat. No. 5,915,087 (Transparent security proxy for unreliable message exchange protocols); U.S. Pat. No. 5,915,008 (System and method for changing advanced intelligent network services from customer premises equipment); U.S. Pat. No. 5,909,493 (Method and system for diagnosis and control of machines using connectionless modes of communication); U.S. Pat. No. 5,898,830 (Firewall providing enhanced network security and user transparency); U.S. Pat. No. 5,870,744 (Virtual people networking); U.S. Pat. No. 5,845,267 (System and method for billing for transactions conducted over the internet from within an intranet); U.S. Pat. No. 5,835,726 (System for securing the flow of and selectively modifying packets in a computer network); U.S. Pat. No. 5,826,029 (Secured gateway interface); U.S. Pat. No. 5,826,014 (Firewall system for protecting network elements connected to a public network); U.S. Pat. No. 5,812,398 (Method and system for escrowed backup of hotelled world wide web sites); U.S. Pat. No. 5,805,803 (Secure web tunnel); U.S. Pat. No. 5,784,463 (Token distribution, registration, and dynamic configuration of user entitlement for an application level security system and method); U.S. Pat. No. 5,632,011 (Electronic mail management system for operation on a host computer system); U.S. Pat. No. 5,623,601 (Apparatus and method for providing a secure gateway for communication and data exchanges between networks), each of which is expressly incorporated herein by reference.

Virtual Private Network

U.S. Pat. No. 6,079,020 (Liu, Jun. 20, 2000), expressly incorporated herein by reference, relates to a method and an apparatus for managing a virtual private network operating over a public data network. This public data network has been augmented to include a plurality of virtual private network gateways so that communications across the virtual private network are channeled through the virtual private network gateways. One embodiment includes a system that operates by receiving a command specifying an operation on the virtual private network. The system determines which virtual private network gateways are affected by the command. The system then automatically translates the command into configuration parameters for virtual private network gateways affected by the command. These configuration parameters specify how the virtual private network gateways handle communications between specific groups of addresses on the public data network. The system then transmits the configuration parameters to the virtual private network gateways affected by the command, so that the virtual private network gateways are configured to implement the command.

See also, U.S. Pat. No. 6,081,900 (Secure intranet access); U.S. Pat. No. 6,081,533 (Method and apparatus for an application interface module in a subscriber terminal unit); U.S. Pat. No. 6,079,020 (Method and apparatus for managing a virtual private network); U.S. Pat. No. 6,078,946 (System and method for management of connection oriented networks); U.S. Pat. No. 6,078,586 (ATM virtual private networks); U.S. Pat. No. 6,075,854 (Fully flexible routing service for an advanced intelligent network); U.S. Pat. No. 6,075,852 (Telecommunications system and method for processing call-independent signalling transactions); U.S. Pat. No. 6,073,172 (Initializing and reconfiguring a secure network interface); U.S. Pat. No. 6,061,796 (Multi-access virtual private network); U.S. Pat. No. 6,061,729 (Method and system for communicating service information in an advanced intelligent network); U.S. Pat. No. 6,058,303 (System and method for subscriber activity supervision); U.S. Pat. No. 6,055,575 (Virtual private network system and method); U.S. Pat. No. 6,052,788 (Firewall providing enhanced network security and user transparency); U.S. Pat. No. 6,047,325 (Network device for supporting construction of virtual local area networks on arbitrary local and wide area computer networks); U.S. Pat. No. 6,032,118 (Virtual private network service provider for asynchronous transfer mode network); U.S. Pat. No. 6,029,067 (Virtual private network for mobile subscribers); U.S. Pat. No. 6,016,318 (Virtual private network system over public mobile data network and virtual LAN); U.S. Pat. No. 6,009,430 (Method and system for provisioning databases in an advanced intelligent network); U.S. Pat. No. 6,005,859 (Proxy VAT-PSTN origination); U.S. Pat. No. 6,002,767 (System, method and article of manufacture for a modular gateway server architecture); U.S. Pat. No. 6,002,756 (Method and system for implementing intelligent telecommunication services utilizing self-sustaining, fault-tolerant object oriented architecture), each of which is expressly incorporated herein by reference.

Biometric Authentication

U.S. Pat. No. 5,193,855 (Shamos, Mar. 16, 1993, Patient and healthcare provider identification system), expressly incorporated herein by reference, relates to a patient and healthcare provider identification system which includes a database of patient and healthcare provider information including the identity of each patient and provider and some identification criteria (such as fingerprint data); a print scanner for reading the print information from a patient or provider; a control system for matching the print data read by the scanner with the print data stored in memory; and a printer for printing labels or generating stamps or other visually perceptible medium for positively identifying the patient or provider and creating a record of the identification.

U.S. Pat. No. 6,035,406 (Moussa, et al., Mar. 7, 2000), expressly incorporated herein by reference, relates to a plurality-factor security system. The method and system provide for simultaneously authenticating a user using two or more factors, such as both a password and a physical token or both a password and biometric information. The user presents a physical token including a storage device to a processor and attempts to log in using a first password; the processor includes a login service which receives the first password, accesses the storage device to transform the first password into a second password, and authenticates the second password using an operating system for the processor. The storage device includes encrypted information regarding the second password which can be relatively easily determined in response to the first password, but which cannot be relatively easily determined without the first password. The system or the storage device may also store information for biometric authentication of the user.

U.S. Pat. No. 6,052,468 (Hillhouse, Apr. 18, 2000), expressly incorporated herein by reference, relates to a method is disclosed for improving portability of secure encryption key data files. The method provides for re-securing key data files according to different security processes for mobility. For porting an encryption key secured using a fingerprint authentication process to a system having only a password authentication process, a user selects password authentication process, provides a fingerprint and is authorized, provides a new password and then the encryption key is accessed according to the fingerprint authentication process and secured according to the password authentication process. This allows the use of specialized security hardware at one location while retaining an ability to transport encryption keys in a secure fashion to other locations, which do not have similar security hardware. U.S. Pat. No. 6,052,468 therefore provides a system and method for increasing portability of secure access codes, by providing a system comprising a cryptographic key encrypted and stored in a key data file and a secured key for decrypting the cryptographic key wherein the secured key is stored in a secured fashion, a method of securing the secured key comprising the steps of a) accessing stored data associated with the secured key, the data indicative of an access method from a plurality of access methods for accessing the secured key; b) executing the indicated access method to access the secured key; c) selecting a method from the plurality of methods for securing the accessed secured key; d) securing the accessed secured key according to the selected access method; and, e) storing data associated with the secured key, the data indicative of the selected access method. The key may be secured by providing user authentication information; deriving from the user authentication information a second cryptographic key; encrypting the accessed secured key using the second cryptographic key; and the secured key is accessed by the steps of: providing user authentication information; deriving from the user authentication information a third cryptographic key; and, decrypting the secured key using the third cryptographic key. A method of accessing a secured cryptographic key is provided comprising the steps of: a) accessing data associated with the secured cryptographic key to determine an authorization method necessary to access the secured cryptographic key; b) providing user authorization information; and c) executing the determined authorization method to access the secured cryptographic key based on the user authorization information provided. A further method is provided for securing portable key data including encryption key information comprising the steps of: a) selecting a first authorization process from a plurality of authorization processes for securing the portable key data; b) authenticating access to the secured portable key data according to a different authorization process, removing the security from the portable key data; and c) implementing security of the portable key data according to the first authorization process.

U.S. Pat. No. 6,076,167 (Borza, Jun. 13, 2000), expressly incorporated herein by reference, relates to a method of enhancing network security for a communication session initiated between a first computer and a second other computer. From the first computer to the second computer in communications therewith a process for securing communications therebetween is transmitted. One such process is a biometric characterization process for characterizing fingerprints. The process is for execution on the second computer and is selected to be compatible therewith. Communications from the second computer to the first computer are secured using the transmitted process on the second computer and using, on the first computer, a compatible process to the transmitted process. The host computer can modify or replace the process or data particular to the process before each session, during a session, or at intervals.

See also, U.S. Pat. Nos. 6,081,900 (Secure intranet access); U.S. Pat. No. 6,081,750 (Ergonomic man-machine interface incorporating adaptive pattern recognition based control system); U.S. Pat. No. 6,081,199 (Locking device for systems access to which is time-restricted); U.S. Pat. No. 6,079,621 (Secure card for E-commerce and identification); U.S. Pat. No. 6,078,265 (Fingerprint identification security system); U.S. Pat. No. 6,076,167 (Method and system for improving security in network applications); U.S. Pat. No. 6,075,455 (Biometric time and attendance system with epidermal topographical updating capability); U.S. Pat. No. 6,072,894 (Biometric face recognition for applicant screening); U.S. Pat. No. 6,070,141 (System and method of assessing the quality of an identification transaction using an identification quality score); U.S. Pat. No. 6,068,184 (Security card and system for use thereof); U.S. Pat. No. 6,064,751 (Document and signature data capture system and method); U.S. Pat. No. 6,056,197 (Information recording method for preventing alteration, information recording apparatus, and information recording medium); U.S. Pat. No. 6,052,468 (Method of securing a cryptographic key); U.S. Pat. No. 6,045,039 (Cardless automated teller transactions); U.S. Pat. No. 6,044,349 (Secure and convenient information storage and retrieval method and apparatus); U.S. Pat. No. 6,044,155 (Method and system for securely archiving core data secrets); U.S. Pat. No. 6,041,410 (Personal identification fob); U.S. Pat. No. 6,040,783 (System and method for remote, wireless positive identity verification); U.S. Pat. No. 6,038,666 (Remote identity verification technique using a personal identification device); U.S. Pat. No. 6,038,337 (Method and apparatus for object recognition); U.S. Pat. No. 6,038,315 (Method and system for normalizing biometric variations to authenticate users from a public database and that ensures individual biometric data privacy); U.S. Pat. No. 6,037,870 (Detector system for access control, and a detector assembly for implementing such a system); U.S. Pat. No. 6,035,406 (Plurality-factor security system); U.S. Pat. No. 6,035,402 (Virtual certificate authority); U.S. Pat. No. 6,035,398 (Cryptographic key generation using biometric data); U.S. Pat. No. 6,031,910 (Method and system for the secure transmission and storage of protectable information); U.S. Pat. No. 6,026,166 (Digitally certifying a user identity and a computer system in combination); U.S. Pat. No. 6,018,739 (Biometric personnel identification system); U.S. Pat. No. 6,016,476 (Portable information and transaction processing system and method utilizing biometric authorization and digital certificate security); U.S. Pat. No. 6,012,049 (System for performing financial transactions using a smartcard); U.S. Pat. No. 6,012,039 (Tokenless biometric electronic rewards system); U.S. Pat. No. 6,011,858 (Memory card having a biometric template stored thereon and system for using same); U.S. Pat. No. 6,009,177 (Enhanced cryptographic system and method with key escrow feature); U.S. Pat. No. 6,006,328 (Computer software authentication, protection, and security system); U.S. Pat. No. 6,003,135 (Modular security device); U.S. Pat. No. 6,002,770 (Method for secure data transmission between remote stations); U.S. Pat. No. 5,999,637 (Individual identification apparatus for selectively recording a reference pattern based on a correlation with comparative patterns); U.S. Pat. No. 5,999,095 (Electronic security system); U.S. Pat. No. 5,995,630 (Biometric input with encryption); U.S. Pat. No. 5,991,431 (Mouse adapted to scan biometric data); U.S. Pat. No. 5,991,429 (Facial recognition system for security access and identification); U.S. Pat. No. 5,991,408 (Identification and security using biometric measurements); U.S. Pat. No. 5,987,155 (Biometric input device with peripheral port); U.S. Pat. No. 5,987,153 (Automated verification and prevention of spoofing for biometric data); U.S. Pat. No. 5,986,746 (Topographical object detection system); U.S. Pat. No. 5,984,366 (Unalterable self-verifying articles); U.S. Pat. No. 5,982,894 (System including separable protected components and associated methods); U.S. Pat. No. 5,979,773 (Dual smart card access control electronic data storage and retrieval system and methods); U.S. Pat. No. 5,978,494 (Method of selecting the best enroll image for personal identification); U.S. Pat. No. 5,974,146 (Real time bank-centric universal payment system); U.S. Pat. No. 5,970,143 (Remote-auditing of computer generated outcomes, authenticated billing and access control, and software metering system using cryptographic and other protocols); U.S. Pat. No. 5,966,446 (Time-bracketing infrastructure implementation); U.S. Pat. No. 5,963,908 (Secure logon to notebook or desktop computers); U.S. Pat. No. 5,963,657 (Economical skin-pattern-acquisition and analysis apparatus for access control; systems controlled thereby); U.S. Pat. No. 5,954,583 (Secure access control system); U.S. Pat. No. 5,952,641 (Security device for controlling the access to a personal computer or to a computer terminal); U.S. Pat. No. 5,951,055 (Security document containing encoded data block); U.S. Pat. No. 5,949,881 (Apparatus and method for cryptographic companion imprinting); U.S. Pat. No. 5,949,879 (Auditable security system for the generation of cryptographically protected digital data); U.S. Pat. No. 5,949,046 (Apparatus for issuing integrated circuit cards); U.S. Pat. No. 5,943,423 (Smart token system for secure electronic transactions and identification); U.S. Pat. No. 5,935,071 (Ultrasonic biometric imaging and identity verification system); U.S. Pat. No. 5,933,515 (User identification through sequential input of fingerprints); U.S. Pat. No. 5,933,498 (System for controlling access and distribution of digital property); U.S. Pat. No. 5,930,804 (Web-based biometric authentication system and method); U.S. Pat. No. 5,923,763 (Method and apparatus for secure document timestamping); U.S. Pat. No. 5,920,477 (Human factored interface incorporating adaptive pattern recognition based controller apparatus); U.S. Pat. No. 5,920,384 (Optical imaging device); U.S. Pat. No. 5,920,058 (Holographic labeling and reading machine for authentication and security applications); U.S. Pat. No. 5,915,973 (System for administration of remotely-proctored, secure examinations and methods therefor); U.S. Pat. No. 5,913,196 (System and method for establishing identity of a speaker); U.S. Pat. No. 5,913,025 (Method and apparatus for proxy authentication); U.S. Pat. No. 5,912,974 (Apparatus and method for authentication of printed documents); U.S. Pat. No. 5,912,818 (System for tracking and dispensing medical items); U.S. Pat. No. 5,910,988 (Remote image capture with centralized processing and storage); U.S. Pat. No. 5,907,149 (Identification card with delimited usage); U.S. Pat. No. 5,901,246 (Ergonomic man-machine interface incorporating adaptive pattern recognition based control system); U.S. Pat. No. 5,898,154 (System and method for updating security information in a time-based electronic monetary system); U.S. Pat. No. 5,897,616 (Apparatus and methods for speaker verification/identification/classification employing non-acoustic and/or acoustic models and databases); U.S. Pat. No. 5,892,902 (Intelligent token protected system with network authentication); U.S. Pat. No. 5,892,838 (Biometric recognition using a classification neural network); U.S. Pat. No. 5,892,824 (Signature capture/verification systems and methods); U.S. Pat. No. 5,890,152 (Personal feedback browser for obtaining media files); U.S. Pat. No. 5,889,474 (Method and apparatus for transmitting subject status information over a wireless communications network); U.S. Pat. No. 5,881,226 (Computer security system); U.S. Pat. No. 5,878,144 (Digital certificates containing multimedia data extensions); U.S. Pat. No. 5,876,926 (Method, apparatus and system for verification of human medical data); U.S. Pat. No. 5,875,108 (Ergonomic man-machine interface incorporating adaptive pattern recognition based control system); U.S. Pat. No. 5,872,849 (Enhanced cryptographic system and method with key escrow feature); U.S. Pat. No. 5,872,848 (Method and apparatus for witnessed authentication of electronic documents); U.S. Pat. No. 5,872,834 (Telephone with biometric sensing device); U.S. Pat. No. 5,870,723 (Tokenless biometric transaction authorization method and system); U.S. Pat. No. 5,869,822 (Automated fingerprint identification system); U.S. Pat. No. 5,867,802 (Biometrically secured control system for preventing the unauthorized use of a vehicle); U.S. Pat. No. 5,867,795 (Portable electronic device with transceiver and visual image display); U.S. Pat. No. 5,867,578 (Adaptive multi-step digital signature system and method of operation thereof); U.S. Pat. No. 5,862,260 (Methods for surveying dissemination of proprietary empirical data); U.S. Pat. No. 5,862,246 (Knuckle profile identity verification system); U.S. Pat. No. 5,862,223 (Method and apparatus for a cryptographically-assisted commercial network system designed to facilitate and support expert-based commerce); U.S. Pat. No. 5,857,022 (Enhanced cryptographic system and method with key escrow feature); U.S. Pat. No. 5,850,451 (Enhanced cryptographic system and method with key escrow feature); U.S. Pat. No. 5,850,442 (Secure world wide electronic commerce over an open network); U.S. Pat. No. 5,848,231 (System configuration contingent upon secure input); U.S. Pat. No. 5,844,244 (Portable identification carrier); U.S. Pat. No. 5,841,907 (Spatial integrating optical correlator for verifying the authenticity of a person, product or thing); U.S. Pat. No. 5,841,886 (Security system for photographic identification); U.S. Pat. No. 5,841,865 (Enhanced cryptographic system and method with key escrow feature); U.S. Pat. No. 5,841,122 (Security structure with electronic smart card access thereto with transmission of power and data between the smart card and the smart card reader performed capacitively or inductively); U.S. Pat. No. 5,838,812 (Tokenless biometric transaction authorization system); U.S. Pat. No. 5,832,464 (System and method for efficiently processing payments via check and electronic funds transfer); U.S. Pat. No. 5,832,119 (Methods for controlling systems using control signals embedded in empirical data); U.S. Pat. No. 5,828,751 (Method and apparatus for secure measurement certification); U.S. Pat. No. 5,825,880 (Multi-step digital signature method and system); U.S. Pat. No. 5,825,871 (Information storage device for storing personal identification information); U.S. Pat. No. 5,815,577 (Methods and apparatus for securely encrypting data in conjunction with a personal computer); U.S. Pat. No. 5,815,252 (Biometric identification process and system utilizing multiple parameters scans for reduction of false negatives); U.S. Pat. No. 5,805,719 (Tokenless identification of individuals); U.S. Pat. No. 5,802,199 (Use sensitive identification system); U.S. Pat. No. 5,799,088 (Non-deterministic public key encryption system); U.S. Pat. No. 5,799,086 (Enhanced cryptographic system and method with key escrow feature); U.S. Pat. No. 5,799,083 (Event verification system); U.S. Pat. No. 5,790,674 (System and method of providing system integrity and positive audit capabilities to a positive identification system); U.S. Pat. No. 5,790,668 (Method and apparatus for securely handling data in a database of biometrics and associated data); U.S. Pat. No. 5,789,733 (Smart card with contactless optical interface); U.S. Pat. No. 5,787,187 (Systems and methods for biometric identification using the acoustic properties of the ear canal); U.S. Pat. No. 5,784,566 (System and method for negotiating security services and algorithms for communication across a computer network); U.S. Pat. No. 5,784,461 (Security system for controlling access to images and image related services); U.S. Pat. No. 5,774,551 (Pluggable account management interface with unified login and logout and multiple user authentication services); U.S. Pat. No. 5,771,071 (Apparatus for coupling multiple data sources onto a printed document); U.S. Pat. No. 5,770,849 (Smart card device with pager and visual image display); U.S. Pat. No. 5,768,382 (Remote-auditing of computer generated outcomes and authenticated billing and access control system using cryptographic and other protocols); U.S. Pat. No. 5,767,496 (Apparatus for processing symbol-encoded credit card information); U.S. Pat. No. 5,764,789 (Tokenless biometric ATM access system); U.S. Pat. No. 5,763,862 (Dual card smart card reader); U.S. Pat. No. 5,761,298 (Communications headset with universally adaptable receiver and voice transmitter); U.S. Pat. No. 5,757,916 (Method and apparatus for authenticating the location of remote users of networked computing systems); U.S. Pat. No. 5,757,431 (Apparatus for coupling multiple data sources onto a printed document); U.S. Pat. No. 5,751,836 (Automated, non-invasive iris recognition system and method); U.S. Pat. No. 5,751,809 (Apparatus and method for securing captured data transmitted between two sources); U.S. Pat. No. 5,748,738 (System and method for electronic transmission, storage and retrieval of authenticated documents); U.S. Pat. No. 5,745,573 (System and method for controlling access to a user secret); U.S. Pat. No. 5,745,555 (System and method using personal identification numbers and associated prompts for controlling unauthorized use of a security device and unauthorized access to a resource); U.S. Pat. No. 5,742,685 (Method for verifying an identification card and recording verification of same); U.S. Pat. No. 5,742,683 (System and method for managing multiple users with different privileges in an open metering system); U.S. Pat. No. 5,737,420 (Method for secure data transmission between remote stations); U.S. Pat. No. 5,734,154 (Smart card with integrated reader and visual image display); U.S. Pat. No. 5,719,950 (Biometric, personal authentication system); U.S. Pat. No. 5,712,914 (Digital certificates containing multimedia data extensions); U.S. Pat. No. 5,712,912 (Method and apparatus for securely handling a personal identification number or cryptographic key using biometric techniques); U.S. Pat. No. 5,706,427 (Authentication method for networks); U.S. Pat. No. 5,703,562 (Method for transferring data from an unsecured computer to a secured computer); U.S. Pat. No. 5,696,827 (Secure cryptographic methods for electronic transfer of information); U.S. Pat. No. 5,682,142 (Electronic control system/network); U.S. Pat. No. 5,682,032 (Capacitively coupled identity verification and escort memory apparatus); U.S. Pat. No. 5,680,460 (Biometric controlled key generation); U.S. Pat. No. 5,668,878 (Secure cryptographic methods for electronic transfer of information); U.S. Pat. No. 5,666,400 (Intelligent recognition); U.S. Pat. No. 5,659,616 (Method for securely using digital signatures in a commercial cryptographic system); U.S. Pat. No. 5,647,364 (Ultrasonic biometric imaging and identity verification system); U.S. Pat. No. 5,647,017 (Method and system for the verification of handwritten signatures); U.S. Pat. No. 5,646,839 (Telephone-based personnel tracking system); U.S. Pat. No. 5,636,282 (Method for dial-in access security using a multimedia modem); U.S. Pat. No. 5,633,932 (Apparatus and method for preventing disclosure through user-authentication at a printing node); U.S. Pat. No. 5,615,277 (Tokenless security system for authorizing access to a secured computer system); U.S. Pat. No. 5,613,012 (Tokenless identification system for authorization of electronic transactions and electronic transmissions); U.S. Pat. No. 5,608,387 (Personal identification devices and access control systems); U.S. Pat. No. 5,594,806 (Knuckle profile identity verification system); U.S. Pat. No. 5,592,408 (Identification card and access control device); U.S. Pat. No. 5,588,059 (Computer system and method for secure remote communication sessions); U.S. Pat. No. 5,586,171 (Selection of a voice recognition data base responsive to video data); U.S. Pat. No. 5,583,950 (Method and apparatus for flash correlation); U.S. Pat. No. 5,583,933 (Method and apparatus for the secure communication of data); U.S. Pat. No. 5,578,808 (Data card that can be used for transactions involving separate card issuers); U.S. Pat. No. 5,572,596 (Automated, non-invasive iris recognition system and method); U.S. Pat. No. 5,561,718 (Classifying faces); U.S. Pat. No. 5,559,885 (Two stage read-write method for transaction cards); U.S. Pat. No. 5,557,765 (System and method for data recovery); U.S. Pat. No. 5,553,155 (Low cost method employing time slots for thwarting fraud in the periodic issuance of food stamps, unemployment benefits or other governmental human services); U.S. Pat. No. 5,544,255 (Method and system for the capture, storage, transport and authentication of handwritten signatures); U.S. Pat. No. 5,534,855 (Method and system for certificate based alias detection); U.S. Pat. No. 5,533,123 (Programmable distributed personal security); U.S. Pat. No. 5,526,428 (Access control apparatus and method); U.S. Pat. No. 5,523,739 (Metal detector for control of access combined in an integrated form with a transponder detector); U.S. Pat. No. 5,497,430 (Method and apparatus for image recognition using invariant feature signals); U.S. Pat. No. 5,485,519 (Enhanced security for a secure token code); U.S. Pat. No. 5,485,312 (Optical pattern recognition system and method for verifying the authenticity of a person, product or thing); U.S. Pat. No. 5,483,601 (Apparatus and method for biometric identification using silhouette and displacement images of a portion of a person's hand); U.S. Pat. No. 5,478,993 (Process as safety concept against unauthorized use of a payment instrument in cashless payment at payment sites); U.S. Pat. No. 5,475,839 (Method and structure for securing access to a computer system); U.S. Pat. No. 5,469,506 (Apparatus for verifying an identification card and identifying a person by means of a biometric characteristic); U.S. Pat. No. 5,457,747 (Anti-fraud verification system using a data card); U.S. Pat. No. 5,455,407 (Electronic-monetary system); U.S. Pat. No. 5,453,601 (Electronic-monetary system); U.S. Pat. No. 5,448,045 (System for protecting computers via intelligent tokens or smart cards); U.S. Pat. No. 5,432,864 (Identification card verification system); U.S. Pat. No. 5,414,755 (System and method for passive voice verification in a telephone network); U.S. Pat. No. 5,412,727 (Anti-fraud voter registration and voting system using a data card); U.S. Pat. No. 5,363,453 (Non-minutiae automatic fingerprint identification system and methods); U.S. Pat. No. 5,347,580 (Authentication method and system with a smartcard); U.S. Pat. No. 5,345,549 (Multimedia based security systems); U.S. Pat. No. 5,341,428 (Multiple cross-check document verification system); U.S. Pat. No. 5,335,288 (Apparatus and method for biometric identification); U.S. Pat. No. 5,291,560 (Biometric personal identification system based on iris analysis); U.S. Pat. No. 5,283,431 (Optical key security access system); U.S. Pat. No. 5,280,527 (Biometric token for authorizing access to a host system); U.S. Pat. No. 5,272,754 (Secure computer interface); U.S. Pat. No. 5,245,329 (Access control system with mechanical keys which store data); U.S. Pat. No. 5,229,764 (Continuous biometric authentication matrix); U.S. Pat. No. 5,228,094 (Process of identifying and authenticating data characterizing an individual); U.S. Pat. No. 5,224,173 (Method of reducing fraud in connection with employment, public license applications, social security, food stamps, welfare or other government benefits); U.S. Pat. No. 5,208,858 (Method for allocating useful data to a specific originator); U.S. Pat. No. 5,204,670 (Adaptable electric monitoring and identification system); U.S. Pat. No. 5,191,611 (Method and apparatus for protecting material on storage media and for transferring material on storage media to various recipients); U.S. Pat. No. 5,163,094 (Method for identifying individuals from analysis of elemental shapes derived from biosensor data); U.S. Pat. No. 5,155,680 (Billing system for computing software); U.S. Pat. No. 5,131,038 (Portable authentification system); U.S. Pat. No. 5,073,950 (Finger profile identification system); U.S. Pat. No. 5,067,162 (Method and apparatus for verifying identity using image correlation); U.S. Pat. No. 5,065,429 (Method and apparatus for protecting material on storage media); U.S. Pat. No. 5,056,147 (Recognition procedure and an apparatus for carrying out the recognition procedure); U.S. Pat. No. 5,056,141 (Method and apparatus for the identification of personnel); U.S. Pat. No. 5,036,461 (Two-way authentication system between user's smart card and issuer-specific plug-in application modules in multi-issued transaction device); U.S. Pat. No. 5,020,105 (Field initialized authentication system for protective security of electronic information networks); U.S. Pat. No. 4,993,068 (Unforgettable personal identification system); U.S. Pat. No. 4,972,476 (Counterfeit proof ID card having a scrambled facial image); U.S. Pat. No. 4,961,142 (Multi-issuer transaction device with individual identification verification plug-in application modules for each issuer); U.S. Pat. No. 4,952,928 (Adaptable electronic monitoring and identification system); U.S. Pat. No. 4,941,173 (Device and method to render secure the transfer of data between a videotex terminal and a server); U.S. Pat. No. 4,926,480 (Card-computer moderated systems); U.S. Pat. No. 4,896,363 (Apparatus and method for matching image characteristics such as fingerprint minutiae); U.S. Pat. No. 4,890,323 (Data communication systems and methods); U.S. Pat. No. 4,868,376 (Intelligent portable interactive personal data system); U.S. Pat. No. 4,827,518 (Speaker verification system using integrated circuit cards); U.S. Pat. No. 4,819,267 (Solid state key for controlling access to computer systems and to computer software and/or for secure communications); U.S. Pat. No. 4,752,676 (Reliable secure, updatable "cash" card system); U.S. Pat. No. 4,736,203 (3D hand profile identification apparatus); U.S. Pat. No. 4,731,841 (Field initialized authentication system for protective security of electronic information networks); U.S. Pat. No. 4,564,018 (Ultrasonic system for obtaining ocular measurements), each of which is expressly incorporated herein by reference.

Content-Based Query Servers

U.S. Pat. No. 5,987,459 (Swanson, et al. Nov. 16, 1999), expressly incorporated herein by reference, relates to an image and document management system for content-based retrieval support directly into the compressed files. The system minimizes a weighted sum of the expected size of the compressed files and the expected query response time. Object searching of documents stored by the system is possible on a scalable resolution basis. The system includes a novel object representation based on embedded prototypes that provides for high-quality browsing of retrieval images at low bit rates.

U.S. Pat. No. 6,038,560 (Wical, Mar. 14, 2000), expressly incorporated herein by reference, relates to a concept knowledge base search and retrieval system, which includes factual knowledge base queries and concept knowledge base queries, is disclosed. A knowledge base stores associations among terminology/categories that have a lexical, semantic or usage association. Document theme vectors identify the content of documents through themes as well as through classification of the documents in categories that reflects what the documents are primarily about. The factual knowledge base queries identify, in response to an input query, documents relevant to the input query through expansion of the query terms as well as through expansion of themes. The concept knowledge base query does not identify specific documents in response to a query, but specifies terminology that identifies the potential existence of documents in a particular area.

U.S. Pat. No. 6,067,466 (Selker, et al., May 23, 2000), expressly incorporated herein by reference, relates to a diagnostic tool using a predictive instrument. A method is provided for evaluating a medical condition of a patient including the steps of monitoring one or more clinical features of a patient; based on the monitored features, computing a primary probability of a medical outcome or diagnosis; computing a plurality of conditional probabilities for a selected diagnostic test, the computed conditional probabilities including a first probability of the medical outcome or diagnosis assuming the selected diagnostic test produces a first outcome and a second probability of the medical outcome or diagnosis assuming the selected diagnostic test produces a second outcome; and displaying the computed primary probability as well as the plurality of computed conditional probabilities to a user as an aid to determining whether to administer the selected diagnostic test to the patient.

Jurisdictional Processing Dependence

U.S. Pat. No. 6,064,968 (Schanz, May 16, 2000), expressly incorporated herein by reference, relates to systems, methods and computer program products for identifying unique and common legal requirements for a regulated activity among multiple legal jurisdictions. Systems, methods and computer program products facilitate user compliance with laws that pertain to a regulated activity in each of a plurality of legal jurisdictions. A user selects, via a user interface in communication with a data processing system, a component that relates to an aspect of the regulated activity. A user also selects, via a user interface in communication with the data processing system, first and second legal jurisdictions from the plurality of legal jurisdictions. In response to the user selections, elements of the selected component that are unique and common to the first and second legal jurisdictions are displayed. Each displayed element is a legal requirement associated with the regulated activity as defined by laws of a respective legal jurisdiction.

E-Commerce Systems

U.S. Pat. No. 5,946,669 (Polk, Aug. 31, 1999), expressly incorporated herein by reference, relates to a method and apparatus for payment processing using debit-based electronic funds transfer and disbursement processing using addendum-based electronic data interchange. This disclosure describes a payment and disbursement system, wherein an initiator authorizes a payment and disbursement to a collector and the collector processes the payment and disbursement through an accumulator agency. The accumulator agency processes the payment as a debit-based transaction and processes the disbursement as an addendum-based transaction. The processing of a debit-based transaction generally occurs by electronic funds transfer (EFT) or by financial electronic data interchange (FEDI). The processing of an addendum-based transaction generally occurs by electronic data interchange (EDI).

U.S. Pat. No. 6,005,939 (Fortenberry, et al., Dec. 21, 1999), expressly incorporated herein by reference, relates to a method and apparatus for storing an Internet user's identity and access rights to World Wide Web resources. A method and apparatus for obtaining user information to conduct secure transactions on the Internet without having to re-enter the information multiple times is described. The method and apparatus can also provide a technique by which secured access to the data can be achieved over the Internet. A passport containing user-defined information at various security levels is stored in a secure server apparatus, or passport agent, connected to computer network. A user process instructs the passport agent to release all or portions of the passport to a recipient node and forwards a key to the recipient node to unlock the passport information.

U.S. Pat. No. 6,016,484 (Williams, et al., Jan. 18, 2000), expressly incorporated herein by reference, relates to a system, method and apparatus for network electronic payment instrument and certification of payment and credit collection utilizing a payment. An electronic monetary system provides for transactions utilizing an electronic-monetary system that emulates a wallet or a purse that is customarily used for keeping money, credit cards and other forms of payment organized. Access to the instruments in the wallet or purse is restricted by a password to avoid unauthorized payments. A certificate form must be completed in order to obtain an instrument. The certificate form obtains the information necessary for creating a certificate granting authority to utilize an instrument, a payment holder and a complete electronic wallet. Electronic approval results in the generation of an electronic transaction to complete the order. If a user selects a particular certificate, a particular payment instrument holder will be generated based on the selected certificate. In addition, the issuing agent for the certificate defines a default bitmap for the instrument associated with a particular certificate, and the default bitmap will be displayed when the certificate definition is completed. Finally, the number associated with a particular certificate will be utilized to determine if a particular party can issue a certificate.

U.S. Pat. No. 6,029,150 (Kravitz, Feb. 22, 2000), expressly incorporated herein by reference, relates to a system and method of payment in an electronic payment system wherein a plurality of customers have accounts with an agent. A customer obtains an authenticated quote from a specific merchant, the quote including a specification of goods and a payment amount for those goods. The customer sends to the agent a single communication including a request for payment of the payment amount to the specific merchant and a unique identification of the customer. The agent issues to the customer an authenticated payment advice based only on the single communication and secret shared between the customer and the agent and status information, which the agent knows about the merchant, and/or the customer. The customer forwards a portion of the payment advice to the specific merchant. The specific merchant provides the goods to the customer in response to receiving the portion of the payment advice.

U.S. Pat. No. 6,047,269 (Biffar, Apr. 4, 2000), expressly incorporated herein by reference, relates to a self-contained payment system with creating and facilitating transfer of circulating digital vouchers representing value. A digital voucher has an identifying element and a dynamic log. The identifying element includes information such as the transferable value, a serial number and a digital signature. The dynamic log records the movement of the voucher through the system and accordingly grows over time. This allows the system operator to not only reconcile the vouchers before redeeming them, but also to recreate the history of movement of a voucher should an irregularity like a duplicate voucher be detected. These vouchers are used within a self-contained system including a large number of remote devices that are linked to a central system. The central system can e linked to an external system. The external system, as well as the remote devices, is connected to the central system by any one or a combination of networks. The networks must be able to transport digital information, for example the Internet, cellular networks, telecommunication networks, cable networks or proprietary networks. Vouchers can also be transferred from one remote device to another remote device. These remote devices can communicate through a number of methods with each other. For example, for a non-face-to-face transaction the Internet is a choice, for a face-to-face or close proximity transactions tone signals or light signals are likely methods. In addition, at the time of a transaction a digital receipt can be created which will facilitate a fast replacement of vouchers stored in a lost remote device.

Micropayments

U.S. Pat. No. 5,999,919 (Jarecki, et al., Dec. 7, 1999), expressly incorporated herein by reference, relates to an efficient micropayment system. Existing software proposals for electronic payments can be divided into "on-line" schemes which require participation of a trusted party (the bank) in every transaction and are secure against overspending, and "off-line" schemes which do not require a third party and guarantee only that overspending is detected when vendors submit their transaction records to the bank (usually at the end of the day). A new "hybrid" scheme is proposed which combines the advantages of both "on-line" and "off-line" electronic payment schemes. It allows for control of overspending at a cost of only a modest increase in communication compared to the off-line schemes. The protocol is based on probabilistic polling. During each transaction, with some small probability, the vendor forwards information about this transaction to the bank. This enables the bank to maintain an accurate approximation of a customer's spending. The frequency of polling messages is related to the monetary value of transactions and the amount of overspending the bank is willing to risk. For transactions of high monetary value, the cost of polling approaches that of the on-line schemes, but for micropayments, the cost of polling is a small increase over the traffic incurred by the off-line schemes.

Micropayments are often preferred where the amount of the transaction does not justify the costs of complete financial security. In the micropayment scheme, typically a direct communication between creditor and debtor is not required; rather, the transaction produces a result which eventually results in an economic transfer, but which may remain outstanding subsequent to transfer of the underlying goods or services. The theory underlying this micropayment scheme is that the monetary units are small enough such that risks of failure in transaction closure is relatively insignificant for both parties, but that a user gets few chances to default before credit is withdrawn. On the other hand, the transaction costs of a non-real time transactions of small monetary units are substantially less than those of secure, unlimited or potentially high value, real time verified transactions, allowing and facilitating such types of commerce. Thus, the rights management system may employ applets local to the client system, which communicate with other applets and/or the server and/or a vendor/rights-holder to validate a transaction, at low transactional costs.

The following U.S. Patents, expressly incorporated herein by reference, define aspects of micropayment, digital certificate, and on-line payment systems: U.S. Pat. No. 5,930,777 (Barber, Jul. 27, 1999, Method of charging for pay-per-access information over a network); U.S. Pat. No. 5,857,023 (Jan. 5, 1999, Demers et al., Space efficient method of redeeming electronic payments); U.S. Pat. No. 5,815,657 (Sep. 29, 1998, Williams, System, method and article of manufacture for network electronic authorization utilizing an authorization instrument); U.S. Pat. No. 5,793,868 (Aug. 11, 1998, Micali, Certificate revocation system), U.S. Pat. No. 5,717,757 (Feb. 10, 1998, Micali, Certificate issue lists); U.S. Pat. No. 5,666,416 (Sep. 9, 1997, Micali, Certificate revocation system); U.S. Pat. No. 5,677,955 (Doggett et al., Electronic funds transfer instruments); U.S. Pat. No. 5,839,119 (Nov. 17, 1998, Krsul; et al., Method of electronic payments that prevents double-spending); U.S. Pat. No. 5,915,093 (Berlin et al.); U.S. Pat. No. 5,937,394 (Wong, et al.); U.S. Pat. No. 5,933,498 (Schneck et al.); U.S. Pat. No. 5,903,880 (Biffar); U.S. Pat. No. 5,903,651 (Kocher); U.S. Pat. No. 5,884,277 (Khosla); U.S. Pat. No. 5,960,083 (Sep. 28, 1999, Micali, Certificate revocation system); U.S. Pat. No. 5,963,924 (Oct. 5, 1999, Williams et al., System, method and article of manufacture for the use of payment instrument holders and payment instruments in network electronic commerce); U.S. Pat. No. 5,996,076 (Rowney et al., System, method and article of manufacture for secure digital certification of electronic commerce); U.S. Pat. No. 6,016,484 (Jan. 18, 2000, Williams et al., System, method and article of manufacture for network electronic payment instrument and certification of payment and credit collection utilizing a payment); U.S. Pat. No. 6,018,724 (Arent); U.S. Pat. No. 6,021,202 (Anderson et al., Method and system for processing electronic documents); U.S. Pat. No. 6,035,402 (Vaeth et al.); U.S. Pat. No. 6,049,786 (Smorodinsky); U.S. Pat. No. 6,049,787 (Takahashi, et al.); U.S. Pat. No. 6,058,381 (Nelson, Many-to-many payments system for network content materials); U.S. Pat. No. 6,061,448 (Smith, et al.); U.S. Pat. No. 5,987,132 (Nov. 16, 1999, Rowney, System, method and article of manufacture for conditionally accepting a payment method utilizing an extensible, flexible architecture); U.S. Pat. Nos. 6,057,872 (Candelore); and 6,061,665 (May 9, 2000, Bahreman, System, method and article of manufacture for dynamic negotiation of a network payment framework). See also, Rivest and Shamir, "PayWord and MicroMint: Two Simple Micropayment Schemes" (May 7, 1996); Micro PAYMENT transfer Protocol (MPTP) Version 0.1 (Nov. 22, 1995) et seq., http://www.w3.org/pub/WWW/TR/WD-mptp; Common Markup for web Micropayment Systems, http://www.w3.org/TR/WD-Micropayment-Markup (Jun. 9, 1999); "Distributing Intellectual Property: a Model of Microtransaction Based Upon Metadata and Digital Signatures", Olivia, Maurizio, http://olivia.modlang.denison.edu/~olivia/RFC/09/, all of which are expressly incorporated herein by reference.

See, also: U.S. Pat. No. 4,977,595 (Dec. 11, 1990, Method and apparatus for implementing electronic cash); U.S. Pat. No. 5,224,162 (Jun. 29, 1993, Electronic cash system); U.S.

Pat. No. 5,237,159 (Aug. 17, 1993, Electronic check presentment system); U.S. Pat. No. 5,392,353 (February, 1995, Morales, TV Answer, Inc. Interactive satellite broadcast network); U.S. Pat. No. 5,511,121 (Apr. 23, 1996, Efficient electronic money); U.S. Pat. No. 5,621,201 (April, 1997, Langhans et al., Visa International Automated purchasing control system); U.S. Pat. No. 5,623,547 (Apr. 22, 1997, Value transfer system); U.S. Pat. No. 5,679,940 (October, 1997, Templeton et al., TeleCheck International, Inc. Transaction system with on/off line risk assessment); U.S. Pat. No. 5,696,908 (December, 1997, Muehlberger et al., Southeast Phonecard, Inc. Telephone debit card dispenser and method); 5,754,939 (May 1998, Herz et al., System for generation of user profiles for a system for customized electronic identification of desirable objects); U.S. Pat. No. 5,768,385 (Jun. 16, 1998, Untraceable electronic cash); U.S. Pat. No. 5,799,087 (Aug. 25, 1998, Electronic-monetary system); U.S. Pat. No. 5,812,668 (Sep. 22, 1998, System, method and article of manufacture for verifying the operation of a remote transaction clearance system utilizing a multichannel, extensible, flexible architecture); U.S. Pat. No. 5,828,840 (Oct. 27, 1998, Server for starting client application on client if client is network terminal and initiating client application on server if client is non network terminal); U.S. Pat. No. 5,832,089 (Nov. 3, 1998, Off-line compatible electronic cash method and system); U.S. Pat. No. 5,850,446 (Dec. 15, 1998, System, method and article of manufacture for virtual point of sale processing utilizing an extensible, flexible architecture); U.S. Pat. No. 5,889,862 (Mar. 30, 1999, Method and apparatus for implementing traceable electronic cash); U.S. Pat. No. 5,889,863 (Mar. 30, 1999, System, method and article of manufacture for remote virtual point of sale processing utilizing a multichannel, extensible, flexible architecture); U.S. Pat. No. 5,898,154 (Apr. 27, 1999, System and method for updating security information in a time-based electronic monetary system); U.S. Pat. No. 5,901,229 (May 4, 1999, Electronic cash implementing method using a trustee); U.S. Pat. No. 5,920,629 (Jul. 6, 1999, Electronic-monetary system); U.S. Pat. No. 5,926,548 (Jul. 20, 1999, Method and apparatus for implementing hierarchical electronic cash); U.S. Pat. No. 5,943,424 (Aug. 24, 1999, System, method and article of manufacture for processing a plurality of transactions from a single initiation point on a multichannel, extensible, flexible architecture); U.S. Pat. No. 5,949,045 (Sep. 7, 1999, Micro-dynamic simulation of electronic cash transactions); U.S. Pat. No. 5,952,638 (Sep. 14, 1999, Space efficient method of electronic payments); U.S. Pat. No. 5,963,648 (Oct. 5, 1999, Electronic-monetary system); U.S. Pat. No. 5,978,840 (System, method and article of manufacture for a payment gateway system architecture for processing encrypted payment transactions utilizing a multichannel, extensible, flexible architecture); U.S. Pat. No. 5,983,208 (Nov. 9, 1999, System, method and article of manufacture for handling transaction results in a gateway payment architecture utilizing a multichannel, extensible, flexible architecture); U.S. Pat. No. 5,987,140 (Nov. 16, 1999, System, method and article of manufacture for secure network electronic payment and credit collection); U.S. Pat. No. 6,002,767 (Dec. 14, 1999, System, method and article of manufacture for a modular gateway server architecture); U.S. Pat. No. 6,003,765 (Dec. 21, 1999, Electronic cash implementing method with a surveillance institution, and user apparatus and surveillance institution apparatus for implementing the same); U.S. Pat. No. 6,021,399 (Feb. 1, 2000, Space efficient method of verifying electronic payments); U.S. Pat. No. 6,026,379 (Feb. 15, 2000, System, method and article of manufacture for managing transactions in a high availability system); U.S. Pat. No. 6,029,150 (Feb. 22, 2000, Payment and transactions in electronic commerce system); U.S. Pat. No. 6,029,151 (Feb. 22, 2000, Method and system for performing electronic money transactions); U.S. Pat. No. 6,047,067 (Apr. 4, 2000, Electronic-monetary system); U.S. Pat. No. 6,047,887 (Apr. 11, 2000, System and method for connecting money modules); U.S. Pat. No. 6,055,508 (Apr. 25, 2000, Method for secure accounting and auditing on a communications network); U.S. Pat. No. 6,065,675 (May 23, 2000, Processing system and method for a heterogeneous electronic cash environment); U.S. Pat. No. 6,072,870 (Jun. 6, 2000, System, method and article of manufacture for a gateway payment architecture utilizing a multichannel, extensible, flexible architecture), each of which is expressly incorporated herein by reference.

SUMMARY OF THE INVENTION

The present invention provides a trustee model for the collection, maintenance and distribution of entrusted information content, such as medical records or copyright works. Medical institutions and individuals are responsible for creating and storing medical records for patients treated. These medical institutions are the custodians of the records, over which the patient, or the successors of the patient hold rights. One of the patient's rights is the right to control release of the records.

The present invention therefore seeks to provide a comprehensive set of technologies to address the full scope of issues presented in implementing a secure and versatile medical information infrastructure that respects the rights of patients to privileges, such as confidentiality, gives due regard to federal and state regulations, while facilitating full and appropriate use and transmission of the data.

One aspect of the present invention therefore provides that each record is maintained within a virtual trust. In the case where they hold medical records, they are called "medical information trusts with respect to the information contained for each medical encounter, a patient's entire medical record or an entire medical record database. Similarly the concept of virtual trusts may be applied anywhere information is privileged. For example, legal information trusts would apply to the attorney client relationship, a banking information trust to the bank-depositor relationship, a government information trust to the government-citizen relationship (e.g. information on Form 1040's).

In the commercial area, examples include: entertainment information trusts could be utilized by recording artists and companies and the movie and television industries and artists to restrict access to their intellectual property and thereby prevent piracy and ensure their royalty revenue stream; subscription information trusts could be utilized by publishers of electronic magazines and newspapers; book information trusts could be utilized by electronic book publishers; retail information trusts could be utilized by retailers wishing to assure that they do not sell personal information, addresses and phone numbers of their customer; financial information trusts by securities firms and investment companies to hold investor account information; educational information trusts for tracking student test results and grades. Trusts could also be established for personal information (such as user preferences and profiles), publication and subscription information, retail and demographic information, educational information, and consumer information.

Consumer information trusts could also be utilized to prevent the unauthorized distribution of personal information including Social Security numbers, credit card numbers and other personal information transmitted electronically.

Thus, the system according to the present invention provides a conduit for the authorized transmission of medical records, while maintaining the security of the records against unauthorized access. A preferred communications network is the Internet, a global interconnected set of public access networks, employing standardized protocols. Thus, the records may be transmitted virtually anywhere on earth using a single infrastructure. Alternately, private networks or virtual private networks may be employed. In fact, as the system according to the present invention gains ubiquity, a private network model would be preferred, in order to increase security and allow the system to be tuned to the types of data and quality of service demands made by users.

Where the data is transmitted outside of an institution, it is preferably encrypted. While there are many types of encryption, a preferred model is the public key infrastructure, which may be employed in various aspects of the invention. The communication stream between the server and client is preferably a secure connection, for example using 128-bit (or higher) encryption secure socket layer transport. This ensures that an eavesdropper on the communications stream of packets cannot easily decipher the content.

The recipient is preferably authenticated using a public key-private key system, wherein the information can only be decrypted by a person in possession of the private key of the recipient. The encryption is provided at the time of transmission by applying the intended recipient's public key, which is available from a certification registrar, and is unique for that recipient.

In order to ensure authorization for the intended recipient, a key representative of the patient identity is employed. According to one aspect, this is provided as a server password, as a part of the login and authorization process. However, according to a preferred embodiment, the information relating to a patient is encrypted with a public key for that patient at a point of origin, and stored in encrypted format within a database. In order for the intended recipient to decrypt the record, he must have the patient's private key.

Further, a preferred embodiment of the invention provides an additional level of security, with a record level block or encryption provided by the server. This encryption provides increased security generally, and further preferably is integrated with an audit and/or accounting system. It is noted that both financial accounting and auditing are considered hereunder forms of accounting.

The information included in such trusts may include any valuable or private information, over which an information owner or custodian might wish to exert control, but which has a certain value when selectively disclosed in a controlled fashion.

In particular, the present invention has particular application to the management of rights in digital works, to allow a content owner to exploit the value of the works while assuring control over the use and dissemination. Likewise, the present invention has particular application to the management of personal information, such as preferences, profiles, and medical information, which may have negative impact if disclosed and used in an uncontrolled fashion.

The present invention also provides a system and method for preventing piracy or misuse of information, while ensuring a revenue stream associated with the information.

Content owners seek to distribute their content, for a fee, and seek to be the sole source of their copyright content. On the other hand, primary distribution of content through electronic means facilitates unauthorized secondary redistribution of content. The present invention therefore provides a method and system for restricting or controlling secondary redistribution of content, without imposing an undue privacy burden on consumers. The present invention also provides a secure environment for controlling content distribution while facilitating various accounting events.

Consumers could also maintain a repository of private information in trust, to prevent, for example, the unauthorized distribution of personal information including Social Security numbers, credit card numbers, user history, preferences, habits, demographics, and other personal information transmitted electronically. These trusts may thus maintain user preference, profile and history files, allowing restricted, rule -based use and access by commercial entities, while preserving the privileges, rights and value to the consumer. The rights of the consumer may indeed be negotiated or otherwise adapted to the circumstances. In this case, the trustee owes a duty to the consumer.

The present invention therefore involves the implementation and use of a virtual trust, wherein a content owner entrusts information content, generally in digital form, to a virtual trustee, which implements a set of access rules and controls on behalf of the content owner, for distribution of the content. The virtual trustee, in turn, may shield the true identity of the customer or consumer.

According to one embodiment, the customer or consumer provides necessary transactional information, which is then processed by the virtual trustee, and then "anonymized", with personally identifying information expunged.

In other instances, the trustee may be required to maintain personally identifying information, for example where personalized watermarks are embedded in the content in order to track usage and/or misuse. In that case, the trustee may, by the terms of an agreement, prevent external use of the personally identifying information. Thus, anonymization is not a necessary part of the invention, but is supported by various embodiments thereof.

Digital signatures may be employed in monetary transactions that, after authentication, are anonymous. Thus, a digital signature may be stored in an ancillary database that is private, and only accessed in the event of a post-transaction dispute. In this case, the digital signature requires either the private key of the holder for authentication, or reference to a certification authority. Thus, user-identifying information may be stripped from a transaction record, while preserving the possibility of reconstructing the identity of the party. However, without the party's consent, such reconstruction would require, for example, a court order to gain access to the certification authority records.

A particular advantage of the use of the trustee according to some embodiments of the invention is that it permits user to gain the advantages of personalized services, without relinquishing privacy. Thus, the trustee may act as a barrier, intermediary, or proxy between the user (customer or consumer) and the content owner. Further, the trustee may, in fact, serve a broad range of content owners, and thus may provide both the content owners and users a higher quality system, greater selection, and acquire personalized and statistical data based on a broader database of user patterns.

It is noted that the trustee generally acts on behalf of the content owner, not the user. However, a stated privacy policy, and possibly a negotiated agreement between the user and trustee, serves to protect the privacy of the user. Further, the user may enter into a separate trust agreement with respect to private user information. In some cases, the trustee will be the same or a related entity, but this is not required.

The trustee may thus support personalization services, based on a well populated user profile database. This personalization provides an additional business model for the trustee. It is noted that if the personal information is held by the virtual trust on behalf of the user, then the personalization may then be controlled by the user with user-provided rules. On the other hand, if the user information is retained by the trust on behalf of the content owner, then, dependent on governing laws and rules, the content owner may exploit the user information or have it exploited for its benefit.

The economic model for the trustee allows compensation from a number of sources. First, when the content owner presents the content to the trustee for inclusion in the virtual trust, which may be for that content owner alone or an aggregate of multiple content owners, an accounting may occur. Likewise, a periodic accounting may take place for included content. Accounting may also take place for browsing of the trust contents (catalog) and for transactions with users. Further, residual uses of previously transacted content may be accounted.

The user profile and personalization may also result in accounting, both with user and content owner. Further, third party advertisers and merchants may also use and account for use of the user profile and personalization, although generally only mediated through the trustee.

Other known triggers for accounting events may also be employed. Thus, the system according to the present invention does not exclude application to existing systems (such as those referenced herein) as a supplement or substitute for components thereof.

It is noted that if a financial accounting results in no net accounting, an internal or local accounting may take place without requiring an external transmission of data. Therefore, if a content string is transmitted including both content and advertising, and the receipt is authenticated, and a net non-zero accounting would necessarily be reported, then the absence of a reporting may be presumed to be the result of the content accounting and advertiser accounting offsetting each other. Thus, the transmission from the user is preempted. This technique may be further employed to assist in preserving user privacy.

Use of the personalization and user profile data typically result in compensation from the user to the maintainer. The maintainer may, in turn, compensate the user and/or the content owner whose content resulted in acquisition of the data. Likewise, commercial subsidies may also provide additional accounting transactions.

The present invention therefore seeks to provide a comprehensive set of technologies to address the full scope of issues presented in implementing a secure and versatile information content infrastructure that respects the rights of content owners and users to privileges, such as confidentiality, and gives due regard to federal and state regulations, while facilitating full and appropriate use and transmission of the data. Thus, the rules implementing the virtual trust may be jurisdiction dependent, and the application thereof vary depending on the situs of the transaction or material aspects thereof.

It is possible, for example, for multiple trusts to be involved in a transaction. Thus, during a transaction with a media information trust, consumer information may be generated. This consumer information may, by law or agreement, belong to the consumer. The consumer may then entrust this information in a virtual trust, according to a set of access and usage restrictions. While the trustee may in fact be the same entity, the trusts are separate "entities".

Thus, the system according to the present invention provides a conduit for the authorized transmission of information, while maintaining the security of the information against unauthorized use and access.

Where the information is transmitted over a public network, it is preferably encrypted. While there are many types of encryption, a preferred model is the public key infrastructure, which may be employed in various aspects of the present invention. The communication stream between the server and client is preferably a secure connection, for example using 128-bit (or higher) encryption secure socket layer transport. This ensures that an eavesdropper on the communications stream of packets cannot easily decipher the content.

The recipient is preferably authenticated using a public key-private key system, wherein the information can only be decrypted by a person in possession of the private key of the recipient. The encryption is provided at the time of transmission by applying the intended recipient's public key, which is available from a certification registrar, and is unique for that recipient. This also poses an issue for a user seeking to circumvent distribution rules, in that in order to share the file with third parties, the user must reveal its private key. Since this private key may have strategic private value to the user, release of this key publicly will be deterred. Further, decryption systems may employ a deactivation mode, wherein content or broadcasts are encoded with a series of user identifications which have been deauthorized. Such deauthorization may occur due to breach of rules, expiration of license, of other cause. Thus, if publication of a user's key becomes known to the trustee or content owner, then it may be deactivated, making the copies less desirable than properly authorized originals.

Further, a preferred embodiment of the invention provides an additional level of security, with a record level block or encryption provided by the server. This encryption provides increased security generally, and further preferably is integrated with an audit and/or accounting system. It is noted that both financial accounting and auditing are considered hereunder forms of accounting. Thus, components of the content may be separately encoded. For example, songs on a record album, segments of video (program, commercials, trailers, etc.), articles and advertisements in a journal, may all be encoded within a content transmission. Separate accounting, both positive and negative, may be applied for use or viewing of the content. Rules may be applied to the content, for example with subsidy content such as commercials or advertisements, particularly controlling a manner of presentation. In this way, a user may account for content used, while receiving subsidy for advertisements viewed. The rules may also include aggregate pricing for plural elements of the content.

If an audit trail is maintained by the trustee, this information is preferably maintained in a secure database. The audit trail may, for example, record access, use, accounting and other types of events. In an on-line system, a content-browser or player may communicate with the trustee to provide audit trail information.

Thus, in the case of voluminous records, such as a musical album, the individual songs or elements are advantageously formed as information "polymers", each "monomer" element having its own access rules. Therefore, the index may include multiple independently-accessible record elements for a contiguous set of records. Likewise, disparate and discontiguous records may be connected through the index, even if derived from different institutions or caregivers.

In one type of system, consumer media information, such as a musical album, the individual songs or elements (the monomers) are advantageously formed as information polymers (the album). In the case of a record album, therefore, the consumer may "purchase" all or some of the songs, paying only for the content used, and being subject to usage rules, such as incentives for paying for the entire album rather than just a few songs.

On the other hand, related content elements need not be included within a single record, file or transmission. Thus, an external or intrinsic index may define a compilation or set of elements. In a media information polymer, the access restrictions and rules may be defined at, and with respect to, an atomic level, although aggregate rules are preferably also provided.

In the case of a record album, therefore, the consumer may "purchase" all or some of the songs, paying only for the content used, and being subject to usage rules, such as incentives for paying for the entire album rather than just a few songs.

Preferably, the accounting for use occurs through the trustee, who in turn accounts to the content owner. However, accounting transactions may be direct with the content owner or other interested party. Further, accounting or logging of transactions may be automatic or manually initiated. Certain accounting transactions may be logged locally to the user, and transmitted in bulk to the trustee or content owner, periodically or upon a specified event.

In one embodiment, employing high security, a record is stored in a media content database, encrypted with an algorithm that requires a specific challenge-response verification in order to decrypt, either in the database or upon transmission therefrom. Upon transmission, the record is further encrypted using a transactional (e.g., single session key) encryption algorithm, and further encrypted with the intended recipient's public key. The triple-encrypted message is then transmitted over a secure connection, e.g., SSL, or a Virtual Private Network (VPN). In order to employ the record, the recipient first applies his private key, which may be stored in a physical token, such as a smart card, fob, or key. Decryption of the transactional encryption may be an automated on-line process, and is intended primarily to deter eavesdroppers and to verify receipt, authorization, and to trigger an accounting event. This activity is logged in an audit database (which is, itself, preferably secure), and the activities accounted in an accounting database. An applet "wrapper" (encryption algorithm embedded in an applet) associated with the content, is then activated, to provide access to the content, again verifying authenticity, and to assure that appropriate rules have been followed for control and management of access. In one embodiment, each use of the encrypted content requires a separate on-line transaction accounting and/or authorization session, or the results of a prior on-line session, allowing asynchronous or periodic authorization.

This scheme affords a number of advantages. First, the records in the database may be stored in encrypted format, and thus the trustee need not have access to the information contained in the records. Further, the physical security required to achieve a desired level of composite security for the database is reduced. Likewise, testing and maintenance of the database poses a substantially reduced security risk, since the records are encrypted. This also facilitates a peer-to-peer content distribution model. Thus, content records may be widely dispersed, and sharing encouraged, since each new user engages in an accounting and/or authentication transaction, facilitating content management. Since distribution is low cost and not capital intensive, consumer costs may also be lowered. Further, since the system supports a variety of compensation schemes, more equitable distribution of burden and income may be achieved. Through implementation of a micropayment system, as is known in the art, transaction expenses may be controlled, and in some implementations, consumer privacy protected.

Each use of the record triggers an accounting/audit event, thus allowing finely granular records of record access, and reduces the risks of security and privacy breach after record transmission. Importantly, this allows usage based financial accounting for the records, imposing a financial burden based according to value. Therefore, the revenues for maintenance of the system may be based on a number of factors, automatically calculated, which impose low costs for minimal usage of the records and larger costs on substantial use of the records. Typically, the financial burden will be about the incremental cost of servicing a request, plus a portion of the profit, amortization, and overhead for constructing and maintaining the system. It is this profit, overhead and amortization component that may be shifted more heavily to extensively used records from those with lesser value. On the other hand, the net cost to a consumer for popular content may be less than that for obscure content.

In the case of information content which is private, such as business or personal records, the system architecture differs, in that disclosure of the content must be protected. In a normal consumer media system, the content is not confidential, and thus the distribution system is intended to impose a barrier to circumvention, rather than generally protect with high security the content. A secure system must, however, be designed to meet emergency requests. This ability to provide high security in general, but also provide exception processing with lower security, will undoubtedly increase system costs for even non-emergency requests. Thus, an additional fee component may be applied to emergency information or content requests. The urgency of a request may be determined, for example, by a self-reporting, or a contextual assessment thereof.

According to some embodiments, when a recipient seeks a record, he must identify himself, and the identity of the desired content record. The identification of the recipient is then authenticated, for example using a digital signature or challenge-response authentication scheme, in which messages are passed back and forth between the recipient and server.

In the case of private content which is "triple encrypted" as discussed above, when a requester receives a file, he must enter his own decryption key as well as the content decryption key. The content decryption key is obtained extrinsically, or from a certification authority that verifies the circumstances of access and the requirements therefore. The certification authority is preferably separate from the trustee. However, the decryption need not be direct, i.e., the keys used in a locally executing algorithm to release the record contents. Rather, an on-line process is preferably implemented, in which the authentication (decryption) codes are entered, and accounting and audit information processed, in order to release the file contents. Thus, the present system potentially provides a third level of encryption, to support its own access restrictions, which, for example, may be driven by a need to account for access. This encryption may be applied, for example, as the record is being prepared for transmission from the database. The on-line process also serves to protect record privacy, since an audit entry may be maintained for each usage, rather than only for the transmission usage.

In the case of confidential records, the recipient's "role" may be checked for consistency with a set of role-based access rules, defined by the content owner, but may change in different contexts. The reported role may be accepted, or verified with a database. Based on the role of the recipient and the identification of the content, an index for the database is searched for records. Preferably, the index includes, for each content record associated entry, an identification of the location of the content record and a set of access rules, which are, for example, role based.

The role-based access rules are generally defined automatically based on contextual and circumstantial data. Manual rules and edits may also be supported. Typically, a hierarchy is defined of data sensitivity, with the most sensitive data provided with the highest level of restrictions.

The access rules are defined by a set of defaults, and "overrides", implementing a content owner's wishes. The defaults, in turn, are defined as a standard overall system security level.

Since, according to one embodiment, the trustee does not have decrypted access to the content records, the content owner must build the index. Often, the rules will be applied based on a generic type of record, with sensitive records, afforded the highest protection, and more public information provided with less security.

The recipient, after authentication of identity and role, is then presented with a list of content records available and/or existing. For sensitive records, even the existence may be shielded, while for less sensitive records, the content is shielded while the existence is not. The recipient then selects which records to receive, in an interactive process over the secure communications channel. The records are then "wrapped" with the controlled access applet, and encrypted with the recipient's public key and transmitted over the secure communications channel.

In some instances, a recipient will have access to or be provided with a summary, synopsis or program guide of a content record. For example, summaries may be a part of the record generated by the private content owner. This summary may be available to the recipient based on the access rules, and therefore delivered to the recipient in the stated manner. Subsequently, the recipient may, based on the contents of the summary, request further records. Preferably, the present invention provides a "fast" interactive mode for delivering such summaries, making the encryption and authentication process as transparent as possible for the series of transactions.

The present invention also provides a privileged information trust, for example a media content information trust, a secure and verifiable access database, and systems and methods therefore.

According to an aspect of the present invention, it is not necessary to consolidate the media content into a single file. Thus, many separate media portions may be stored separately, and indeed in separate portions of a distributed database. A central index is maintained which records, for each piece of identified content, the location of the portions and access rules therefor. For retrieval, only those content records that are contextually relevant are recalled. Of course, these may be consolidated.

In order to maintain privacy of the media content record, the content itself may be encrypted. In this case, the access rules are externally coded, so that the content of the record may be shielded while still permitting controlled access. Various security schemes may be employed for selective access to the record once delivered. For example, each access requester may be provided with a public key/private key pair. The record may be delivered encrypted with the public key, in a form such that the private key is necessary in order to decrypt the information, while also authenticating the content. Thus, in the case of personal data in trust, employed by an advertiser or content seller, the personal data is delivered in encrypted form, and the user must authenticate himself and account for the use. Different users or types of users (e.g., roles) may have different rights of access, defined by rule.

In cases where the database holds encrypted records, physical security of the database provides an additional layer of protection. Thus, for example, personnel maintaining the database need not be exposed to private records.

One embodiment of the present invention therefore envisions a system architecture having three separate portions: (a) the database(s), containing individual records, which may be encrypted or plain-text; (b) an index, relating content identifier with database records, as well as access rules; and (c) optionally, a certification authority, holding encryption data. The certification authority serves a practical purpose, but implementation of such an authority may be avoided if respective passwords and encryption keys are reliably and securely held only by authorized users. However, since emergency situations arise in practice, which may require decryption key access without personal express authorization from the content owner, the certification authority may be an important component of the system. The certification authority also issues the keys, enforcing certain rules for key selection.

The certification authority employed in conjunction with the present invention presents the same issues as typical existing certification authorities. These entities presently hold encryption keys, which are released only under specified conditions. Typically, the release of secure keys involves an authentication step and incurs risk of detection of unauthorized recipients. According to the present invention, there may be a need for automated release of such encryption codes, for example where the volume of requests exceeds a manual processing capability. In this case, a highly secure personal authentication scheme may be implemented, for example using biometric authentication, or a combination of password and key access. Of course, this is generally not possible with public systems, where strict user-level control cannot be presumed. It is also possible to implement role-based or authority-based access in addition to other schemes, for example, in the case of medical information, limiting access to physicians and institutional administrators.

According to the present invention, the records may be treated as copyright works. Therefore, a license fee may be charged for any copying or use of the record, based on a copyright license. The provider, in turn, may then receive a passthrough royalty payment. Even if a copyright theory is ultimately found defective, the database may still be protected under other types of legal regimes, for example the Digital Millenium Copyright Act (DMCA), with respect to its copy protection/anticircumvention features, or sui generis protection available in certain countries. In fact, many of the proposed techniques for protection, distribution and accounting proposed for use with consumer media information, such as digital music files, e.g., MP3 files, may advantageously be applied in accordance with the present invention.

It is noted that, in the case of public media content, the content itself need not be encrypted. Instead, a secure watermark and digital rights management-implementing playback system may be used. Thus, while the content is not encrypted, usage restrictions and content tracking and management functions may be implemented through encrypted or hidden messages in the content. This technique permits the content to be employed without decryption (which may consume valuable computational resources), while permitting content management on behalf of the content owner.

In order to provide further security for the records and the use of the system, various techniques are available. For example, dummy content records may be added to the database and index. Any access of these records is presumably based on an attempt for unauthorized access. Thus, the existence of these records, with access tracking, allows detection of unauthorized uses of the system. Another method of securing the system is the use of steganographic techniques, for example embedding watermarks in audio and images, pseudorandom dot patterns in scanned page images, random insertion of spaces between words, formatting information, or the like, in text records, or other techniques. Therefore, records obtained through the system may be identified by their characteristic markings. In fact, every authorized transmission may be subjected to a different set of markings, allowing a record to be tracked from original authorized access to ultimate disposition. An explicit bar code, watermark or other type of code may also be provided on the document for this purpose. It is noted that such markings cannot be implemented at the point of transmission on encrypted data, and thus this type of security requires access to the raw content. However, this may be implemented at the point of decryption, which may be in a sufficiently secure environment. Thus, the present invention provides a system for the decryption and watermarking of data, in a content (or content type)-specific manner. An online handshaking event may occur on decryption, to provide confirmation of the process, and indeed may also authenticate the user of the system during decryption.

One particular application of the present invention is directed toward the management of access to medical records. Thus, the system according to the present invention provides a conduit for the authorized transmission of medical records, while maintaining the security of the records against unauthorized access. A preferred communications network is the Internet, a global interconnected set of public access networks, employing standardized protocols. Thus, the records may be transmitted virtually anywhere on earth using a single infrastructure. Alternately, private networks or virtual private networks may be employed. In fact, as the system according to the present invention gains ubiquity, a private network model would be preferred, in order to increase security and allow the system to be tuned to the types of data and quality of service demands made by users.

In order to ensure authorization for the intended recipient, a key representative of the patient identity is employed. According to one aspect of the invention, this is provided as a server password, as a part of the login and authorization process. However, according to a preferred embodiment, the information relating to a patient is encrypted with a public key for that patient at a point of origin, and stored in encrypted format within a database. In order for the intended recipient to decrypt the record, he must have the patient's private key.

In a medical information polymer, disparate and discontiguous records may be connected through the index, even if derived from different institutions or caregivers. Since the access restrictions are defined at an atomic level of the medical information polymer, these may be applied both at the trustee server system, to limit access based on predefined rules, or at the recipient level, to limit access to desired records which are available based on the recipient authorization.

For example, a record is stored in a medical records database encrypted with a respective patient's public key. Upon transmission, the record is further encrypted with a transactional encryption algorithm, and further encrypted with the intended recipient's public key. The triple-encrypted message is then securely transmitted, and decoded in reverse hierarchical order. This decoding may include requiring the recipient to engage in an on-line authentication/accounting transaction, to decrypt the transactional-level encoding. This activity is logged in an audit database, and the activities accounted in an accounting database. An applet "wrapper" may be associated with the record, which, in conjunction with the supplied patient's private key, allows decryption of the record itself. Each use of the encrypted record requires a separate on-line transaction accounting session.

Since the system must be designed to meet emergency requests, which will undoubtedly increase system costs for even non-emergency requests, an emergency transactional fee may be added to a normal transaction fee in such circumstances. The urgency of a request may be determined, for example, by a self-reporting, or a context. In fact, since the system houses medical records, the urgency may be determined after the fact, with delayed accounting for this fee component.

When a recipient seeks a record, he must identify himself, his role in the patient care, and the identity of the patient and/or record. The identification of the recipient is then authenticated, for example using a digital signature or challenge-response authentication scheme, in which messages are passed back and forth between the recipient and server. See, for example, U.S. Pat. No. 6,028,937 (Tatebayashi et al.), U.S. Pat. No. 6,026,167 (Aziz), U.S. Pat. No. 6,009,171 (Ciacelli et al.) (Content Scrambling System, or "CSS"), U.S. Pat. No. 5,991,399 (Graunke et al.), U.S. Pat. No. 5,948,136 (Smyers) (IEEE 1394-1995), and U.S. Pat. No. 5,915,018 (Aucsmith), expressly incorporated herein by reference, and Jim Wright and Jeff Robillard (Philsar Semiconductor), "Adding Security to Portable Designs", Portable Design, March 2000, pp. 16-20.

It is also possible to employ so-called rolling code encryption, in which a pseudorandom number generator is employed to generate a sequence of codes, wherein a common seed for the pseudorandom number generator used for encryption and decryption maintains synchronization. In such a system, each code sequentially generated by the system differs, thereby allowing distinct encryption codes (keys) to be generated and employed. The security of the system relies, in part, on the presumed difficulty in determining the pseudorandom seed by analyzing a sequence of generated codes. See, U.S. Pat. No. 5,369,706 (Latka, Nov. 29, 1994); and U.S. Pat. No. 5,420,925 (Michaels, May 30, 1995), expressly incorporated herein by reference.

The recipient's role is checked for consistency with the recipient's identity, but may change in different contexts. For example, a physician may be an attending/primary care physician or a consultant on a case. The reported role may be accepted, or verified with a recipient medical institution database. Based on the role of the recipient and the identification of the patient, an index for the database is searched for records. Preferably, the index includes, for each patient associated entry, an identification of the location of the medical record and a set of access rules, which are, for example, role based.

Thus, for example, an attending physician would likely have access to complete medical records, while a therapist would have limited access to relevant records.

The access rules are defined by a set of defaults, and "overrides", implementing a patient's wishes. The defaults, in turn, are defined as a standard overall system security level, additionally, the custodian medical institution that is the source of the records may impose their own access rules.

Since, in a preferred embodiment, the trustee does not have decrypted access to the medical records, the index is created by another party. For example, the custodian institution or a medical information clearinghouse may build an index. Often, the rules will be applied based on a generic type of record, with sensitive records, such as sexual, drug abuse and psychiatric history afforded the highest protection, and more public information, such as date of birth and hair color provided with less security.

The recipient, after authentication of identity and role, is then presented with a list of medical records available and/or existing. For sensitive records, even the existence may be shielded, while for less sensitive records, the content is shielded while the existence is not. The recipient then selects which records to receive, in an interactive process over the secure communications channel. The records are then "wrapped" with the controlled access applet, and encrypted with the recipient's public key and transmitted over the secure communications channel.

In some instances, a recipient will have access to or be provided with a summary or synopsis of a record. For example, summaries may be a part of the record generated by the custodian medical institution. This summary may be available to the recipient based on the access rules, and therefore delivered to the recipient in the stated manner. Subsequently, the recipient may, based on the contents of the summary, request further records. Preferably, the present invention provides a "fast" interactive mode for delivering such summaries, making the encryption and authentication process as transparent as possible for the series of transactions.

While it is preferred that the medical records be maintained in trust by the trustee, in some instances, the custodian will maintain the records and mediate requests for access. The present system, in that case, serves as a front end for interfacing with the custodian's private network, as well as performing the authentication and optionally rule-based access implementation. In this case, the index serves to identify the relevant institutional databases, and may serve as a proxy to consolidate the search for records through a single access system. Typically, where the records are external, the access rules will also be external.

The trustee system according to the present invention may be provided with access rights to interface with institutional private networks through a firewall or VPN. An applet may be provided by the trustee to the institutional network server, to implement the access rules within the firewall, thus maintaining security of the records, even from the trustee. Alternately, the custodian medical institutional system may implement native access rules. In either case, the record transmitted by the institutional system to the trustee system may be encrypted with the patient's public key, and thus the process is sufficiently similar that the difference between access through the trustee database and the custodian (institutional) database may be transparent.

In like manner, in appropriate instances, a recipient may make a query to search the medical record. In that case, the query must be performed on a decrypted record, e.g., locally by the recipient, or within the custodian private network. Of course, if the trustee system supports decrypted medical records, then a search may be conducted therein. In the later case, the query is transmitted from the recipient to the trustee, to the custodian medical record system. The query produces a result, typically based on the entire record, since the access rules are typically not applied within the custodian network. The results must then be filtered based on the defined rules. As above, the search result may indicate records that are accessible or inaccessible by the recipient, or shield the existence of unauthorized records. These results may then be transmitted to the recipient in the manner of the medical summary discussed above.

The present invention also provides a privileged information trust, for example a medical information trust, a secure and verifiable access database, and systems and methods therefore.

The present invention provides, according to one embodiment, an extensible database architecture that provides data records relating to patient transactions. Accordingly, the transaction data need not be physically linked within the computer storage medium, and indeed, for various reasons, transaction data relating to a specific patient may be intentionally split. Rather, each transaction is indexed by patient identifier, which has historically been a social security number. While this number was not originally intended for this purpose, medical institutions and third party payors have universally used these identifiers in the past, and therefore legacy data almost universally includes social security numbers. Thus, even if a trend were established to eliminate its use, social security number identifiers would remain within the database. A surrogate identifier may be employed, for example to deal with redundant Social Security Numbers (SSNs), persons without an SSN, or those who refuse to allow use of an SSN.

Each transaction within the database may be a small record, for example a result of a simple blood test, or a large record, such as radiological data. A transaction may also include aggregations of data, such as records from an entire hospital admission. Each transaction is preferably associated with a descriptive header, providing metadata regarding the record content, as well as rules for access. The access rules may be stored outside the record itself, and thus provide only a very general level of information outside the record itself, while ensuring that only those aspects of the record are retrieved which are necessary for the context of use.

According to an aspect of the present invention, the medical record need not be consolidated into a single file. Thus, many separate transactions may be stored separately, and indeed in separate portions of a distributed database. A central index is maintained which records, for each patient, the location of the transactions and access rules therefor. For retrieval, only those records that are contextually relevant are recalled. Of course, these may be consolidated.

In order to further maintain privacy, the record content itself may be encrypted. Thus, since the access rules are externally coded, the content of the record may be shielded. Various security schemes may be employed for selective access to the record once delivered. For example, each medical professional may be provided with a public key/private key pair. The record may be delivered encrypted with the public key, in a form such that the private key is necessary in order to decrypt the information, while also authenticating the content.

The preparation of this record may be performed in a trusted environment, separate from the database retrieval system itself. Thus, in the main database, patient records may be stored using a public key-private key design (PKI—"public key infrastructure") encrypted with the patient's private key by the original source of the information. Upon retrieval, patient authorization is verified by obtaining the patient's public key.

Thus, the message may be multiply encrypted, using, for example, both patient and provider keys, or a combination thereof, requiring a proper identification of both the provider and the patient.

The patient keys may be assigned periodically, for example for a hospital stay, or uniquely or each patient.

In general, aspects of this security scheme are weak with respect to "insiders", since key security is likely to be poor.

For example, a physical token may be borrowed or stolen. While biometric authentication may reduce these risks, they are not eliminated entirely. For example, in many instances, requests for records are made by clerical or administrative personnel on behalf of a medical practitioner. Thus, the intended recipient is different than the requester. It is not always practical to require a set of on-line transactions for use of the medical record, and thus security may be breached by allowing a transmissible decrypted information object to exist. However, to the general public, this type of security is strong. In order to provide internal security, access logs and audit trails are maintained. These logs and trails are effective deterrents to record misuse, even though they typically do not detect misuse in real time. Medical professionals' license and reputation are tied to appropriate and ethical use of the information, and therefore potential for discovery of a breach by retrospective review of the logs and trails would serve as a deterrent. Further, challenge-response security methods may be employed, and/or rolling code methods, in order to further verify the recipient.

In the event that a patient's private key is discovered or released, the security of the database for that patient may be compromised. On the other hand, during record access, the encryption may be efficiently changed. Thus, the keys may be changed after each access, providing a rolling code-type security scheme, i.e., one in which the code changes during use, in a manner which is outwardly unpredictable, but in a manner known to both counterparties to the communication. The issues here are that (a) the security breach may be undiscovered and (b) the archive database contents are difficult to alter. These may be addressed by periodically changing the encryption during regular database maintenance. The record decryption and re-encryption may be handled by a trusted certification authority, which possesses the encryption key pairs in any case. The PKI registrar must also maintain a secure database, since the encryption keys must be stored in case of emergency.

Therefore, the database of medical records may be maintained in an encrypted state, vastly reducing the security risks in maintaining the database. On the other hand, the index, which is presumably much smaller and more easily maintained, requires more security. However, since the index and associated records are separate, a security breach of the index alone only yields only the patient identifier, and access rules, and possibly other indexed information, but not the record content itself. Therefore, ancillary security measures may be employed to maintain security of the database records.

A database operator may serve as a trustee for the medical records or associated access restrictions therefore (e.g., custodial possession of or control over cryptographic keys), on behalf of the patient, implementing a set of access rules defined, for example, by the patient, legal system, or medical system policies.

This medical information trust is a significant advance, since it allows the patient to exert control over the release of medical records, and potentially allows a more optimal allocation of costs for medical records creation, maintenance, use and transmission. Typically, third party payors and insurers have accepted the cost of medical record keeping as an inherent part of the cost of medical care. By providing an opportunity to segregate this cost, and indeed externalize the process from the medical institution, greater efficiencies and more optimal allocation of costs may be achieved.

Indeed, the medical institution is an intended "client" of the medical information trust, since by consolidating a plurality of institutions, uniformity, interoperability, cost reductions, and improved security result. Further, with the present changes in regulations encompassing medical records, internal compliance by medical institutions, providers and all parties accessing the medical record, with the regulations will also be required.

One system architecture according to the present invention therefore envisions three separate portions: (a) the database(s), containing individually encrypted records; (b) an index, relating patient identifier with database records, as well as access rules; and (c) a certification authority, holding encryption data. The certification authority serves a practical purpose, but implementation of such an authority may be avoided if passwords and encryption keys are reliably and securely held only by authorized users. However, since emergency situations arise in practice, which may require decryption key access without personal express authorization from the patient, the certification authority is an important component of the system. The certification authority also issues the keys, enforcing certain rules for key selection.

Since the database holds encrypted records, physical security of the database provides a supplemental or additional layer of protection. Thus, for example, personnel maintaining the database would not be exposed to patient confidential records.

On the other hand, the index contains critical information that carries low value unless abused. This abuse, in turn, could be detected by audit trails and other access controls, to both the index, and database itself.

Typically, the security of the database need only be such that it is not the weakest link in the chain; for example, medical records are available for abuse at the point of creation, after transmission to an authorized party, and at clearinghouses.

During an acute illness, the medical record for a patient will be active, and not immediately added to the archival database. Because of the massive database undertaking, in general the archival database system may be architected to include records that are both final, and relatively inactive. Thus, once a record is written to this archival database, it would not be modified, and the data access demands should be relatively small, allowing a high ratio storage capacity to bandwidth capacity database system to be employed. Alternately, the active and archive databases may be consolidated, providing a single access system for the medical information. Thus, active patient records may be stored separately. The present system therefore proposes, in one embodiment, a large archive of "inactive" medical records and a set of active records.

During an acute illness or hospitalization, medical records stored in the custodian's database may be constantly subject to update and modification by the medical institution. Therefore, the treating institution or custodian will maintain the most accurate records. The present invention therefore preferably accesses such records through the custodian's database on a private network, rather than seeking to maintain an accurate and synchronized copy of the records elsewhere. The trustee system may therefore maintain a log of access and a list of where to search for updated records. Further, external access of the active patient record from outside the custodian's private network will be rare.

Thus, the present invention proposes, in one embodiment, that active medical records be accessed directly from the treating medical institution. Rather than seeking to maintain an updated index and access rules for the active medical record, a relatively simple pointer may be maintained in the index identifying the active medical record and invoking a separate access system. In some instances, this separate access system will be completely controlled by the treating medical institution, while in others, an "Internet" (public internetworked access interface) may be implemented using a standardized protocol.

In the case of active medical records, typically the custodian's internal database is not encrypted. Thus, internal access to the records does not require a decryption key. One method for bridging the active and inactive systems is to transform the active medical record at the institutional firewall (secure interface between internal and public networks) into an archive format, compatible with the trustee's database system. Thus, in this case, access rules are computed, the rules processed, and the record encrypted according to the archive format. Therefore, a relatively transparent process may be implemented, wherein a record requestor is not aware that a record is derived from an active or archive setting. Therefore, various rules and transitional rules may be flexibly implemented for defining active and archive records.

In some instances, there may be redundancy or inconsistency between the active and archive medical records. For example, a record may be transferred to an archive, and subsequently the patient has another encounter in the same matter. In this case, the archive record will be incomplete. Likewise, through a quality control process or otherwise, a medical record may be corrected, supplemented or altered. While an audit trail will generally be maintained to verify that any changes are authorized, records are generally taken at face value without reference to the audit database. In order to provide an updated archive, a number of techniques are available. First, if the change is an addition, a new transaction record may be added to the archive, with a corresponding entry made in the index. This is the normal method for adding data to the archive. Second, the archive record may be modified. Typically, the archive will be stored on non-rewritable media, or if rewritable, space will be allocated at the time of original record creation. Preferably, a small amount of free space will be allocated and preserved with each transactional record, for example, a remaining space in a storage "block", or additional blocks for large records. This space may be used to store a patch table or an addendum itself. Finally, a record of such changes or additions may be made at the index level or in a master patient record file.

The present invention also encompasses a medical information trust or virtual information trust. Therefore, according to this aspect of the invention, rather than merely being caretaker of an encrypted archive, the system according to the present invention may hold the medical information in trust on behalf of the patient, and thus is subject to rules defined by the patient for access to the medical record, including the possibility of full access, partial access, or no access.

Therefore, an embodiment of the invention provides a trustee database that includes decrypted or plaintext records. According to this aspect of the invention, a distinct security paradigm is necessary. This may be, for example, the secure mediator paradigm of Gio Wiederhold et al., or another system that provides secure and authenticated access to the records.

In the case of medical information trusts, the possibility for data analysis of patient records is possible, for example to perform statistical analysis, academic research, and indeed to provide information and recommendations to the patient. The system according to the present invention may provide a large and diverse set of available medical record content. Thus, by obtaining a large number of records for analysis, very sensitive and specific studies may be performed to determine risk factors for disease, propose tests for possible latent conditions, or otherwise provide data for the patient.

Further, the trustee system may proactively maintain current information about the patient independent of a medical practitioner. For example, medical histories and questionnaires may be periodically updated so that the medical record is current, including medications, conditions, complaints, impairments, etc. Thus, a health care professional may access the record (on authorization) to obtain this information for efficient treatment. Further, the system may cooperate with a treating medical physician, in order to gather and maintain specific information for use by that physician, again making patient encounters more efficient.

Critically, insurance forms, authorizations, and the like, may be filled out remotely, for example using a secure socket layer (SSL) connection on the Internet or on an intranet, prior to a scheduled visit, reducing waiting time.

By supplementing the patient medical information archive with a summary medical record extract (in trust), powerful advantages accrue. For example, patient health information becomes increasingly portable, and thus the efficiency of medical services may increase. Emergency services are also facilitated.

It is noted that a summary medical record extract file may itself include role-based or context-based access restrictions, both to the entire record and to portions thereof. Context based access may, for example, allow immediate release of important information in emergency situations. Such context-based access may also be used to program medical devices and facilities based on patient parameters. The medical records may also be specified as accessible for a particular individual, group, entity, or device.

Since the summary medical record extract file is separate from the medical record itself, and presented in a strictly defined format, it is readily made anonymous. Therefore, for academic study, a set of anonymous master patient record files are enabled. Special rules may then be implemented for subsequent access to the transactional records, where necessary, to complete a study. For example, a patient may execute a consent form for inclusion in a study, with defined records access rules. In case of an absence of specific consent, it may still be possible to obtain necessary information in an anonymous fashion. Thus, an anonymous summary medical record extract includes incidents, some of which may be relevant for a study. The researcher then requests further information about the incident for the anonymous patient. The request is then translated by the index server to identify the desired transactional record. Using access rules, the authority for access of the record is verified. Typically, such access would be denied if the desired transactional record is particularly sensitive or cannot be made anonymous, for example, including a scanned page with the patient's name or identification embedded in a non-redactable form. Manual redaction may also be used, but would be more costly. An automated scrubbing program may also be implemented to remove personally identifiable information from the medical records.

The security of even anonymous summary medical record extracts is often critical, because the facts presented therein often are specific enough to identify a particular individual, thus allowing a bridge between limited patient-identifying data and an entire anonymous record.

In order to provide further security for the records and the use of the system, various techniques are available.

For example, dummy patients may be added to the database and index. Any access of these records is presumably based on (a) academic research of anonymous data, which is then filtered to eliminate the dummy data, or (b) unauthorized access. Thus, the existence of these records, with access tracking, allows detection of unauthorized user of the system by academic or medical users.

The role-based access rules are generally defined automatically based on contextual and circumstantial data. Manual rules and edits may also be supported. Typically, a hierarchy is defined of data sensitivity, with the most sensitive data provided with the highest level of restrictions. Typically, primary care providers have the highest level of access, while paraprofessionals have data on a context-dependent requirements basis only. Further, non-professionals may be provided with data on a need-to-know basis only. For example, transport personnel might need to know if a patient has violent tendencies, contagious disease, or an acute condition.

Other medical personnel have access to the record based on context and role. For example, a respiratory therapist might require access to pulmonary and central vascular history records, as well as abstracts of acute medical information, current pharmaceutical information, scheduling (e.g., for inpatient care), and specific notes directed to the therapist, individually or in a treatment group.

Thus, a past history of depression (resolved) in a patient admitted for a kidney stone may be communicated only to the primary care physician and psychiatric treating professional, if any. Possibly, this data would be communicated to a pain management professional, if the past history of depression had a pharmacological or drug abuse component. This data is otherwise deemed contextually irrelevant to the acute treatment.

The present invention seeks to provide an enhanced level of interoperability and portability of electronic medical records (EMR) between various health care professionals, researchers, and third party payors, without compromising confidentiality. Further, the system and method according to the present invention present a new business model for the creation, maintenance, transmission, and use of medical records, allowing financial burdens to be reallocated, for example more optimally or equitably, to decrease overall societal cost, or simply to provide a successful business model for a database proprietor.

In order to increase interoperability between disparate database and EMR formats, the present invention provides a common file-tagging format, for example extensible markup language (XML) to encode records. Thus, the file formats need not be fully translated, but rather data elements tagged in a standardized format. A recipient may then implement a file translation, if necessary. Alternately, the recipient may use the file in its native format, for example by printing the file in paper form, or viewing on a computer monitor. The record reader application software may impose hardcopy output and electronic copying restrictions, and, for example, impose time-out limits to prevent unusually extended viewing sessions.

In order to increase portability, the physical records, especially archives, may be stored outside a medical institutional infrastructure. Thus, limitations of access and bandwidth imposed by a public network gateway for a medical institution do not impede information transfer. Authorizations, as distinct from the medical information sought, are verified on-line, and may involve access to a medical institution, but typically command substantially lower bandwidth requirements.

According to a preferred embodiment, the EMR system is capable of receiving and transmitting information between a large number of sites simultaneously, and typically provides a distributed architecture for scalability and peak load handling capability.

It is noted that, while the present invention is capable of handling radiological data, the medical records handling systems are not necessarily optimized for storage and transmission of massive image data files. Therefore, according to another aspect of the invention, a separate subsystem is provided for such image files. Advantageously, an image file database system is configured to operate as an off-site backup for computerized radiology practices, and thus gains significant economies by performing dual functions. In many instances, courier or postal transmission of physical recording media is preferred to electronic transmission, especially where the recipient does not have high bandwidth communications capability. Thus, as an additional aspect of the invention, a capability for rapid production of individual medical transaction records or entire records stored on computer-readable recording media is provided. For example, Recordable CD ROM (CDR), DVD-RAM or DVD-RW disks may be employed.

For example, if an entire record is stored to a portable computer readable storage medium, it may include various access restrictions, encryption, password, audit trail and accounting properties, and thus may serve as an extension of an on-line system.

According to the present invention, an index is maintained which includes relatively sparse information defining the identifier of the patient, access rules, and the location of the record file. In fact, this system does not prevent direct access by an intended and authorized recipient to a database system maintained by the source medical institution. While such access cannot be guaranteed, and indeed the conditions and quality of such access will vary between medical institutions, this allows medical institutions to establish their own policies and procedures for access to medical records under their control.

Likewise, according to the present invention, a patient may, within the scope of available resources, define rules and procedures for access to medical records. Thus, the rules defined by a patient or record owner may differ from those imposed by the custodian medical institution. A default set of rules restricts access to medical professionals who can demonstrate authorization, with disclosure of particular transactional records limited according to a set of rules defined by the role of the requester. As trustee for the patient, the proprietor of the database system may also implement more or less restrictive rules as defined by the patient, and release records accordingly. The trustee may also, within the scope of law and regulation, implement a set of rules defined by the respective individual or custodian medical institution in connection with that institution's processing of its custodial medical records.

In addition, in the case of a research study, patients may be compensated for access and/or use of the records in the manner of a paid research subject.

According to the present invention, the originating (custodial) medical institution creates the original record. The original input process is typically considered integral to the provision of medical care, and is not compensated separately. Often, a clearinghouse then processes medical records, which is typically an external firm. The result may be a complete coded version of the paper record generated by the institution, or merely a set of coded entries for the various billable procedures and aspects, or somewhere in between. In this process, the paper record may be scanned and optically character recognized. The clearinghouse typically imposes a significant internal or external expense, since high quality is critical. Since this is not a direct element of patient care, it is not a reimbursable expense, and is treated as institutional overhead.

One significant purpose for coding these records (beyond tallying treatment costs for billing) after a hospital visit is due to the value of the archive information. Appropriately, these costs may be imposed on the subsequent users of the information, and indeed may serve as a revenue center for the institution or provider.

By externalizing administration of an archive database, the medical institution has reduced costs for implementing and maintaining infrastructure, and further due to the efficient distribution of records from a consolidated database, it is likely that an increased number of records will be obtained. Therefore, the trustee, as proprietor of the centralized database, may collect fees for the medical institutions. These fees, in turn, incentivize the institutions to cooperate with the trustee. Usage fees are based on authorization, authentication, index access, and database access and usage. Links provided by the index, for example directly to internal institutional databases, may also be accounted. The purpose of these numerous fees is primarily to optimally distribute costs, rather than increase costs. Thus, the system according to the present invention is permissive of an outsourcing model for the custodian medical institution. Indeed, this allows externalization of the archive, relieving the medical institution of the responsibility for (overhead includes personnel, space and equipment) maintaining a medical record archive. Assuming a license for use of the records, fees may also be charged for the right to copy the record.

It is noted that, even if a medical professional is authorized to view the entire record, he may not wish to do so. Therefore, as an intermediate process to delivering and decrypting an entire record, the user may be provided with an index of certain records, for selection thereof. Preferably, a dense index and/or summary of the records are available in electronic format as well. Delivery and use of this summary is, or course, an accountable item. The summary record is typically stored in the database as an encrypted file, subject to the various access, audit and accounting rules provided by the present invention.

When a requester receives a file, he must enter his own decryption key as well as the patient's decryption key. The patient's decryption key is obtained from the patient, or from a certification authority that verifies the circumstances of access and the requirements therefore. However, the decryption need not be direct, i.e., it is not necessary to use the keys in a locally executing algorithm, to release the record contents. Rather, an on-line process is preferably implemented, in which the authentication (decryption) codes are entered, and accounting and audit information processed, in order to release the file contents. Thus, the present system potentially provides a third level of encryption, to support its own access restrictions, which, for example, may be driven by a need to account for access. This encryption may be applied, for example, as the record is being prepared for transmission from the database.

The on-line process also serves to protect patient privacy, since an audit entry may be maintained for each usage, rather than only for the transmission usage.

Thus, a plurality of components, individually or in combination or subcombination, may be applied to support operation of the system.

A recent U.S. law, The Health Insurance Portability and Accountability Act of 1996 (HIPAA), is intended to improve the Medicare and Medicaid programs and other Federal health programs and private health programs, and the effectiveness and efficiency of the health care industry in general, by simplifying the administration of the system and enabling the efficient electronic transmission of certain health information. This Act is to be implemented by regulations promulgated under authority of the Secretary of Health and Human Services. See, e.g., 45 CFR Parts 142, 160-164 (final and proposed rules), incorporated herein by reference. The system and method according to the present invention preferably complies with and implements the statute and proposed rules, to the extent that the system is encompassed thereby.

One aspect of the efficient administration of health systems is the use of standardized health care provider identifiers, for example the national provider identifier (NPI), an 8-position alphanumeric identifier. Another aspect provides standardized format for the transmission of medical record data. The present invention may implement unique individual health care identifiers or an arbitrary unique code.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE PREFERRED EMBODIMENTS

Example 1

Figure 1:
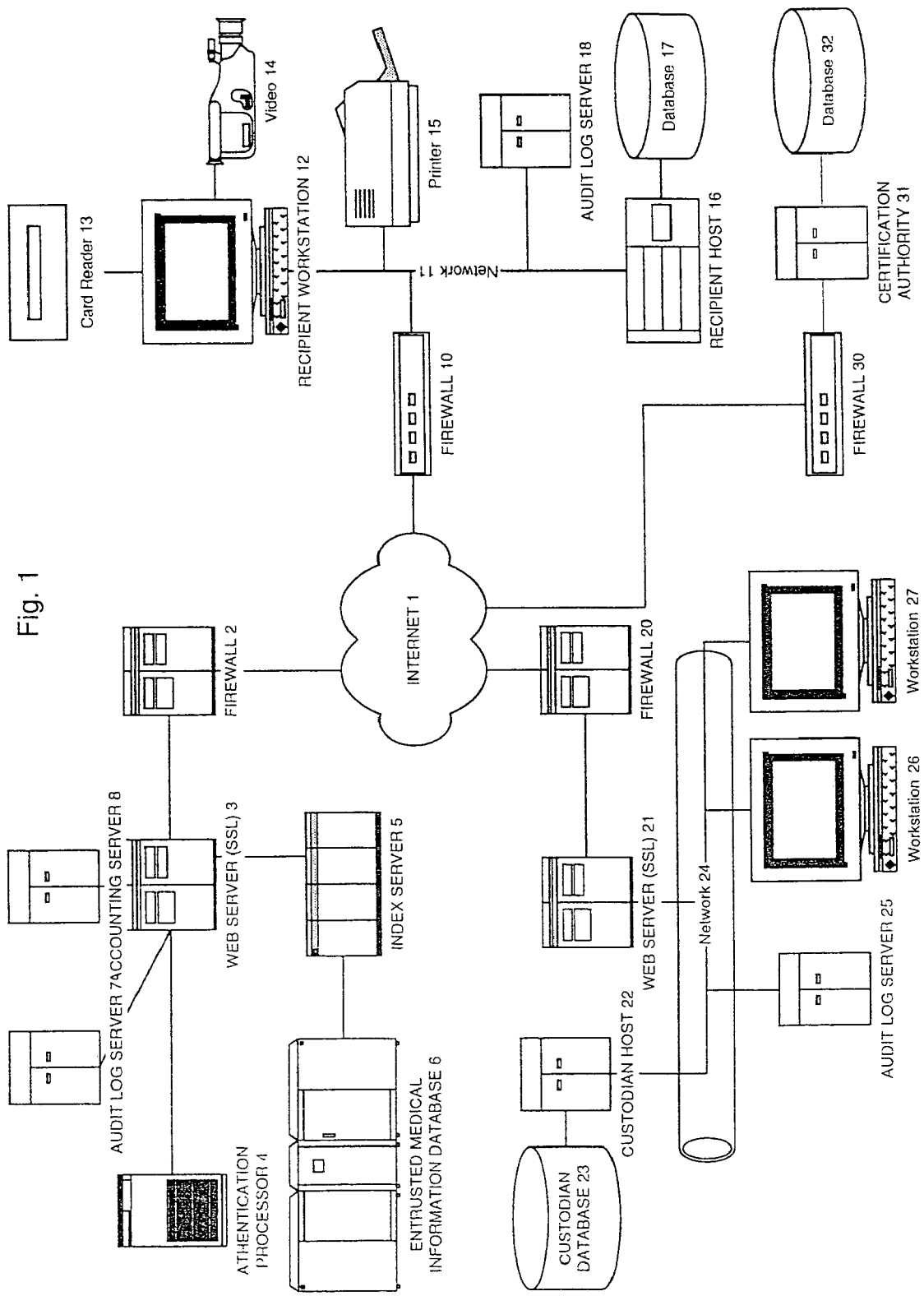
FIG. 1 illustrates a block diagram of the overall network architecture.

The system according to the present invention provides a conduit for the authorized transmission of records, which may be medical records, or other content, while maintaining the security of the records against unauthorized access or use. A preferred communications network is the Internet 1, a global interconnected set of public access networks, employing standardized protocols. Thus, the records may be transmitted virtually anywhere on earth using a single infrastructure. Alternately, private networks or virtual private networks (VPN) may be employed. In fact, as the system according to the present invention gains acceptance, a private network model (a "Medical Internet" or "Media Internet") is provided, in order to increase security and allow the system to be tuned to the types of data and quality of service demands made by users. A VPN employs encryption to shield communications between two cooperative sources from external observation.

Where the data is transmitted on a public network or outside of an institution, it is preferably encrypted using multi-layer public key encryption as well as SSL transport protocol, which is typically implemented by web servers 3, 21 and web browsers in workstations 12. Internet security measures typically provide a firewall 2, 10, 20, 30 between any internal network resources and the Internet.

In order to provide emergency access to system database contents, and to allow testing of system security and operation, a certification authority 31 generates and hold encryption keys in a secure database 32, which are released only under strictly defined circumstances.

The present invention provides a database 6 storing records, which may be encrypted or unencrypted. For example, the records may be patient records, encrypted with a cryptographic key associated with the respective patient.

The records may be received in encrypted form from a source, such as the custodian institution host 22, from custodian database 23. The custodian host 22 retrieves the patient medical record from the database, encrypts it, and transmits it through the internal network 24 to web server 21, through firewall 20, to the Internet. The encrypted file is received through the firewall 2 by web server 3, and stored, in conjunction with index server 5 in the entrusted medical information database 6. A set of access rules is associated with each record or discrete portion thereof, medical transaction record, along with the patient identifier and location of the encrypted medical transaction record, in the index server 5. The access rules may be a default set of rules, for example based on a recipient role, context of request, and/or rules defined by the patient or custodian institution. As is noted above, a trustee may act on behalf of the patient to authorize access and use, and to implement financial transactions, with respect to the records.

During each access to the custodian database 23, an entry is made with the audit log server 25 in the custodian system. Likewise, during each access of the index server 5 and/or entrusted medical information database 6, an entry is made with the audit log server 7 in the trustee system. A further aspect of the present invention provides a financial accounting server 8, allocating an expense for use of the trustee system resources.

A user of the trustee system typically seeks medical records belonging to a patient, although certain other uses of the system are permitted, in accordance with strictly enforced access, audit and accounting rules. The user, an intended recipient, access the system through a workstation, connected to the Internet 1 through internal network 11 and firewall 10. The user may be authenticated using, for example, a username and password, or authenticated using a security card in card reader 13, as well as a biometric identification, such as a facial image, captured by video camera 14. The user's credentials may be authenticated using profiles stored in the trustee system, the certification authority 31, or at the recipient host system 16, in database 17. The user's request, interactions with the trustee system, and access to medical records may all be logged in audit log server 18. In some cases, the user may, after receiving information, reproduce it on a computer system, such as an audiovisual display, produce hardcopy in printer 15, or otherwise generate output using the content. In other cases, hardcopy output may be restricted.

Figure 2:
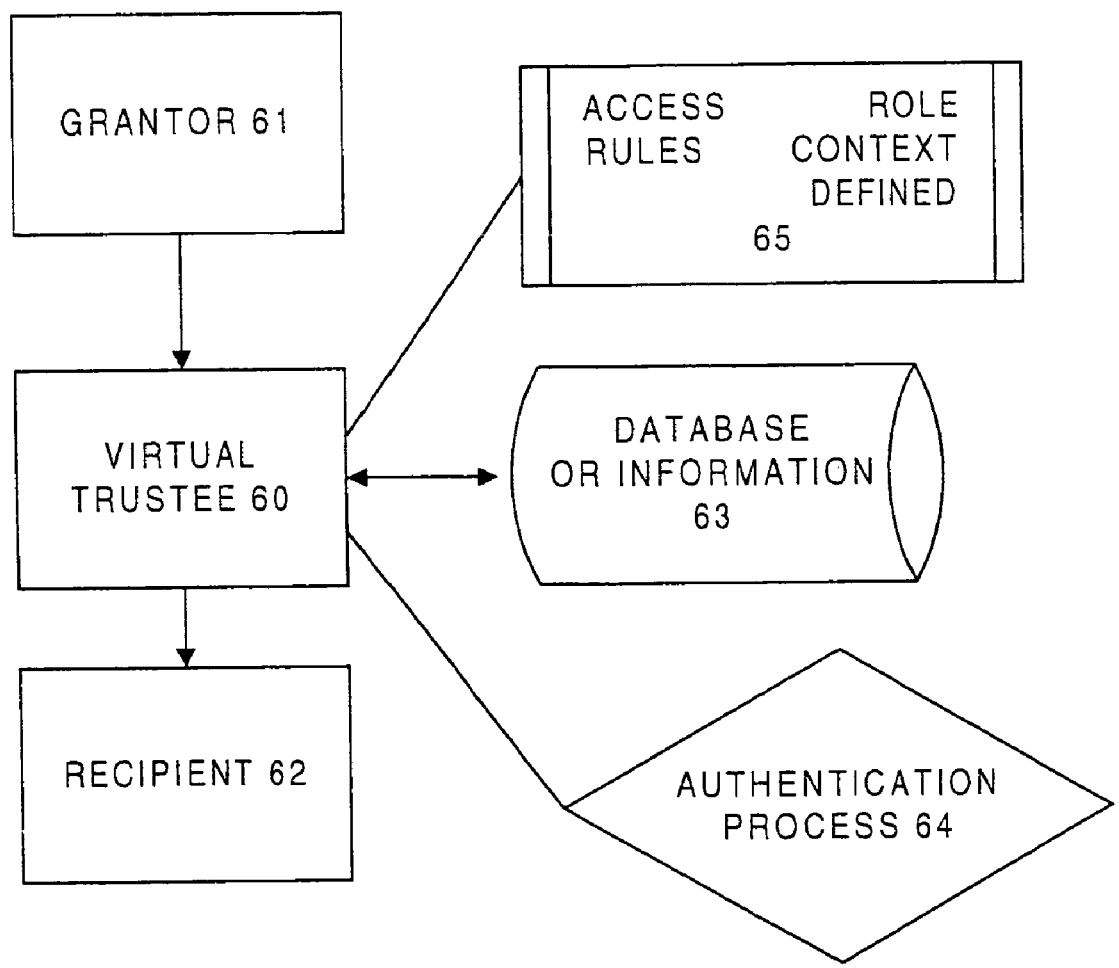
FIG. 2 illustrates a representation of a virtual information trust.

As represented in FIG. 2, the trustee is organized as a virtual trustee 60, holding digital information 63 in trust for the grantor 61. The trustee is responsible for authenticating recipient 62, as well as applying access rules 65, which may be role based, context based, and/or specifically defined by the patient, virtual trustee or custodian institution.

Figure 3:
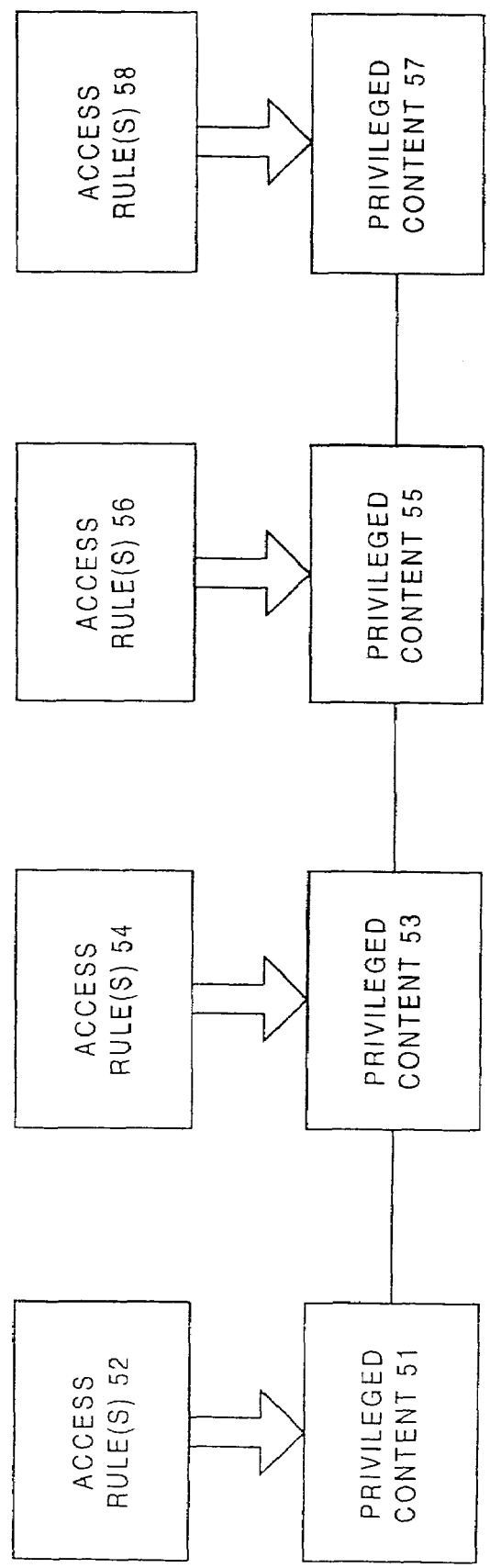
FIG. 3 illustrates a representation of a linked medical information records.
Figure 4:
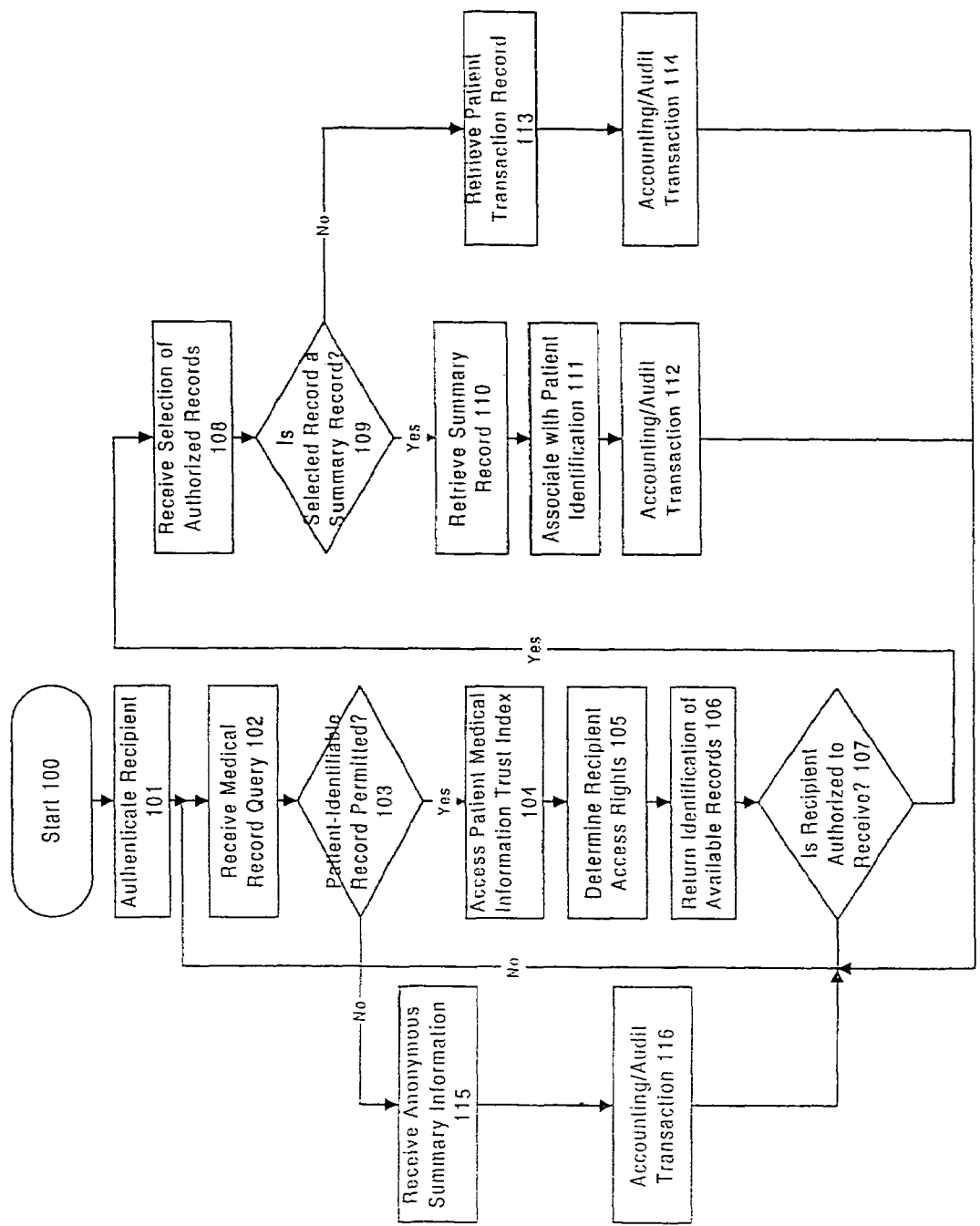
FIG. 4 is a flow chart showing a procedure for processing requests for medical record access.

For purposes of FIG. 3, the information content is considered user-private data. The access process begins 100 by the user accessing the trustee system. The user must be authenticated 101. The user presents a medical record query 102. In some cases, a user is not permitted to access patient-identifiable records 103. For example, an academic researcher may conduct a study of patient summary records. In this case, only anonymous summary record information 115 is accessible. The use of this data is audited and accounted 116.

According to an advertiser subsidy model, context-sensitive ads may be presented to users, who are generally medical professionals, while reviewing the records. Since these are context sensitive, they may be viewed as educational and relevant, and thus not disruptive. However, such context and context-sensitive information may also be considered private information. Thus, while the system accounts to the advertiser for the presentation of the ad, the identity and particular context of the patient, as well as the user, may be shielded from the advertiser. The context may be extracted in client software, which has access to decrypted patient records.

If patient identifiable information is available to the user, the patient medical information trust index is accessed 104. From the index, the access rights for the particular user are determined 105, and an identification returned to the user identifying available records within the access rights of the user 106. The recipient, after authentication of identity and role, is thus presented with a list of medical records available and/or existing 106.

For sensitive records, even the existence may be shielded, while for less sensitive records, the content is shielded while the existence is not. Examples of particularly sensitive information may include political, religious, sexual, and financial information. Therefore, in some instances, the user may be informed of the existence of a record without having access to the record. In other instances, even the existence of the record is shielded from the user.

If the recipient is authorized to both be informed of the existence of the record and to receive the record 107, the user is given the option to select desired records 108. The recipient then selects which records to receive, in an interactive process over the secure communications channel. The records are then "wrapped" with the controlled access applet, and encrypted with the recipient's public key and transmitted over the secure communications channel.

If a summary record is selected 109, it is retrieved 110, and specifically associated with the identified patient. Advantageously, electronically coded summary records may be intrinsically anonymous, and thus are identified only by association with the respective patient through an index. Thus, the same summary record, albeit without the patient personally identifying information, may be used for anonymous summary information searches 115. The use of the summary record may also trigger an accounting/audit transaction 112.

If the selected record is a patient transaction record 113, then the record is generally not anonymous, and only available to authorized users. The use of any patient record also triggers an accounting/audit transaction 114.

An index record is provided in the index server 5 for each database 6 entry, providing an identification of the patient, a locator for the associated record, and a set of access rules for the record, which may provide minimal information describing the record contents, such as the medical service, procedure, dates, or type of record. Typically, the index does not include a summary of the record or outcome.

As represented in FIG. 3, a medical record is formed as a set of privileged transaction records 51, 53, 55, 57, each having its own respective access rule(s) 52, 54, 56, 58. The content records relating to a single patient may be physically or logically associated with each other, as represented by the lines between the privileged content records 51, 53, 55, 57. The content is considered privileged in that access is restricted by understanding, contract or law.

These medical records thus are advantageously formed as a "Medical Information Polymer", each element having its own access rules 52, 54, 56, 58. Therefore, the index may include multiple independently-accessible record elements or a contiguous set of records 51, 53, 55, 57. Likewise, disparate and discontiguous records may be connected through the index, even if derived from different institutions or caregivers.

Since the access restrictions are defined at an atomic level of a medical information polymer, these may be applied both at the trustee server system, to limit access based on predefined rules, or at the recipient level, to limit access to desired records which are available based on the recipient authorization.

For example, a record is stored in a medical records database encrypted with a respective patient-associated public key. Upon transmission, the record is further encrypted with a transactional encryption algorithm (e.g., a session key), and further encrypted with the intended recipient's public key. The triple-encrypted message is then transmitted over a secure connection, e.g., SSL, or a VPN. In order to employ the medical record, the recipient first applies his private key, which may be stored in a physical token, such as a smart card, fob, or key. The recipient then engages in an on-line authentication/accounting transaction, to decrypt the transactional-level encoding. This activity is logged in an audit database 7, and the activities accounted in an accounting database 8. An applet "wrapper" associated with the record, in conjunction with the supplied patient-associated private key, allows decryption of the record itself, triggering potentially an additional accounting and/or audit transaction. Potentially (depending on the specific rules), each use of the encrypted record may require a separate on-line transaction accounting session.

Each use of the record may also trigger an accounting/audit event 112, 114, 116, thus allowing finely granular audit records of medical record access, and reduces the risks of security and privacy breach after record transmission. Importantly, this allows usage based financial accounting for the records, imposing a financial burden based according to value. Therefore, the revenues for maintenance of the system may be based on a number of factors, automatically calculated, which impose low costs for minimal usage of the records and larger costs on substantial use of the records.

When a recipient seeks a record, he must identify himself, in some cases his role in the authorized use of data or patient care, and the identity of the patient and/or record. The identification of the recipient is then authenticated 101, for example using a digital signature or challenge-response authentication scheme, in which messages are passed back and forth between the recipient and server. The recipient's role is checked for consistency with the recipient's identity, but may change in different contexts.

It is understood that the operation of the system generally does not depend on the content of the data. Therefore, instead of medical record data, the data could be media content data. In this case, an important issue concerns the privacy of the user, or recipient of the data. Thus, instead of shielding the subject of the data from unauthorized disclosure of the data, the system seeks to protect the content and the privacy of the user, while assuring that the owner of the content is compensated, and the content is not released without restrictions on use.

Example 2

John D. Halamka, Peter Szolovits, David Rind, and Charles Safran, "A WWW Implementation of National Recommendations for Protecting Electronic Health Information", J. Am. Med. Inform. Assoc. 1997 4: 458-464, expressly incorporated herein by reference, provide a prototype medical information database system (W3EMRS), called CareWeb, implemented at the Beth Israel Hospital (Boston Mass.), stored in a comprehensive, custom-built MUMPS-based system composed of 28,000 programs. The clinical data at the Deaconess Hospital is stored in a Sybase clinical data repository. CareWeb unites these systems using an implementation of the W3EMRS architecture.

The present invention differs somewhat from the CareWeb implementation, but is largely compatible. Thus, for example, the CareWeb system might implement an institutional active record database while the system according to the present invention also implements an independent multi-institutional archive database.

Individual Authentication of Users.

To properly authenticate individuals on any computer system containing health care data, every individual should have a unique secure identifier for access. Such a policy allows individuals to be held accountable for all actions taken while logged on. Thus, where a clerical worker seeks to retrieve a file for a professional, that worker should have and use accurate personal identification. Using role-based access rules, preferably verified on-line, the authority of the requester may be verified. Therefore, in order to transfer authority from a professional, e.g., an attending physician, to a clerical worker, the physician would delegate authority to the clerical employee using his own credentials, for example in a local institutional database. Thereafter, the trustee system according to the present invention, seeking to verify the access rules, would access the recipient (clerical employee) record at the local recipient institution, which would further provide the physician's credentials and inferred role based-access profile. After authentication, the clerical employee is granted access to the index record to select desired medical records. The encrypted record is forwarded to the clerical employee as recipient. However, decryption of the record requires the physician key. In like manner, the physician can, in accordance with policies of the local institution, provide authorization to the clerical employee to decrypt and process the record. However, the custodian medical institution or patient may set an enhanced security rule that requires that the authorized physician decrypt the record (or transaction contained in the record) personally.

Access Controls.

Many health care computing systems allow all users to view all information. There is, however, no good reason for a laboratory technician to read the confidential full text data contained in a patient psychiatric profile. Health care providers should be allowed to view clinical information on a need-to-know basis. The most obvious implementation of such controls would be to assign access to different health care computing functions based on job role. The present invention provides a system and method for transmitting all or a portion of the patient medical record in a secure "wrapper". This facilitates maintenance of privacy at the recipient institution, since the encrypted record may be maintained on the recipient private network and database with greatly reduced security and privacy risks. Preferably, the recipient computer record-keeping system fully supports the privacy features of the record, and therefore provides transparent support for the security and authentication features therein. For example, the secure wrapper may include a JAVA applet to authenticate the user and perform transactional communications and decryption. Therefore, the recipient institutional system need only provide a JAVA Virtual Machine (JVM), sufficient security permissions for operation, and sufficient communications permissions to conduct the on-line elements of the authentication, accounting and audit functions.

In one form of access control, different system functions are available based on job role. A more sophisticated implementation would tailor content within functions by job role. For example, a discharge summary could be viewed by both a physician and a billing coder, but details of the patient's psychiatric evaluation would not appear for the coder. Further, the coder typically would not have access to patient records transmitted from another institution, or to records from a past admission.

The authenticity of each user may be verified with a hardware token, such as the RSA SecurID hardware token. These tokens are small, handheld devices containing microprocessors that calculate and display unpredictable codes. These codes change at a specified interval, typically 60 seconds. For example, each user accessing CareWeb begins a session by entering a username, a memorized personal identification number (PIN), and the currently displayed password from the SecurID device. This information is transmitted to a security server, which authenticates the user and verifies that the correct password was entered. The security server compares the user-entered password with its knowledge of what password should have been entered for that 60 second period. If the password does not match, it also checks the password from the previous 60 second period to account for delays in typing and transmission. Once a password is verified, the user is authenticated for the duration of the session, or possibly with a maximum timeout limit, such as 15 minutes, whichever is shorter.

In the CareWeb system, an encrypted security "cookie" is sent back to the user's browser, and this cookie is automatically used for all future security dialogs. Using Visual Basic Script and Microsoft's Active Server Pages, the cookie is dynamically decrypted within the Web server and invisibly re-verify authentication before responding to additional requests for health care data. This, of course, presents security issues, since Visual Basic Script capabilities are a known security weakness.

The present invention therefore employs secure public key decryption for each record, at the client system, which may, of course, employ a hardware token similar to the SecurID device.

If the security token is lost or stolen, it can be immediately deactivated for the entire enterprise by disabling it at the security server.

Access Validation.

In the CareWeb system, in addition to storing encrypted username and password information, the security cookie contains the job role of the user. Again, this may pose security threats, for example if the security cookie is borrowed from the client machine, and employed in a second communication session within the time limit parameters. Displays of health care information are generated dynamically by Active Server page scripts, which are capable of assembling a multi-institutional medical record. The scripts can tailor delivered health care information based on the job role indicated by the cookie. This consolidation is avoided in the present invention, as the record must be decrypted before use. However, as a part of, or subsequent to, the decryption process, the decrypted information may be imported into a recipient database system, as long as the security permissions do not prohibit this.

Physical Security and Disaster Recovery.

The system according to the present invention transmits encrypted records, and thus physical security concerns are lessened. Standard precautions within the trustee system itself, such as positioning of computer terminals where they cannot be accessed by unauthorized users, and denying unauthorized personnel access to paper printouts and electronic storage are advisable. The trustee database is preferably replicated or distributed, both to provide fault tolerance and scalability. Backup tapes are therefore made frequently, and tapes housed off site in the case of a physical disaster.

Protection of Remote Access Points.

Since the system according to the present invention transmits encrypted records to authenticated individuals over a secure channel, this effectively amounts to firewall protection, i.e., protection against access by the general public. In fact, a firewall system proper is also present, in that the maintenance of the database is protected from public access, and the database proper is only accessible through the index server. The index server is further only accessible after user authentication. The firewall system thus provides strong, centralized security. All remote accesses are protected by single session or encrypted passwords, for example using challenge-response authentication schemes, SSL, VPNs or the like.

All patient-identifiable data transmitted over public networks is encrypted. As discussed above, the present invention preferably provides multiple levels of encryption of the patient data, with appropriate controls at each level.

An electronic signature may be used to "sign" submitted medical records, and a cryptographic digital signature should be used when retrieving records to ensure records are not modified during the transmission process. Recipients may also provide a request for records with a digital signature. Where role-based access rules are executed remotely from the trustee, these may be embedded in the record with a digital signature, such that if the rule set is tampered with, the record becomes essentially unusable.

Audit Trails.

While external "hackers" pose a security threat to medical records, a perhaps more important threat comes from "insiders", e.g., inappropriate health care data access from inside the organization. Such threats include the possibility of individuals not involved in a patient's care to look up the records of VIPs, celebrities, relatives, friends, and fellow employees. By providing a finely granular audit trail, including a log of all accesses to information, including time, date, information accessed, and user ID, a great disincentive will be created for medical professionals to inappropriately access records. Audit trails should be available for patient review on demand. Therefore, the present invention provides that an audit log be retained within the trustee (central) system, which may also be recorded at the recipient system. The custodian medical institution may also retain an access log for its records. The audit trail may be closely linked to an accounting database, to provide a basis for charging a patient or recipient for use of the record or services rendered in providing the record.

The accounting payments may be so-called micropayments, discussed above, fully verified transactions, such as credit-card type transactions, or simply "on account". Preferably, a micropayment model is adopted, since this may result in reduced transactional costs and greater efficiency. It is noted that, in the context of the present invention, the risk of default by any party is minimal, and thus a requisite presumption of a micropayment scheme is met.

Expanded Multi-organizational Audit Trails.

In any multi-institutional architecture there are multiple places to capture the audit, for example, at the institutional level, where the information is stored (the sites), at an intermediary level, such as the trustee, or at the point where the information is delivered. According to the present invention, the audit trail is captured at both levels, and indeed may also be transmitted, as appropriate, to the custodian medical institution or to the patient.

A multi-institutional auditing system facilitates patient's access to the details of the movement of their medical information throughout the health care enterprise. The trustee systems therefore preferably provides a function for patient access to such logs, and indeed to the record as a whole.

The CareWeb system employs RSA digital signatures to authenticate users. The present invention, however, may employ public key infrastructure to secure the record content as well, for example to provide patient security, recipient security, and session keys.

Thus, each request is signed with the recipient's private key. The request is sent to the server, which uses the associated public key to validate the digital signature through standard hashing and signature-verification methods. The server retrieves the information requested and may sign the response with its private key. The server then generates a session key, which it uses to encrypt the response. The session key is retained at the server, and released only after an accounting/audit transaction is completed. When the transaction logging/accounting is completed, the session key is then encrypted, using the recipient's public key. Thus, the encrypted session key and encrypted data may be sent back to the recipient separately, with an off-line or clerical transmission of the record file, which may be voluminous, and a separate on-line transaction to obtain the session key. The session key is decrypted using the recipient's private key. The encrypted response is decrypted using the decrypted session key. Finally, the response is validated using the server's public key. All decrypted site server messages are consolidated into a single Web page and returned to the original requesting browser over the Secure Sockets Layer.

Thus, the present invention allows for the desynchronization of transmission of the encrypted file and the authorization and accounting transactions for use of the encrypted information.

Digital signature cryptography methods may be used for all network transmissions, seeking to ensure the integrity of all health data delivered.

The recipient, after personal authentication and role authentication gains access to the index data, which provides a listing of available records or record identifiers. The information contained in the index is preferably minimalistic, such as "physical therapy", "discharge summary", "flowchart", "radiology", and possibly an associated date. In some instances, the database record consists of an entire hospitalization record. These identifiers may be used both to identify the record and to trigger access rules. The recipient then selects records for download, as discussed above.

An accounting and audit transaction is triggered, by the index access, downloading, and subsequent on-line transaction for decryption.

Other embodiments will be apparent to those skilled in the art from consideration of the specification and practice of the invention disclosed herein. It is intended that the specification and examples be considered as exemplary only, with a true scope of the invention being indicated by the following claims.

What is claimed is:

1. A method, comprising the steps of:
storing a plurality of digital records and respective access rules for each digital record in a computer memory associated with a server system;
receiving a request for access, from a remote computer, to access a digital record stored in the computer memory;
validating, by the server system, the received request to access the digital record by applying a respective set of access rules for the digital record stored in the computer memory;
retrieving, by the server system, a public key having an associated private key, and associating a logging wrapper having a respective session key with the digital record, after validating the received request, wherein the session key is distinct from the public key and the private key;
encrypting and sending, by the server system, the requested digital record which has been validated, using the public key and the session key to encrypt the digital record;
receiving and decrypting the encrypted digital record, by the remote computer, using the private key, and the session key in conjunction with the logging wrapper;
generating by the logging wrapper, at the remote computer, a logging event; and
recording the logging event in an access log.

2. The method according to claim 1, wherein the record is encrypted, further comprising the step of accounting for a decryption of the record after access to at least a portion thereof.

3. The method according to claim 2, wherein said accounting is anonymous.

4. The method according to claim 1, wherein the record has a plurality of portions, at least one portion being encrypted with at least one cryptographic key, said portions being independently accessible, said respective set of access rules applying to selectively limit access to portions of the record.

5. The method according to claim 4, wherein said respective set of access rules limit access to portions based on an identity of an intended recipient.

6. The method according to claim 1, further comprising the step of supplying a decryption key for a respective record portion in accordance with the respective set of access set of rules.

7. The method according to claim 1, further comprising the step of accounting for attempted access to at least a portion of the record.

8. The method according to claim 1, wherein the respective set of access rules are associated with an intended recipient of the record.

9. The method according to claim 1, further comprising the step of referencing an index to define a record.

10. The method according to claim 9, wherein the respective set of access rules comprise instructions to a trustee, defined under a legally enforceable trust agreement establishing a trust granting legal control over access to the record to a trustee subject to jurisdictional law of trusts, on behalf of a beneficiary.

11. The method according to claim 1, further comprising the step of using an index to identify a record potentially responsive to a query.

12. The method according to claim 1, further comprising the step of using an index comprising a set of associations of patient identities and medical transaction records to identify records relating to a respective patient.

13. The method according to claim 1, further comprising the step of using an index comprising a set of associations of record identification, record characteristic, and said access rules to identify records relating to a query and limiting access to portions thereof.

14. The method according to claim 1, wherein the record comprises a plurality of portions, the portions being separately encrypted and having associated sets of independent rules.

15. The method according to claim 1, wherein the access rules are role based access rules relating to a role of the intended recipient.

16. The method according to claim 1, wherein the access rules are context based access rules relating to a context of record access.

17. The method according to claim 10, wherein the respective set of access rules are defined by a grantor of the trust.

18. The method according to claim 1, wherein a decryption of the record triggers a remotely-sensed transaction.

19. The method according to claim 18, wherein the remotely sensed transaction comprises a financial accounting transaction.

20. The method according to claim 18, wherein the remotely sensed transaction comprises an access audit trail transaction.

21. The method according to claim 2, wherein said accounting occurs upon supply of the respective decryption key.

22. The method according to claim 2, wherein said accounting occurs upon use of the respective decryption key.

23. The method according to claim 1, wherein the record comprises a medical record.

24. The method according to claim 1, wherein the record comprises a media content record.

25. The method according to claim 24, wherein the media content record is distributed peer-to-peer.

26. The method according to claim 1, wherein the respective set of access rules are interpreted in accordance with a database of jurisdiction-dependent privacy laws.

27. The method according to claim 10, further comprising the step of creating a trust comprising the record, implemented in accordance with the trust laws of a specified jurisdiction.

28. The method according to claim 1, wherein the record comprises separate articles within a digital publication.

29. The method according to claim 1, further comprising the step of receiving the respective set of access rules.

30. The method according to claim 1, further comprising the step of generating the respective set of access rules based on the record.

31. The method according to claim 1, wherein the record is encrypted with an encryption scheme having a rolling code.

32. The method according to claim 10, wherein the trustee controls the records and implements the access rules without requiring access to a content of the records.

33. The method according to claim 10, wherein the trustee acts without requiring access to the records.

34. The method according to claim 10, wherein the trustee selectively processes the records.

35. The method according to claim 1, wherein the records comprise a type selected from the group consisting of legal information, government records, financial records, commercially valuable trade secret legal information, manufacturing information, banking information, consumer entertainment media, digital music files, video information, cinema information, consumer information, personal demographic information, credit card information, personal contact information, social security number information, publication information, separate articles within a digital publication, and investment account information.

36. The method according to claim 1, wherein the record comprises a patient file, placed in a privileged trust for the patient with a trustee, said trustee implementing the respective set of access rules with respect to each transaction record within the patient file defined by the patient and legal jurisdiction, wherein said trustee interacts with the patient record information to at least one of maintain, process, receive, deliver, and transmit portions of the patient file in secure and verifiable fashion to authorized entities in compliance with the trust.

37. The method according to claim 10, wherein the record comprises a corpus of a medical information trust for holding medical records on behalf of a patient distinct from the caregiver; the trustee charging for access to the medical record, and maintaining a record of each access of the medical record.

38. The method according to claim 10, wherein the trust has a beneficiary and the respective set of access rules is applied to limit access by an identified intended recipient, without communicating an identity of the intended recipient to the beneficiary.

39. The method according to claim 1, further comprising the steps of:
 placing information represented by the record in legal trust under control of a trustee on behalf of the beneficiary, said information being stored in electronically readable form;
 automatically authorizing access to the information in trust based on compliance with a trust-defined rule, comprising requiring an electronic communication between a user and the trustee; and
 permitting an authorized user to access the information in the trust through an electronic communication.

40. The method according to claim 39, wherein the trust defined rule comprises a compensation rule for obtaining a right to the information.

41. The method according to claim 40, wherein the electronic communication comprises an electronic funds transfer.

42. The method according to claim 40, wherein the compensation rule is integrally associated with the information, and wherein the implementing occurs as a result of user interaction with the information.

43. The method according to claim 39, wherein the information comprises a patient medical record.

44. The method according to claim 39, wherein the information comprises consumer entertainment media.

45. The method according to claim 39, wherein the trustee is interposed between the beneficiary and the user, the trustee maintaining an anonymity of the user while accounting to the beneficiary.

46. The method according to claim 39, wherein the trustee is interposed between the beneficiary and the user, the trustee characterizing the user based on a classification of information usage, while accounting to the beneficiary for the use, without specifically identifying information usage of a user.

47. The method according to claim 39, wherein a transfer of the information to the user requires an electronic transfer of value from the user to the trustee, further comprising the step of accepting the value by the trustee while stripping an identification of the user from a retained transfer record.

48. The method according to claim 39, further comprising the steps of receiving an identification of desired information content from a user; and logging the access employing a digital signature of the user.

49. The method according to claim 48, wherein the digital signature is anonymous with respect to the beneficiary.

50. The method according to claim 48, wherein the authorizing step entails requiring the user to enter into a restrictive covenant.

51. The method according to claim 40, wherein the trustee manages access to the information and implements the respective set of access rules as an intermediary for, and communicates compensation information to, the beneficiary.

52. The method according to claim 40, wherein the information has an associated compensation value, and comprises digital media information, said digital media information being associated with subsidy content having an associated subsidy value, further comprising the step of accounting for use of the digital media information offset by the subsidy value.

53. The method according to claim 1, further comprising the steps of:
defining information content of a record and an associated set of access rules;
electronically transmitting the information content and associated set of access rules to the trustee subject to the terms of the trust agreement;
storing the transmitted information content and associated set of access rules as a respective one of the plurality of records and a respective set of access rules; and
automatically implementing, under control of the trustee, the associated access rules with respect to the information content, to establish a virtual trust in accordance therewith, whereby the trustee selectively authorizes access to the information content to selectively permit communication of the information content.

54. The method according to claim 53, wherein the information content comprises media information, and the associated access rules comprise economic rules.

55. The method according to claim 53, wherein the information content comprises medical record information, and the associated access rules comprise restrictive access rules based on an identity or characteristic of a requestor.

56. The method according to claim 55, further comprising the step of transmitting, from the trustee, information content in accordance with the associated rules.

57. The method according to claim 53, wherein the trustee controls the information content and implements the rules without requiring access to the information content.

58. The method according to claim 1, wherein the logging wrapper logs the access based on a digital signature of the third party.

59. The method according to claim 1, wherein the third party is required to enter into a restrictive covenant for access to the information.

60. The method according to claim 1, wherein the record comprises a plurality of medical transaction information files, associated with the specific patient, each medical transaction information file being separately encrypted, and being subject to a separate role-based access rule and a searchable index identifying a content of said medical transaction information files, a search of said index being role-based rule sensitive to withhold index information from unauthorized users.

61. The method according to claim 60, wherein the record comprises at least two medical transaction information files, each file being separately encrypted.

62. The method according to claim 60, further comprising respective access rule embedded in the medical transaction information file.

63. The method according to claim 60, wherein the respective access rule is not encrypted.

64. The method according to claim 60, wherein the medical transaction file encryption comprises public key encryption.

65. The method according to claim 60, wherein the medical transaction file encryption comprises multiple levels of public key encryption, employing differing keys.

66. The method according to claim 60, wherein the medical transaction file encryption comprises a first public key encryption employing a patient-specific public key, and a second public key encryption employing a recipient specific public key.

67. The method according to claim 60, wherein the medical transaction file encryption comprises a public key encryption employing a recipient-system interaction specific key.

68. The method according to claim 67, wherein the medical transaction file encryption further comprises a first public key encryption employing a patient-specific public key, and a second public key encryption employing a recipient specific public key.

69. The method according to claim 67, wherein said recipient-system interaction specific key interacts with an applet wrapper to decrypt the medical record.

70. The method according to claim 60, wherein the record is in a database system for hosting the medical transaction information files, further comprising the step of accounting for access to a content of each of said encrypted medical transaction information files.

71. The method according to claim 70, wherein the accounting is a financial accounting.

72. The method according to claim 70, further comprising the step of generating an audit trail.

73. The method according to claim 1, wherein at least one of the respective access rules comprises:
charging for access to or permission to access the record by causing at least one of a monetary transfer through a monetary transfer system and an accounting entry in an accounting database representing a proposed monetary transfer; and
storing a record of at least one of each access of and permission to access the record in a database.

74. The method according to claim 73, wherein the access permission comprises a cryptographic key.

75. The method according to claim 1, further comprising the steps of:
establishing under jurisdictional trust laws, in an entity distinct from a rights holder, a virtual information trust in accordance with the legally enforceable trust agreement, to hold the record or associated access permission on behalf of a beneficiary;
providing a database system, comprising a plurality of records, each record having an associated set of respective access rules;
the trustee operating under the virtual information trust and applying the respective access rules on behalf of the beneficiary in accordance with the virtual information trust;
charging for access to or permission to access the content record by causing at least one of a monetary transfer and an accounting entry representing a proposed monetary transfer; and
maintaining a record of each access of or permission to access the content record.

76. The method according to claim 75, wherein the access permission comprises a cryptographic key.

77. The method according to claim 1, further comprising the steps of:
(a) defining the terms of a legally enforceable trust between a grantor and a trustee, on behalf of a beneficiary, for maintaining an information record in trust subject to the respective set of access rules, said information record comprising property of value;
(b) conveying the information record to the trustee, as a corpus of the trust; and
(c) accounting to the beneficiary for financial value attributable to the trust.

78. A database system, comprising a plurality of digital records, each digital record having an associated set of access rules, stored in a computer memory associated with a server system;
an interface computer in communication with a remote computer, receiving a request for access from the remote computer to access a digital record stored in the computer memory;

an automated processor. associated with the server system,
validating the received request to access the digital record by applying a respective set of access rules for the digital record stored in the computer memory;
retrieving a public key having an associated private key, and associating a logging wrapper having a respective session key with the digital record, after validating the received request, wherein the session key is distinct from the public key and the private key;
encrypting and sending the requested digital record which has been validated, using the public key and the session key to encrypt the digital record, through the interface computer;
receiving, through the interface computer, a logging event from the remote computer based on an operation of the wrapper and at least the session key; and
recording the logging event in an access log.

79. The system according to claim 78, wherein the record is encrypted, further comprising means for accounting for a decryption of the record.

80. The system according to claim 79, wherein said accounting is anonymous.

81. The system according to claim 78, wherein the record has a plurality of portions, each portion being encrypted with at least one cryptographic key, said portions being independently accessible, said respective access rules applying to selectively limit access to portions of the record.

82. The system according to claim 81, wherein said access rules limit access to portions based on an identity of an intended recipient.

83. The system according to claim 78, wherein the record comprises a plurality of encrypted portions, further comprising the step of supplying a decryption key for a respective record portion in accordance with the respective access rules.

84. The system according to claim 78, wherein at least a portion of the record is encrypted, further comprising an accounting system for accounting for a decryption of a portion of the record.

85. The system according to claim 78, wherein the respective access rules are associated with an intended recipient of the record.

86. The system according to claim 78, further comprising the step of referencing an index to define a record.

87. The system according to claim 86, wherein the index further stores respective access rules for qualifying an intended recipient with respect to each of the records.

88. The system according to claim 87, further comprising the step of using an index to identify a record potentially responsive to a query.

89. The system according to claim 78, wherein the record comprises a medical record, and wherein an index of a set of associations of patient identities and medical transaction records is used to identify records relating to a respective patient.

90. The system according to claim 78, wherein an index of a set of associations of record identification, record characteristic, and said respective access rules to identify records relating to a query and limiting access to portions thereof.

91. The system according to claim 78, wherein the record comprises a plurality of portions, the portions being separately encrypted and having associated therewith sets of independent respective rules.

92. The system according to claim 78, wherein the respective access rules are role based access rules relating to a role of an intended recipient.

93. The system according to claim 78, wherein the respective access rules are context based access rules relating to a context of record access.

94. The system according to claim 78, wherein the respective access rules are defined by a grantor of the trust.

95. The system according to claim 78, wherein a decryption of the record triggers a remotely-sensed transaction.

96. The system according to claim 95, wherein the remotely sensed transaction comprises a financial accounting transaction.

97. The system according to claim 95, wherein the remotely sensed transaction comprises an access audit trail transaction.

98. The system according to claim 79, wherein said accounting occurs upon supply of the respective decryption key.

99. The system according to claim 79, wherein said accounting occurs upon use of the respective decryption key.

100. The system according to claim 78, wherein the record comprises a medical record.

101. The system according to claim 78, wherein the record comprises a media content record.

102. The system according to claim 78, wherein the respective access rules are interpreted in accordance with a database of jurisdictional trust laws.

103. The system according to claim 78, wherein the respective access rules are interpreted in accordance with a database of jurisdiction-dependent privacy laws.

104. The system according to claim 78, further comprising the step of creating a virtual trust encompassing the record, implemented in accordance with the trust laws of an associated jurisdiction.

105. The system according to claim 78, wherein the records comprise separate articles within a digital publication.

106. The system according to claim 78, further comprising the step of receiving the respective access rules.

107. The system according to claim 78, further comprising the step of generating the respective access rules based on the record.

108. The system according to claim 78, wherein a record is encrypted with an encryption scheme having a rolling code.

109. The system according to claim 78, wherein the rules are administered by a trustee who controls the records and implements the respective access rules without requiring access to a content of the record.

110. The system according to claim 78, wherein the rules are administered by a trustee who controls access to the records.

111. The system according to claim 110, wherein the trustee selectively processes the records.

112. The system according to claim 78, wherein the records comprise a type selected from the group consisting of legal information, government records, financial records, commercially valuable trade secret legal information, manufacturing information, banking information, consumer entertainment media, digital music files, video information, cinema information, consumer information, personal demographic information, credit card information, personal contact information, social security number information, publication information, separate articles within a digital publication, and investment account information.

113. The system according to claim 78, wherein a record comprises a patient file, placed in a privileged trust for the patient with a trustee, said trustee implementing the set of rules for access with respect to each transaction record within the patient file, the respective rules being defined by the patient and legal jurisdiction, wherein said trustee interacts with the patient record information to at least one of maintain, process, receive, deliver, and transmit portions of the patient record in secure and verifiable fashion to authorized entities in compliance with the trust.

114. The method according to claim 78, wherein the wrapper logs the access based on a digital signature of the third party.

115. The system according to claim 78, wherein the information comprises digital media information, said digital media information being associated with subsidy content, wherein an economic compensation for access by a user to the digital media information is offset by a value for subsidy content.

116. The database system according to claim 78, further comprising:
   a set of associated selective rights, corresponding to a record, held as at least a portion of a corpus of a trust, for restricting at least one of access, use, storage and transmission of a respective set of defined content information, organized as a legal entity under the laws of a jurisdiction; and
   a trustee acting under the trust laws of the jurisdiction, receiving the associated rights and implementing a virtual trust in accordance therewith,
   wherein the trustee communicates through an electronic communications system to selectively convey permission to at least one of access, use, store and transmit the respective set of defined content information in accordance with the respective access rules.

117. The system according to claim 116, wherein the information content comprises media information, and the rights comprise economic rules.

118. The system according to claim 116, wherein the information content comprises medical record information, and the rights comprise restrictive access rules based on an identity or characteristic of a user.

119. The system according to claim 118, further comprising the step of transmitting, from the trustee, information content in accordance with the rights.

120. The system according to claim 116, wherein the trustee controls the information content and implements rights-based restrictions without requiring access to the information content.

121. The system according to claim 116, wherein the defined information content is provided as a set of records, each record having a plurality of portions, at least two such portions being associated with independent cryptographic keys, further comprising a database index providing an association between a record descriptor, a record identification, and a set of limiting access rules for each privileged database record; and a cryptographic key database, for storing cryptographic keys associated with portions of a record.

122. The system according to claim 116, wherein said rights are a set of rules selected from the group consisting of one or more of role based access rules, and context based access rules.

123. The system according to claim 121, wherein each of the portions is encrypted with at least one cryptographic key, said portions being independently accessible.

124. The system according to claim 121, further comprising means for accounting for a decryption of an encrypted record or portion of a record.

125. The system according to claim 121, wherein the records comprise medical records.

126. The system according to claim 116, wherein the rights are interpreted in accordance with a database of jurisdictional trust laws.

127. The system according to claim 116, wherein the rights are jurisdiction-dependent, further comprising an input for receiving an identification of a relevant jurisdiction.

128. The system according to claim 127, further comprising means for resolving inconsistencies between a plurality of relevant jurisdictions.

129. The system according to claim 127, further comprising a plurality of sets of rights, each set of rights being associated with a different jurisdiction, further comprising means for applying a set of rights relevant to an associated jurisdiction.

130. The system according to claim 116, further comprising a transaction log including a digital signature of a transactor, wherein the transaction log may be audited through authentication of the digital signature.

131. The system according to claim 130, wherein the transaction log may be audited without revealing an identity of the transactor.

132. The system according to claim 130, wherein the transaction log audited reveals an identity of the transactor.

133. A method, comprising the steps of:
   storing a plurality of digital records and respective access rules for each digital record in a computer memory associated with a server system;
   receiving a request for access, from a remote computer, to access a digital record stored in the computer memory;
   validating, by the server system, the received request to access the digital record by applying a respective set of access rules for the digital record stored in the computer memory;
   retrieving, by the server system, a public key having an associated private key, and associating a wrapper having a respective session key with the digital record, wherein the session key is distinct from the public key and the private key;
   encrypting and sending, by the server system, the requested digital record after validating the received request, using the public key and the session key to encrypt the digital record;
   receiving the encrypted digital record, by the remote computer, and decrypting the encrypted digital record using the private key and the session key in conjunction with the wrapper;
   generating by the wrapper, at the remote computer, a logging event; and
   accounting, at the server, for the decrypting by the remote computer using the wrapper.

134. The method according to claim 133, wherein the respective set of access rules comprise instructions to a trustee, defined under a legally enforceable trust agreement establishing a trust granting legal control over access to the record to a trustee subject to jurisdictional law of trusts, on behalf of a beneficiary.

135. The method according to claim 134, wherein the trustee generates commercial subsidies in conjunction with transactions involving a record.

136. The method according to claim 134, wherein the trustee conducts a financial transaction with respect to a record, and financially compensates the beneficiary for the transaction.

137. The method according to claim 133, further comprising the step of presenting paid advertising to an accessor of the record.

138. The method according to claim 133, further comprising the step of presenting context-sensitive advertising to an accessor of the record, paid by the advertiser based on a quantity of presentation thereof.

139. The method according to claim 138, wherein an accounting to the advertiser excludes confidential information.

140. A database system, comprising:
- at least one retrieval computer retrieving a plurality of digital records and having at least one access log, each digital record having an associated set of access rules;
- at least one communications interface computer in communication with a remote computer, communicating a request for access, from the remote computer, to access a digital record stored in the at least one retrieval computer; and
- at least one processor for:
  - selectively controlling the at least one retrieval computer to retrieve a record in dependence on a compliance with a respective set of access rules;
  - validating the received request to access the digital record by applying a respective set of access rules for the digital record stored in the at least one retrieval computer;
  - retrieving a public key having an associated private key, and associating a wrapper having a respective session key with the digital record, after validating the received request, wherein the session key is distinct from the public key and the private key;
  - encrypting and sending the requested digital record which has been validated, using the public key and the session key to encryp the digital record, through the at least one communications interface computer;
  - receiving, through the at least one communications interface computer, a logging event from the remote computer based on an operation of the wrapper and at least the session key; and
  - recording the logging event in an access log.

141. The database system according to claim 140, wherein each respective set of access rules represents instructions to a trustee operating under an established legal trust, applying the access rules on behalf of a beneficiary in accordance with the legal trust, the respective access rules, and the jurisdictional trust law.

142. A method, comprising the steps of:
- storing a set of access rules in a database stored in a first computer memory;
- defining a plurality of sets of information content stored in a second computer memory at a server system, the sets of information content being subject to associated access rules stored in the database;
- transmitting information defining the associated access rules for the respective plurality of sets of information content from the first computer memory to a database control system at the server system;
- automatically, under control of the database control system at the server system, analyzing the associated access rules with respect to the respective information content, and implementing the transmitted associated access rules dependent on a context of attempted access of the respective information content, to thereby validate a request for access;
- retrieving, by the server system, a public key having an associated private key, and associating a wrapper having a respective session key with the respective information content, wherein the session key is distinct from the public key and the private key;
- encrypting, by the server system, the requested respective information content using the public key and the session key to encrypt the digital record, and associating the respective information content in an encrypted form with a wrapper;
- communicating the respective information in an encrypted form and the wrapper, after validating the respective request for access, an access to a decrypted form of the information content at a remote computer being dependent on at least the wrapper, the session key and the private key;
- communicating an event from the remote computer to the server system, by the wrapper; and
- accounting for access to the information content and a respective context in an access log at the server system.

143. The method according to claim 142, wherein the respective set of access rules comprise instructions to a trustee, defined under a legally enforceable trust agreement establishing a trust granting legal control over access to the record to a trustee subject to jurisdictional law of trusts, on behalf of a beneficiary, the limitations of the trust being enforced under authority of the trustee in accordance with the trust agreement, the respective set of access rules, and the jurisdictional law of trusts.

* * * * *